(12) United States Patent
Ohashi et al.

(10) Patent No.: US 11,262,653 B2
(45) Date of Patent: *Mar. 1, 2022

(54) SULFONIUM SALT, POLYMER, RESIST COMPOSITION, AND PATTERNING PROCESS

(71) Applicant: Shin-Etsu Chemical Co., Ltd., Tokyo (JP)

(72) Inventors: Masaki Ohashi, Joetsu (JP); Jun Hatakeyama, Joetsu (JP); Teppei Adachi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 288 days.

This patent is subject to a terminal disclaimer.

(21) Appl. No.: 16/042,179

(22) Filed: Jul. 23, 2018

(65) Prior Publication Data

US 2019/0033716 A1    Jan. 31, 2019

(30) Foreign Application Priority Data

Jul. 27, 2017  (JP) .............................. JP2017-145057

(51) Int. Cl.
| | | |
|---|---|---|
| *G03F 7/039* | (2006.01) | |
| *C08L 41/00* | (2006.01) | |
| *C07C 381/12* | (2006.01) | |
| *C07C 309/12* | (2006.01) | |
| *G03F 7/004* | (2006.01) | |
| *C08F 228/02* | (2006.01) | |
| *G03F 7/11* | (2006.01) | |
| *G03F 7/20* | (2006.01) | |
| *C08F 20/38* | (2006.01) | |
| *C07D 327/06* | (2006.01) | |
| *C08F 12/14* | (2006.01) | |
| *C08F 12/22* | (2006.01) | |

(52) U.S. Cl.
CPC ............ *G03F 7/039* (2013.01); *C07C 309/12* (2013.01); *C07C 381/12* (2013.01); *C08F 228/02* (2013.01); *C08L 41/00* (2013.01); *G03F 7/0045* (2013.01); *G03F 7/0046* (2013.01); *G03F 7/0397* (2013.01); *G03F 7/11* (2013.01); *G03F 7/2041* (2013.01); *C07D 327/06* (2013.01); *C08F 12/14* (2013.01); *C08F 12/22* (2013.01); *C08F 20/38* (2013.01)

(58) Field of Classification Search
CPC ...... G03F 7/039; G03F 7/0392; C07C 381/12
See application file for complete search history.

(56) References Cited

U.S. PATENT DOCUMENTS

| | | | |
|---|---|---|---|
| 10,101,653 B2 * | 10/2018 | Hatakeyama | ........... G03F 7/322 |
| 2017/0075218 A1 * | 3/2017 | Hatakeyama | ......... G03F 7/2059 |
| 2017/0115566 A1 | 4/2017 | Hatakeyama et al. | |
| 2018/0039173 A1 * | 2/2018 | Hatakeyama | ......... C07C 309/06 |

FOREIGN PATENT DOCUMENTS

| | | |
|---|---|---|
| JP | 2009-080160 A | 4/2009 |
| JP | 2009-080161 A | 4/2009 |
| JP | 2011-037836 A | 2/2011 |

OTHER PUBLICATIONS

Office Action dated Jun. 9, 2020, issued in counterpart JP Application No. 2017-145057, with English Translation. (11 pages).

* cited by examiner

*Primary Examiner* — Daborah Chacko-Davis
(74) *Attorney, Agent, or Firm* — Westerman, Hattori, Daniels & Adrian, LLP

(57) ABSTRACT

A polymer comprising recurring units derived from a sulfonium salt of specific structure having a polymerizable group is coated to form a resist film which is amenable to precise micropatterning because of improved LWR, CDU and resolution.

6 Claims, 2 Drawing Sheets

SULFONIUM SALT, POLYMER, RESIST COMPOSITION, AND PATTERNING PROCESS

CROSS-REFERENCE TO RELATED APPLICATION

This non-provisional application claims priority under 35 U.S.C. § 119(a) on Patent Application No. 2017-145057 filed in Japan on Jul. 27, 2017, the entire contents of which are hereby incorporated by reference.

TECHNICAL FIELD

This invention relates to a sulfonium salt, a polymer, a resist composition and a patterning process.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, manufacturing of microelectronic devices at the 65-nm node by the ArF lithography has been implemented in a mass scale. Manufacturing of 45-nm node devices by the next generation ArF immersion lithography is approaching to the verge of high-volume application. The candidates for the next generation 32-nm node include ultra-high NA lens immersion lithography using a liquid having a higher refractive index than water in combination with a high refractive index lens and a high refractive index resist film, EUV lithography of wavelength 13.5 nm, and double patterning version of the ArF lithography, on which active research efforts have been made.

As the pattern feature size is reduced, approaching to the diffraction limit of light, light contrast lowers. In the case of positive resist a lowering of light contrast leads to reductions of resolution and focus margin of hole and trench patterns.

As the pattern feature size is reduced, the edge roughness (LWR) of line patterns and the critical dimension uniformity (CDU) of hole patterns are regarded significant. It is pointed out that these factors are affected by the segregation or agglomeration of a base polymer and acid generator and the diffusion of generated acid. There is a tendency that as the resist film becomes thinner, LWR becomes greater. A film thickness reduction to comply with the progress of size reduction causes a degradation of LWR, which becomes a serious problem.

The EUV lithogaphy resist must meet high sensitivity, high resolution and low LWR at the same time. As the acid diffusion distance is reduced, LWR is reduced, but sensitivity becomes lower. For example, as the PEB temperature is lowered, the outcome is a reduced LWR, but a lower sensitivity. As the amount of quencher added is increased, the outcome is a reduced LWR, but a lower sensitivity. It is necessary to overcome the tradeoff relation between sensitivity and LWR.

DISCLOSURE OF INVENTION

In the field of acid-catalyzed chemically amplified resist materials, it is desired to have an acid generator capable of achieving a higher sensitivity, improved LWR of line patterns, and improved CDU of hole patterns.

An object of the invention is to provide a resist composition which exhibits a high sensitivity, a reduced LWR or improved CDU, and a high resolution, independent of whether it is of positive tone or negative tone; and a pattern forming process using the same.

The inventors have found that a resist composition comprising a polymer comprising recurring units derived from a sulfonium salt of specific structure having a polymerizable group forms a resist film having a reduced LWR, improved CDU, and high resolution and is effective for precise micropatterning.

In one aspect, the invention provides a sulfonium salt comprising an anion having the formula (1a) and a sulfonium cation having the formula (1b) or (1c).

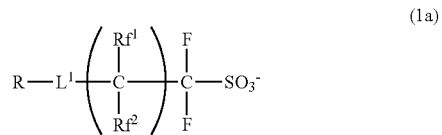

Herein R is a $C_1$-$C_{20}$ straight, branched or cyclic monovalent hydrocarbon group containing at least one iodine atom, which may contain a heteroatom other than iodine, $Rf^1$ and $Rf^2$ and each independently hydrogen, fluorine or trifluoroethyl, n is an integer of 0 to 5, and $L^1$ is a single bond, or a divalent group containing an ether bond, thioether bond, ester bond, sulfonic acid ester bond, carbonate bond or carbamate bond.

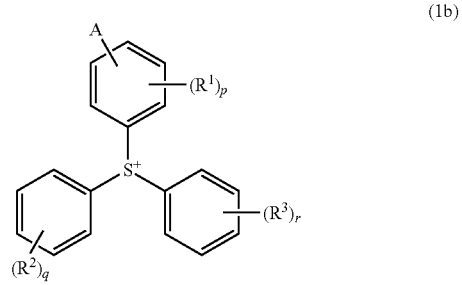

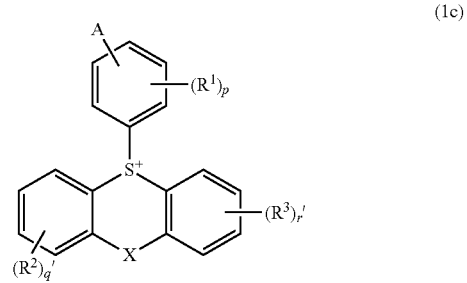

Herein A is an organic group having a polymer table group, $R^1$, $R^2$ and $R^3$ are each independently a halogen, nitro, cyano, or $C_1$-$C_{20}$ straight, branched or cyclic monovalent hydrocarbon group which may contain a heteroatom, where a plurality of groups $R^1$, $R^2$ or $R^3$ are included, two adjacent groups $R^1$, $R^2$ or $R^3$ may bond together to form a ring with the carbon atoms to which they are attached, X is a single bond, or —O—, —NH—, —S—, —SO—, —$SO_2$—, —CO— or —$CH_2$—, p is an integer of 0 to 4, q and r each independently an integer of to 0 to 5, q' and r' are each independently an integer of 0 to 4.

In a preferred embodiment, the sulfonium cation has the formula (1b-1) or (1c-1):

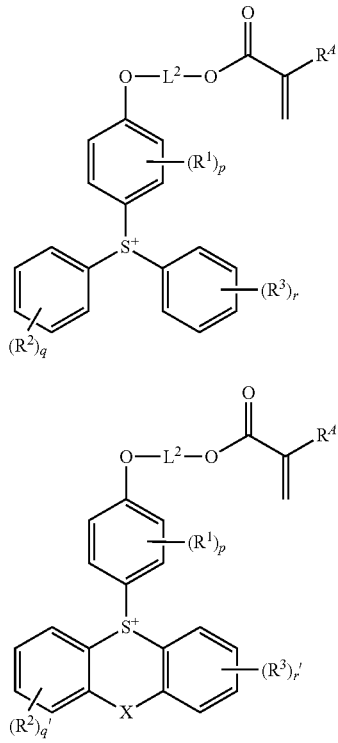

wherein $R^1$, $R^2$, $R^3$, X, p, q, r, q' and r' are as defined above, $L^2$ is a $C_1$-$C_{20}$ straight, branched or cyclic divalent hydrocarbon group which may contain a heteroatom, and $R^4$ is each independently hydrogen or methyl.

In a preferred embodiment, the anion has the formula (1a-1):

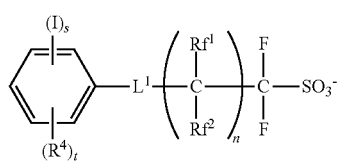

wherein $Rf^1$, $Rf^2$, $L^1$ and n are as defined above, $R^4$ is a $C_1$-$C_{20}$ straight, branched or cyclic monovalent hydrocarbon group which may contain a heteroatom, s is an integer of 1 to 5. t is an integer of 0 to 4, and 1≤s+t≤5.

In a more preferred embodiment, the anion has the formula (1a-2):

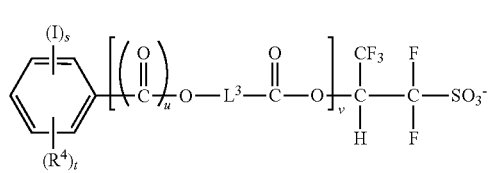

wherein $R^4$, s and t are as defined above, $L^3$ is a $C_1$-$C_{20}$ straight, branched or cyclic divalent hydrocarbon group which may contain a heteroatom, u and v are each independently 0 or 1.

In a second aspect, the invention provides a polymer comprising recurring units derived from the sulfonium salt defined above.

In a preferred embodiment, the polymer further comprises recurring units having the formula (a), (b) or (c).

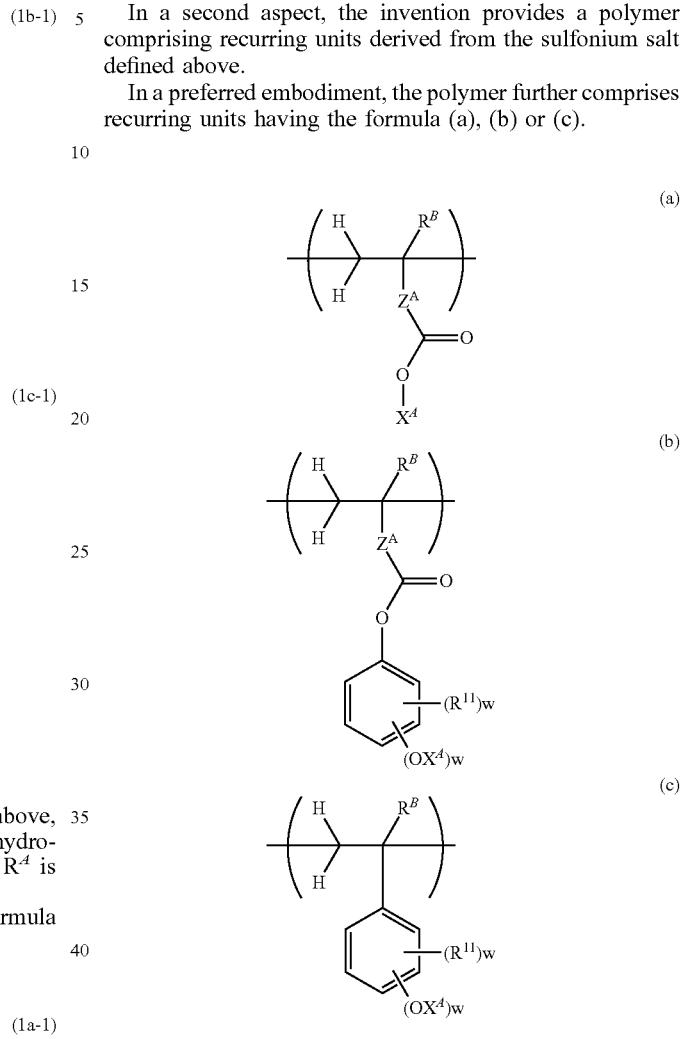

Herein $R^B$ is hydrogen, fluorine, methyl or trifluoromethyl, $Z^A$ is a single bond, phenylene group, naphthylene group or (backbone)-C(=O)-O-$Z^B$-, wherein $Z^B$ is a $C_1$-$C_{10}$ slight, branched or cyclic alkylene group which may contain a hydroxyl, ether bond, ester bond or lactone ring, or a phenylene naphthylene group, $X^A$ is an acid labile group, $R^{11}$ is halogen, nitro, cyano, or a $C_1$-$C_{10}$ straight, branched or cyclic monovalent hydrocarbon group which may contain a heteroatom, w is an integer of 0 to 4, x is 1 or 2, and 1≤w+x≤5.

In a preferred embodiment, the polymer further comprises recurring units having the formula (d) or (e).

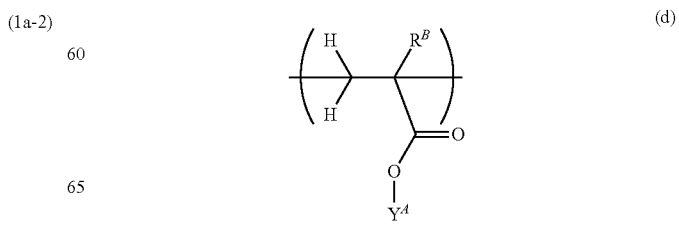

-continued

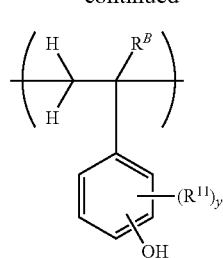

(e)

Herein $R^B$ and $R^{11}$ are as defined above, $Y^A$ is hydrogen or a polar group having at least one structure selected from hydroxy, cyano, carbonyl, carboxy, ether bond, ester bond, sulfonic acid ester bond, carbonate bond, lactone ring, sultone ring and carboxylic anhydride, and y is an integer of 0 to 4.

In a further aspect, the invention provides a resist composition comprising a base polymer containing the polymer defined above.

The resist composition may further comprise an organic solvent, a photoacid generator free of a polymerizable group, an acid diffusion inhibitor, and/or a surfactant which is insoluble or substantially insoluble in water and soluble in alkaline developer or a surfactant which is insoluble or substantially insoluble in water and alkaline developer.

In a still further aspect, the invention provides a process for forming a pattern comprising the steps of applying the resist composition defined herein onto a substrate, prebaking to form a resist film, exposing the resist film to KrF excimer laser, ArF excimer laser, EB or EUV, baking, and developing the exposed film in a developer.

Preferably, the exposing step is by immersion lithography wherein a liquid having a refractive index of at least 1.0 is interposed between the resist film and a projection lens.

The process may further comprise the step of forming a protective film on the resist film, and in the immersion lithogaphy, the liquid is interposed between the protective film and the projection lens.

ADVANTAGEOUS EFFECTS OF INVENTION

Using a resist composition comprising a polymer comprising recurring units derived from a sulfonium salt of specific structure, a pattern of satisfactory profile having reduced LWR, improved CDU and high resolution can be formed.

DESCRIPTION OF EMBODIMENTS

Figure 1:
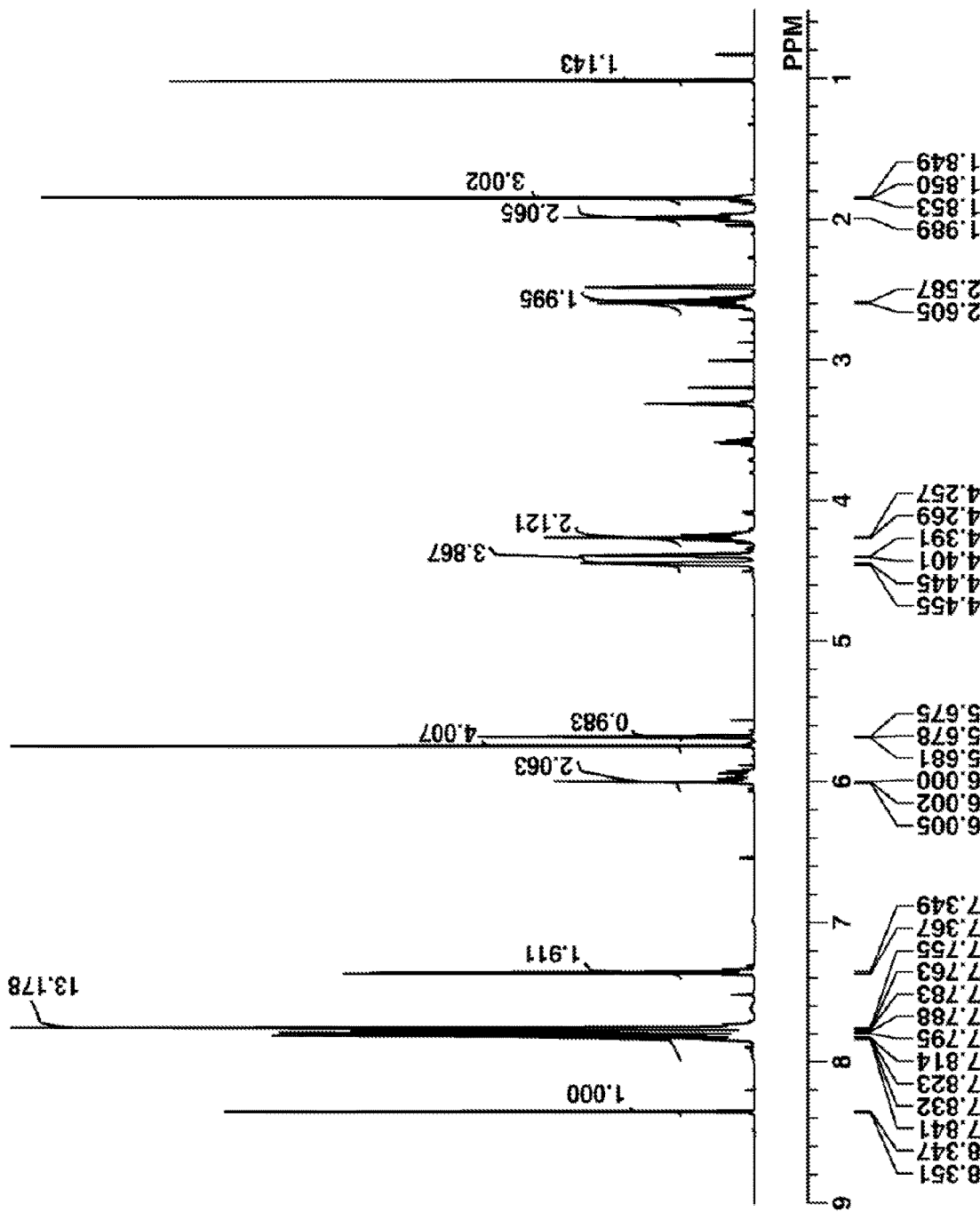
FIGS. 1 and 2 are diagrams showing $^1$H- and $^{19}$F-NMR spectra of compound PAG-A in Example 1-5, respectively.

As used herein, the singular forms "a," "an" and "the" include plural referents unless the context clearly dictates otherwise. The notation ($C_n$-$C_m$) means a group containing from n to m carbon atoms per group. In chemical formulae, the broken line designates a valence bond. As used herein, the term "iodized" or "fluorinated" indicates that a compound contains iodine or fluorine.

The abbreviations and acronyms have the following meaning.

EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LWR: line width roughness
CDU: critical dimension uniformity Sulfanium Salt One embodiment of the invention is a sulfonium salt comprising an anion and a cation. The anion has the formula (1a).

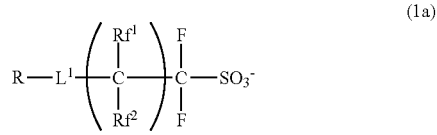

(1a)

In formula (1a), R is a $C_1$-$C_{20}$ straight, branched or cyclic monovalent hydrocarbon group containing at least one iodine atom, which may contain a heteroatom other than iodine. $Rf^1$ and $Rf^2$ are each independently hydrogen, fluorine or trifluoromethyl, and n is an integer of 0 to 5. $L^1$ is a single bond, or a divalent group containing an ether bond, thioether bond, ester bond, sulfonic acid ester bond, carbonate bond or carbamate bond.

Examples of the monovalent hydrocarbon group include alkyl groups such as methyl, ethyl, propyl, isopropyl, n-butyl, sec-butyl, t-butyl, n-pentyl, t-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl, and aryl groups such as phenyl, naphthyl, and anthracenyl. In these hydrocarbon groups, one or more hydrogen may be replaced by a moiety containing a heteroatom such as oxygen, sulfur, nitrogen or halogen, or a carbon atom may be replaced by a moiety containing a heteroatom such as oxygen, sulfur or nitrogen, so that the group may contain a hydroxy moiety, cyano moiety, carbonyl moiety, ether bond, thioether bond, ester bond, sulfonic acid ester bond, carbonate bond, carbamate bond, lactone ring, sultone ring, carboxylic anhydride or haloalkyl moiety. It is necessary that R be a group containing at least one iodine atom, i.e., one or more hydrogen on the alkyl or aryl group is replaced by iodine.

$L^1$ is a single bond or a divalent group. Examples of the divalent group include an ether bond, thioether bond, ester bond, sulfonic acid ester bond, carbonate bond or carbamate bond, and $C_1$-$C_{30}$ straight, branched or cyclic divalent hydrocarbon groups containing such a bond. Suitable divalent hydrocarbon groups are the same as will be exemplified for $L^2$.

The cation of the sulfonium salt has the formula (1b) or (1c).

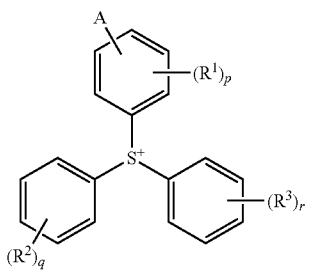
(1b)

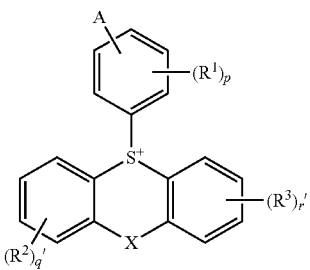
(1c)

In formulae (1b) and (1c), A is an organic group having a polymerizable group. Suitable polymerizable groups include acryloyl, methacryloyl, vinyl and allyl, with methacryloyl and vinyl being preferred.

In formulae (1b) and (1c), $R^1$, $R^2$ and $R^3$ are each independently a halogen, nitro, cyano, or $C_1$-$C_{20}$ straight, branched or cyclic monovalent hydrocarbon group which may contain a heteroatom. Where a plurality of groups $R^1$, $R^2$ or $R^3$ are included, two adjacent groups $R^1$, $R^2$ or $R^3$ may bond together to form a ring with the carbon atoms to which they are attached. Suitable monovalent hydrocarbon groups are as exemplified above.

In formula (1c), X is a single bond, or —O—, —NH—, —S—, —SO—, —SO$_2$—, —CO— or —CH$_2$—. Suitable partial structures including X are shown below.

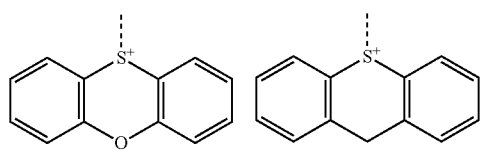

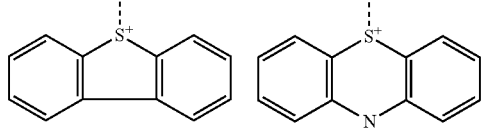

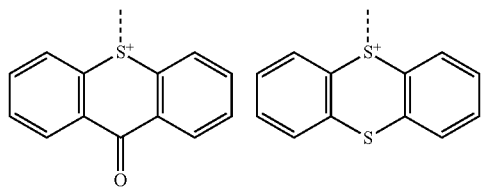

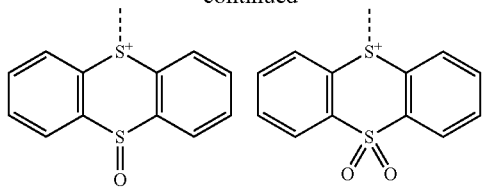

In formulae (1b) and (1c), p is an integer of 0 to 4, preferably 0 or 2. In formula (1b), q and r are each independently an integer of 0 to 5, preferably 0 to 2. In formula (1c), q' and r' are each independently an integer of 0 to 4, preferably 0 to 2.

The preferred cations having formula (1b) or (1 c) are those having the formula (1b-1) or (1c-1).

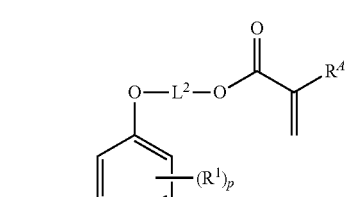
(1b-1)

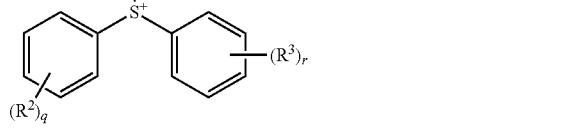

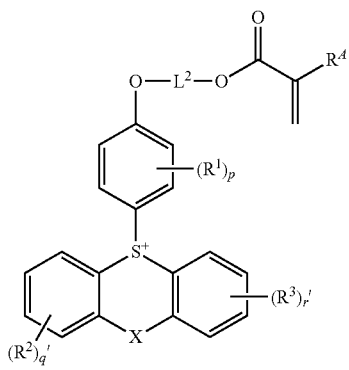
(1c-1)

Herein $R^1$, $R^2$, $R^3$, X, p, q, r, q' and r' are as defined above, $L^2$ is a $C_1$-$C_{20}$ straight, branched or cyclic divalent hydrocarbon group which may contain a heteroatom. $R^A$ is each independently hydrogen or methyl.

Suitable divalent hydrocarbon groups include straight alkanediol groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,11-diyl, tridecane-1,13-diyl, tetradecane-1,14-diyl pentadecane-1,15-diyl, hexadecane-1,16-diyl, and heptadecane-1,17-diyl; saturated cyclic hydrocarbon groups such as cyclopentanediyl, cyclohexanediyl, norbornanediyl, and adamantanediyl; and unsaturated cyclic hydrocarbon groups such as phenylene and naphthylene. Also included are substituted forms of the foregoing groups in which one or more hydrogen atoms are substituted by an alkyl group(s) such as methyl, ethyl, propyl, n-butyl, or tert-butyl; substituted forms of the foregoing groups in which one or more hydrogen atoms are substituted by a group containing a heteroatom such as oxygen, sulfur, nitrogen or halogen atom; and substituted forms of the foregoing groups in which carbon atom is substituted by a group containing a heteroatom such as oxygen, sulfur or nitrogen atom, so that the group contains a hydroxyl, cyano, carbonyl, ether bond, ester bond, sulfonic acid ester bond, carbonate bond, lactone ring, sultone ring, carboxylic anhydride or haloalkyl moiety. Of these, $L^2$ is preferably ethylene or propane-1,3-diyl.

The preferred anions having formula (1a) are those having the formula (1a-1).

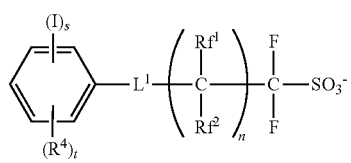
(1a-1)

In formula (1a-1), $Rr^1$, $Rf^2$, $L^1$ and n are as defined above, $R^4$ is a $C_1$-$C_{20}$ straight, branched or cyclic monovalent hydrocarbon group which may contain a heteroatom, s is an integer of 1 to 5, t is an integer of 0 to 4, and $1 \leq s+t \leq 5$. Suitable monovalent hydrocarbon groups are as exemplified above.

The more preferred anions having formula (1a) are those having the formula (1a-2).

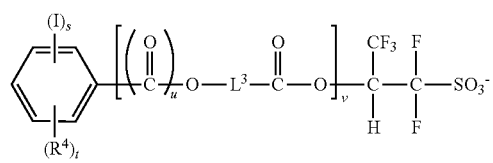
(1a-2)

In formula (1a-2), $R^4$, s and t are as defined above. $L^3$ is a $C_1$-$C_{20}$ straight, branched or cyclic divalent hydrocarbon group which may contain a heteroatom. Suitable divalent hydrocarbon groups are as exemplified above. $L^3$ is preferably methylene or propane-1,3-diyl. The subscripts u and v are each independently 0 or 1.

Of the sulfonium salts of the invention, salts consisting of an anion of formula (1a) and a cation of formula (1b-1) or (1c-1) are preferred, salts consisting of an anion of formula (1a-1) and a cation of formula (1b-1) or (1c-1) are more preferred, and salts consisting of an anion of formula (1a-2) and a cation of formula (1b-1) or (1c-1) are most preferred.

Examples of the cation of formula (1b) or (1c) are shown below, but not limited thereto.

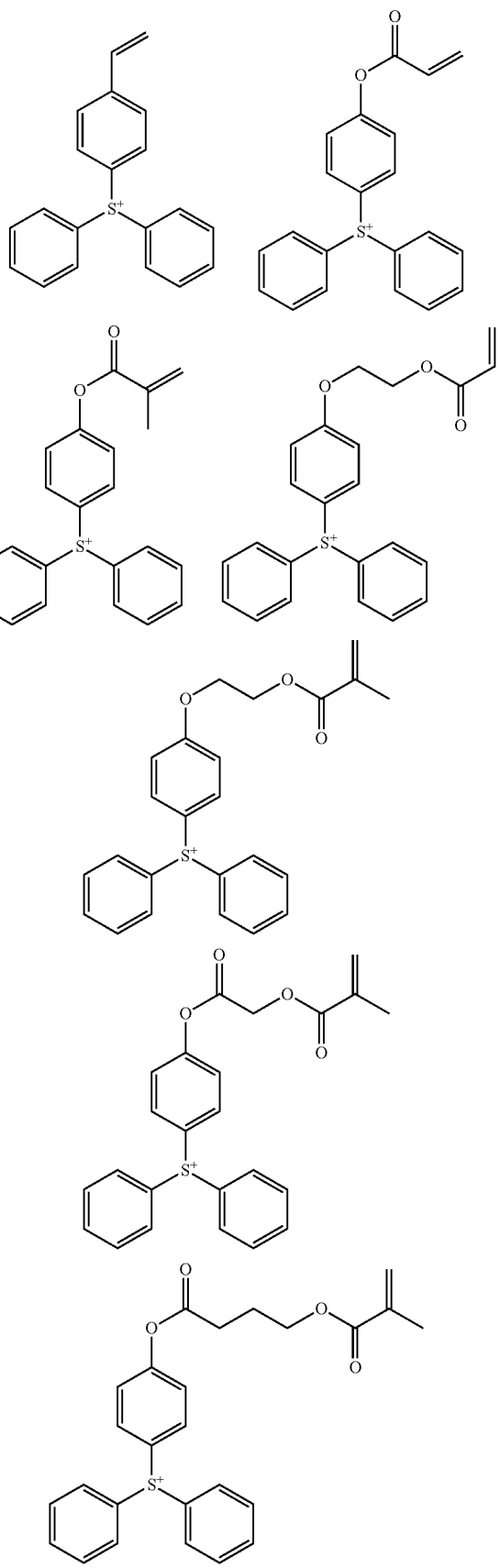

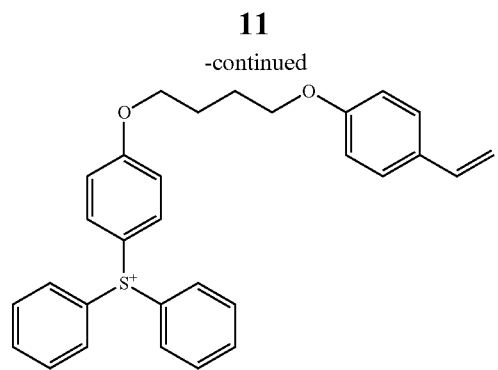
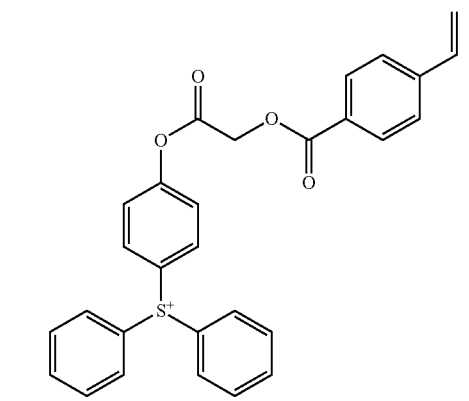
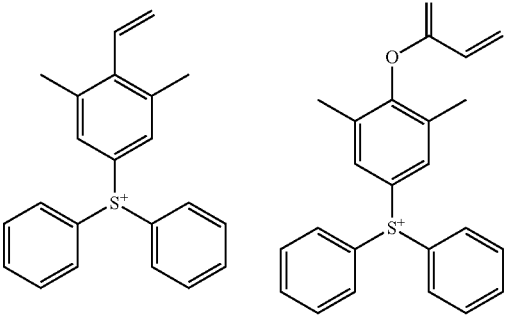
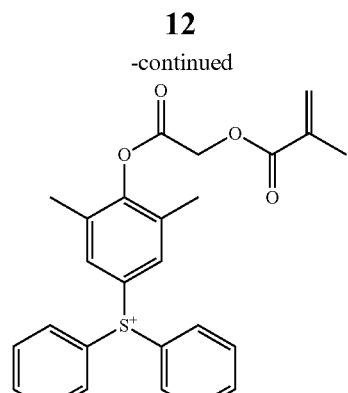
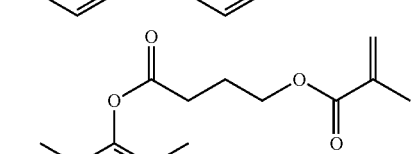
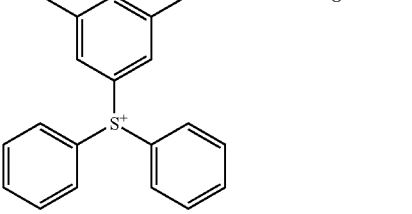
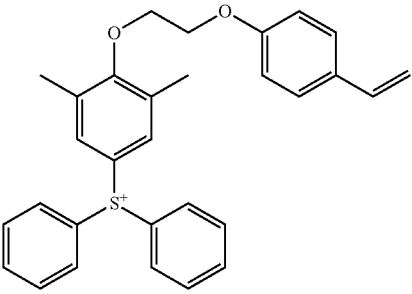
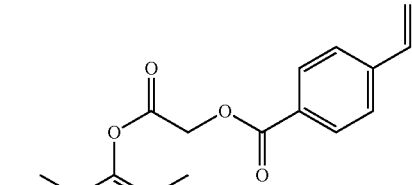
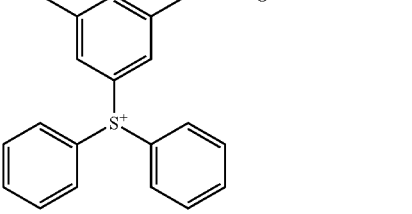
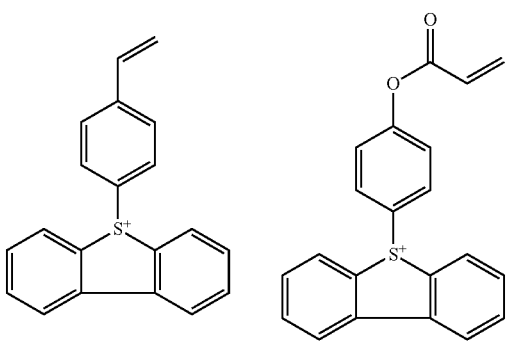

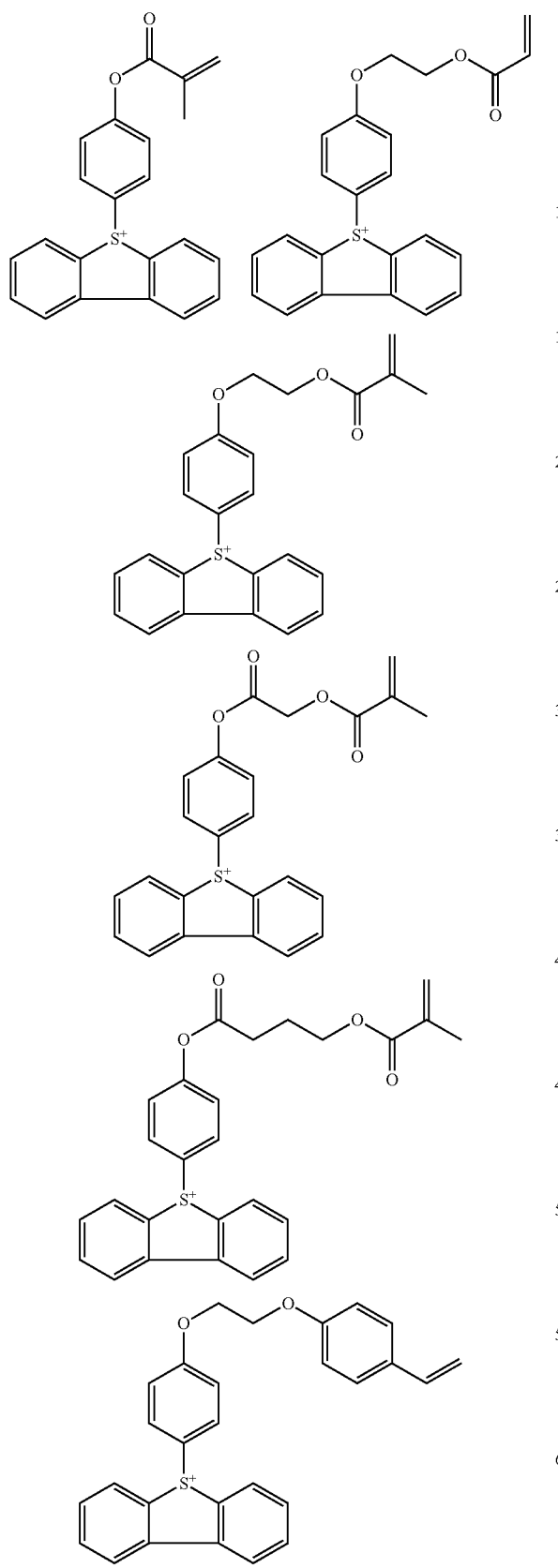
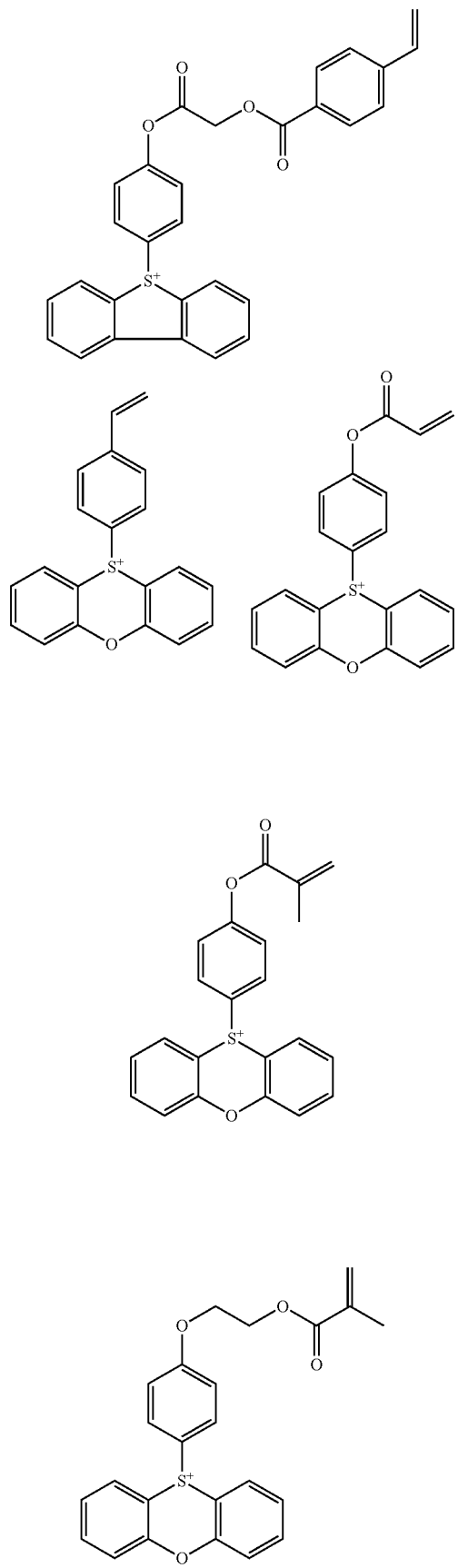

-continued
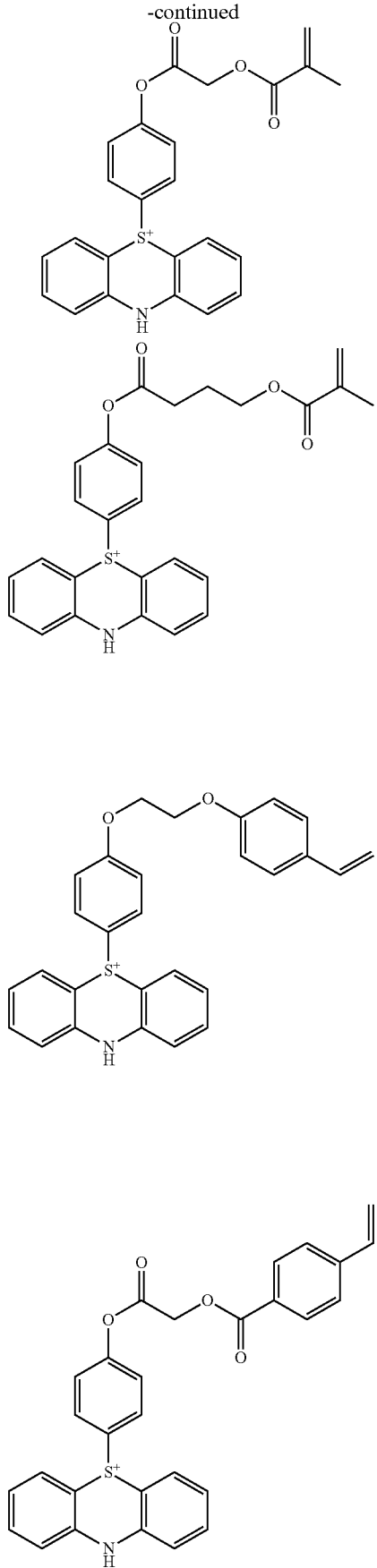
-continued
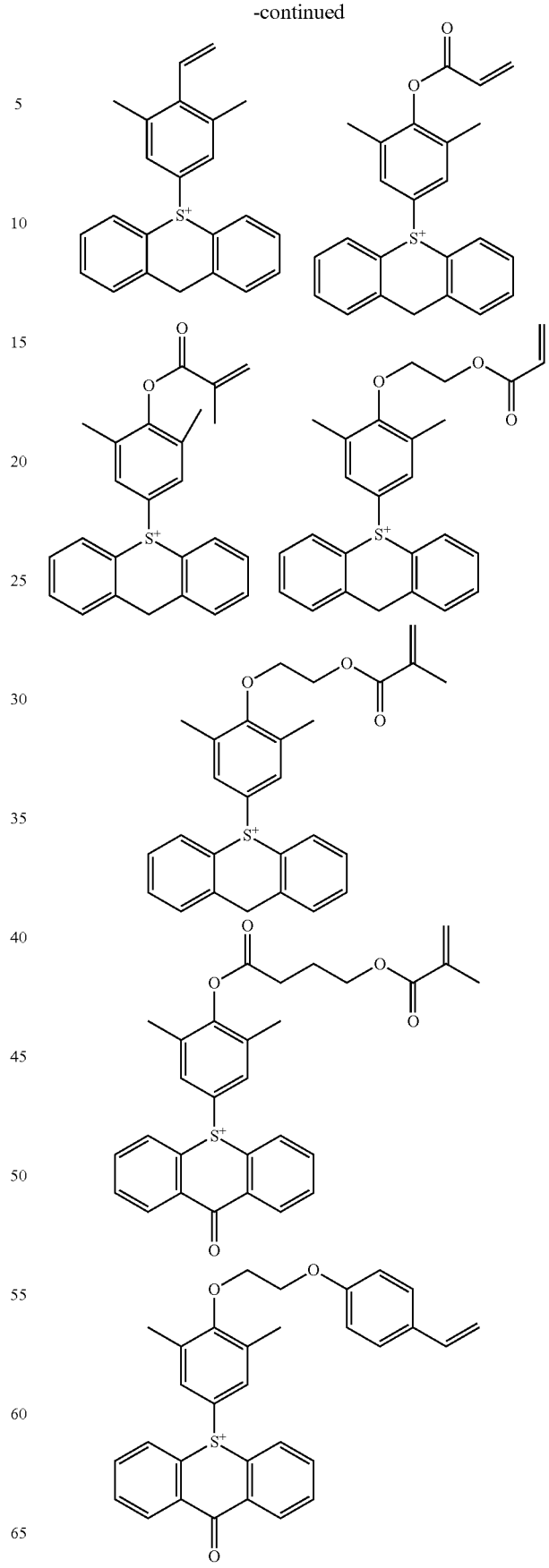

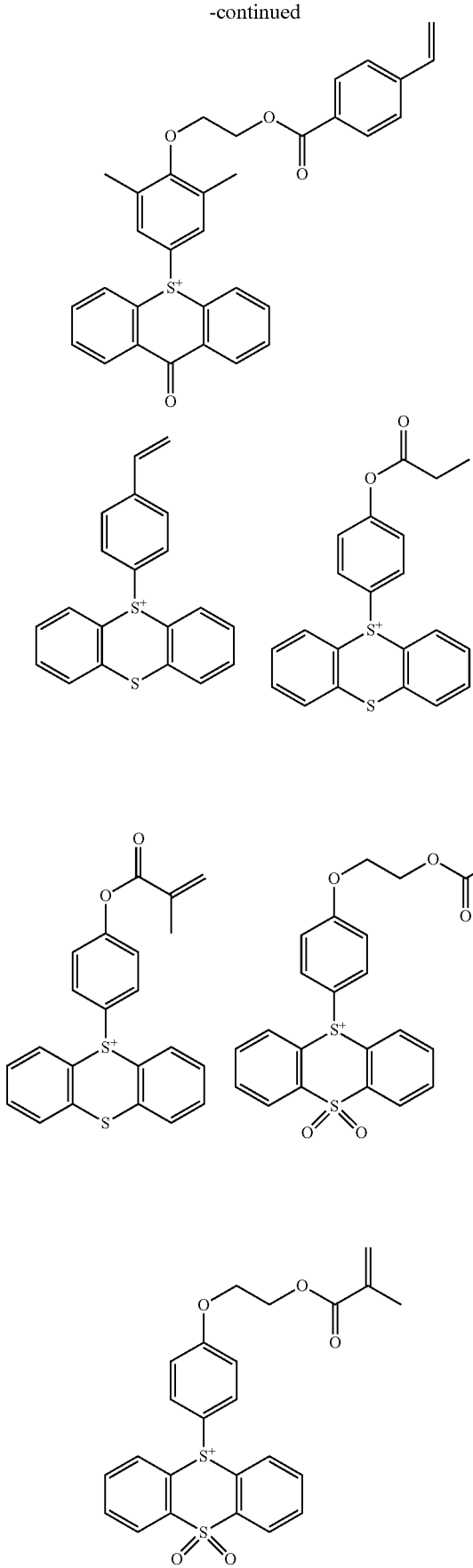
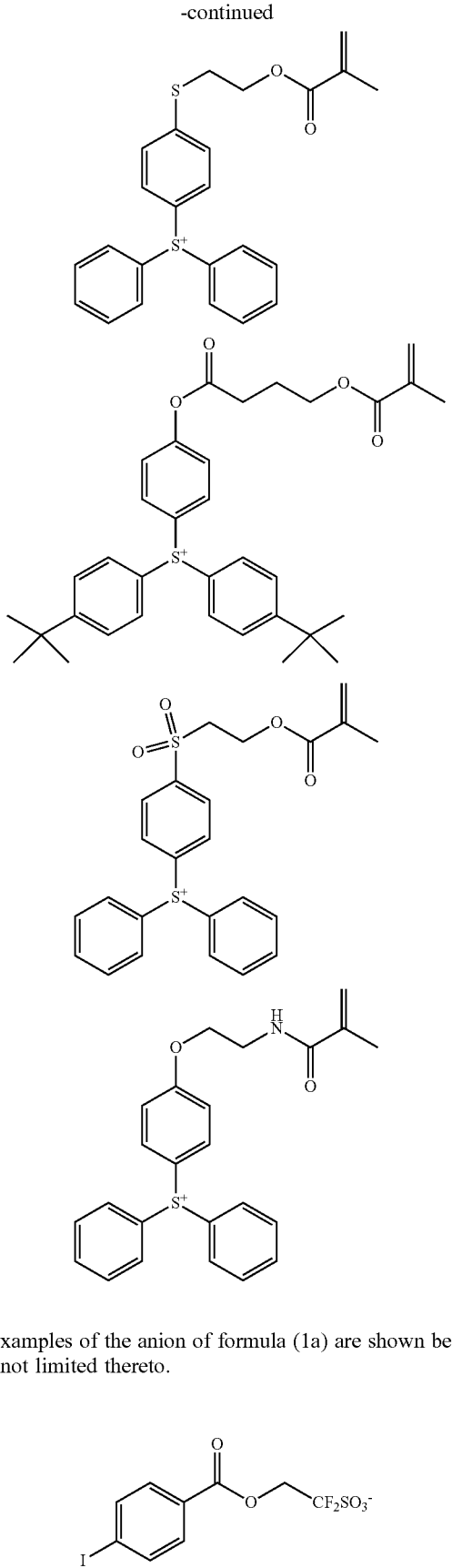
Examples of the anion of formula (1a) are shown below, but not limited thereto.
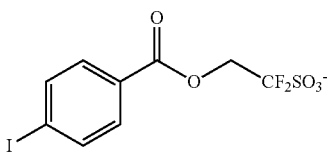

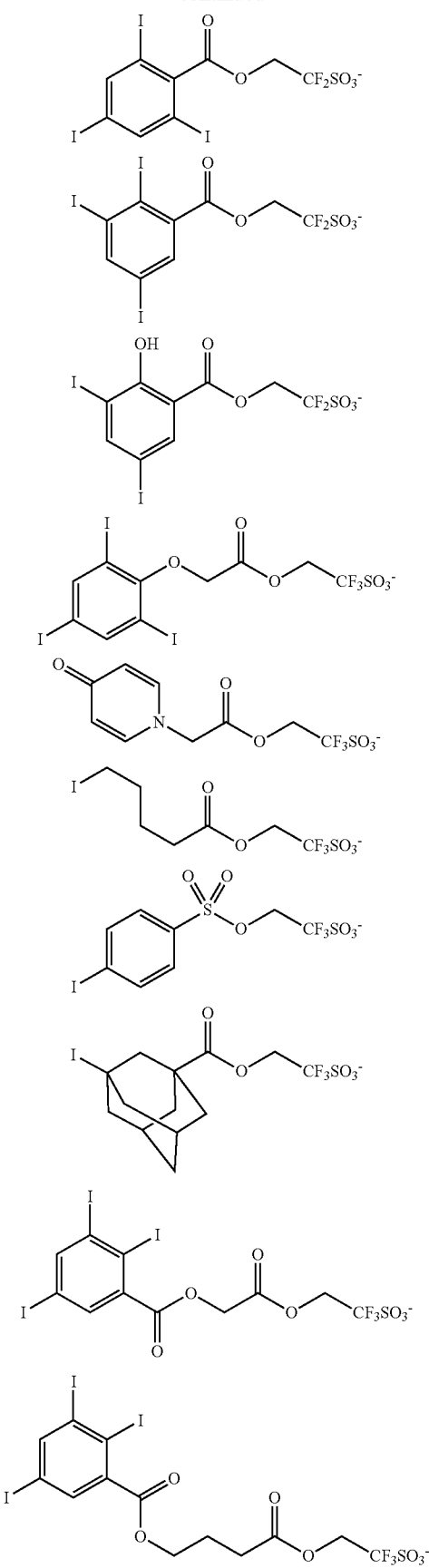
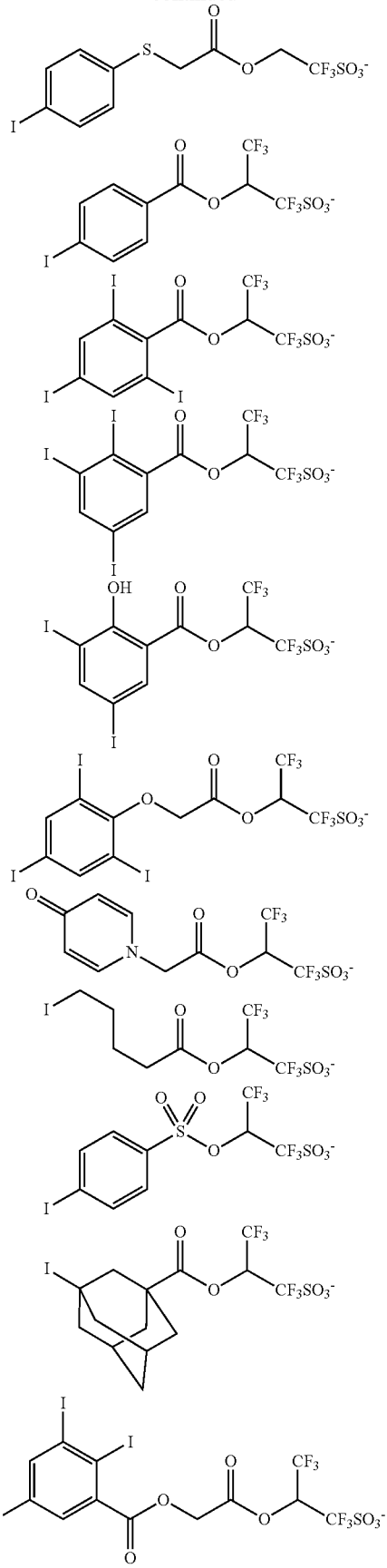

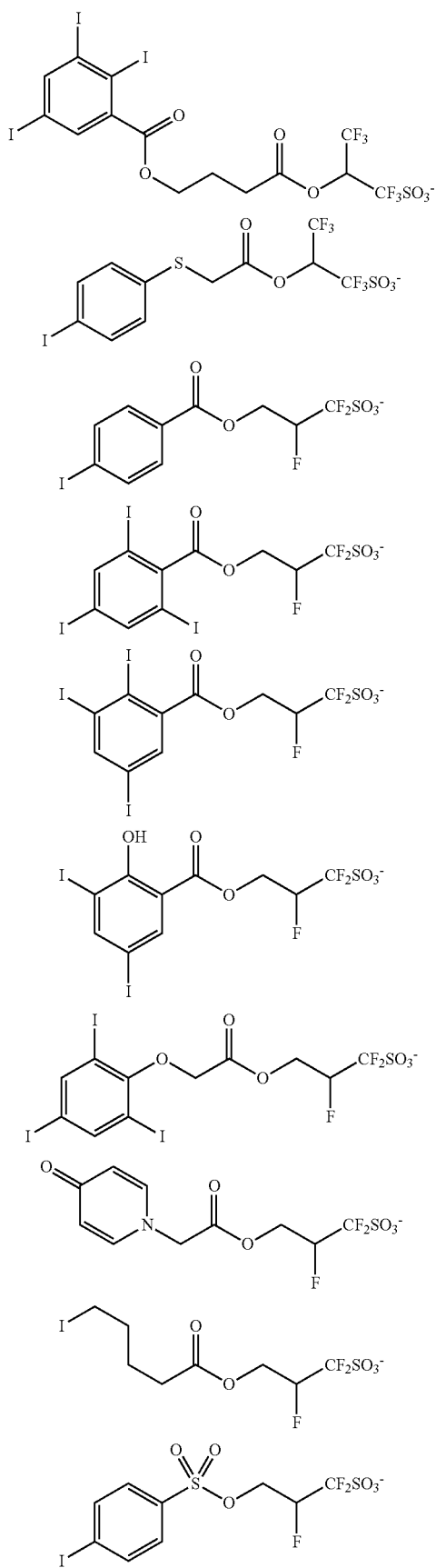
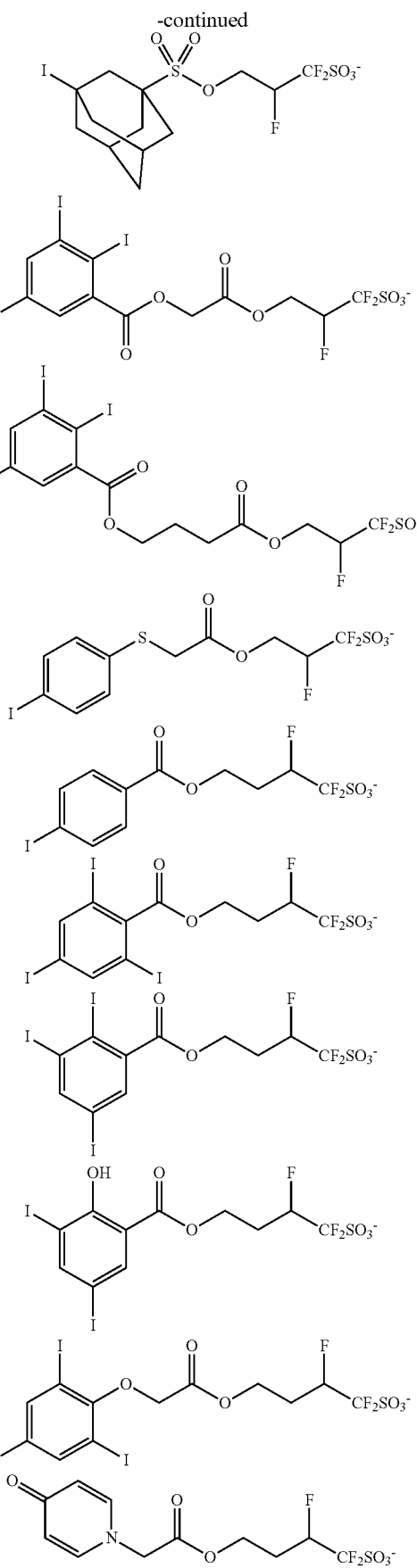

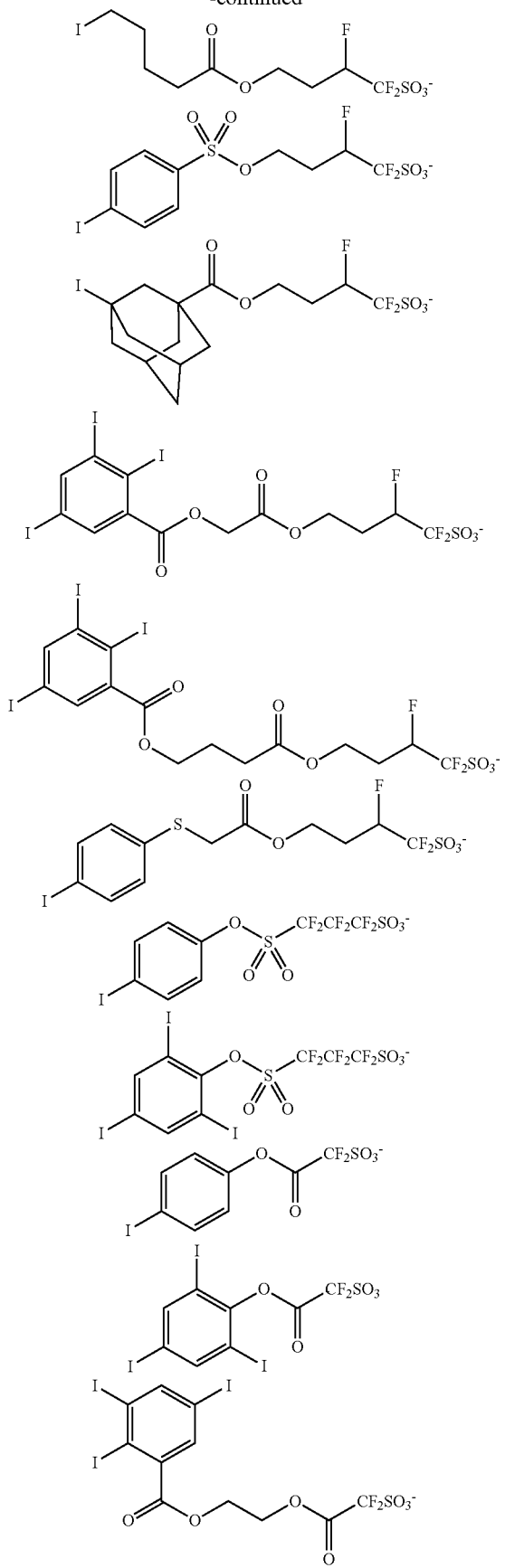
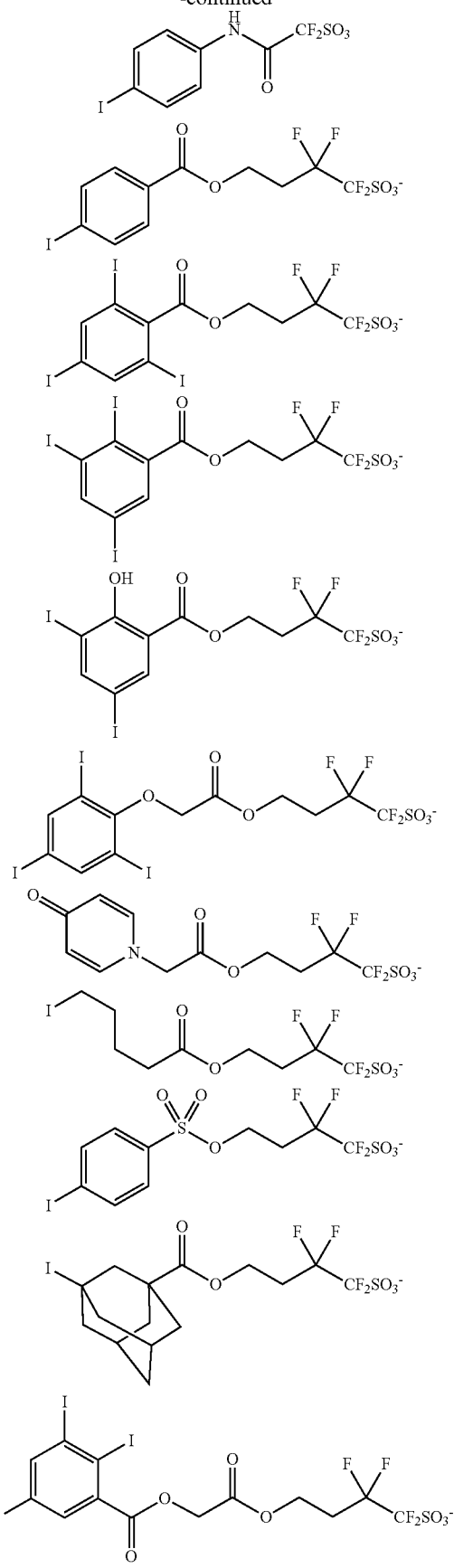

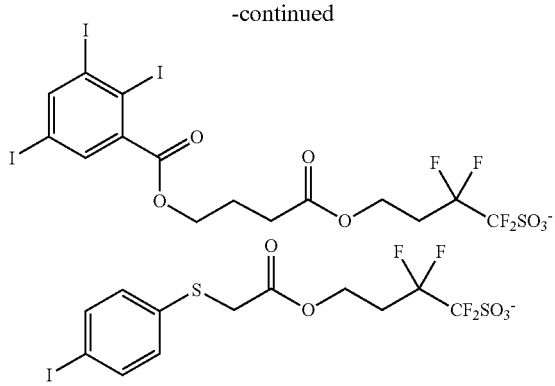

Exemplary sulfonium salts include combinations of any of the above-exemplified cations with any of the above-exemplified anions, but are not limited thereto.

The sulfonium salt may be synthesized by a combination of well-known organic chemistry procedures. For example, the desired compound may be obtained by reacting an α,α-difluorosulfonic acid salt having a modifiable functional group such as hydroxyl or carboxyl with an iodized compound to construct an anion structure, and then subjecting the reaction product to ion exchange reaction with the desired cation. Exemplary of the sulfonic acid salt serving as an anion-providing reactant is benzyltrimethylammonium 1,1,3,3,3-pentafluoro-2-hydroxypropane-1-sulfonate described, for example, in JP-A 2012-107151. With respect to the ion exchange reaction, reference is made to JP-A 2007-145797, for example.

The sulfonium salt is characterized by the presence of iodine atom in the anion moiety. The salt has the advantage of suppressed acid diffusion because of the large atomic weight of iodine. Since iodine is highly absorptive to EUV of wavelength 13.5 nm, it generates secondary electrons during exposure, contributing to a higher sensitivity. These enables to construct a resist material having a high sensitivity, reduced LWR, and improved CDU. Preferably the number of iodine atoms in the anion is 2 or more.

Since the sulfonium salt includes a cation moiety having a polymerizable group, it is a useful reactant for forming a base polymer in a resist composition. When a photoacid generator is bound in the base polymer, diffusion of the generated acid is substantially controlled. Lithography performance of high level is achievable due to the effect of the PAG-bound base polymer, combined with the presence of iodine atom. By virtue of the absorptivity of iodine, the resist composition exerts a significant effect, particularly when combined with EUV lithography. The resist composition is also effective in ArF and KrF lithography because of extremely suppressed acid diffusion.

The sulfonium salt exerts LWR reducing and CDU improving effects, which stand good either in positive and negative tone pattern formation by alkaline aqueous solution development or in negative tone pattern formation by organic solvent development.

Polymer

Another embodiment is a polymer comprising recurring units derived from the sulfonium salt. Specifically, the recurring units derived from a sulfonium salt containing a cation having the formula (1b-1) or (1c-1) are represented by the following formula (1b-1-1) or (1c-1-1).

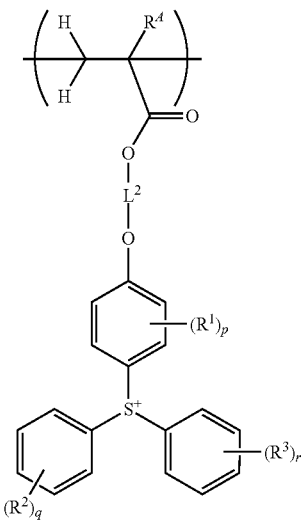

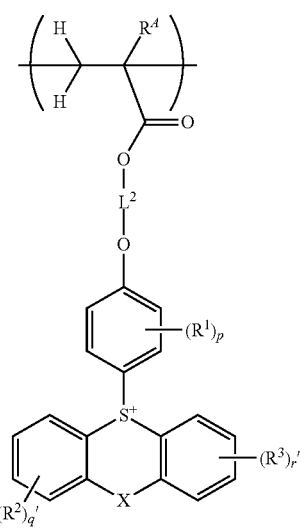

Herein $R^4$, $R^1$, $R^2$, $R^3$, $L^2$, p, q, r, q' and r' are as defined above.

Preferably the polymer further comprises recurring units having the formula (a), (b) or (c).

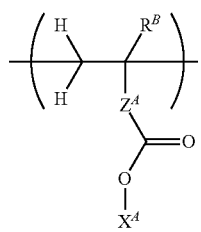

-continued

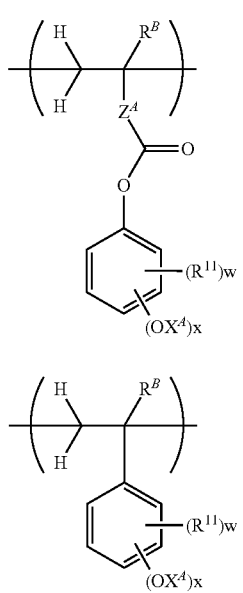

Herein $R^B$ is hydrogen, fluorine, methyl or trifluoromethyl. $Z^A$ is a single bond, phenylene group, naphthylene group or (backbone)-C(=O)—O—$Z^B$—, wherein $Z^B$ is a $C_1$-$C_{10}$ straight, branched or cyclic alkylene group which may contain a hydroxyl, ether bond, ester bond or lactone ring, or a phenylene or naphthylene group, $X^A$ is an acid labile group. $R^{11}$ is halogen, nitro, cyano, or a $C_1$-$C_{20}$ straight, branched or cyclic monovalent hydrocarbon group which may contain a heteroatom, w is an integer of 0 to 4, preferably 0 or 1, x is 1 or 2, preferably 1, and $1 \leq w+x \leq 5$.

Examples of the structure having formula (a) wherein $Z^A$ is a variant are shown below, but not limited thereto.

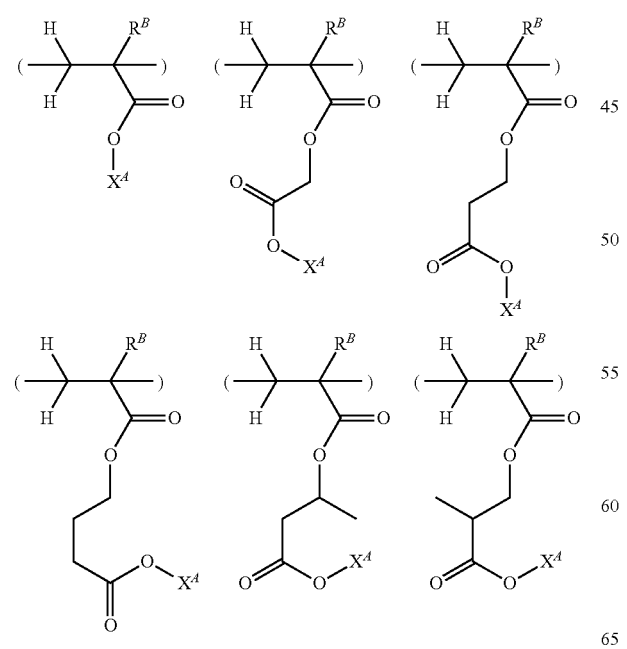

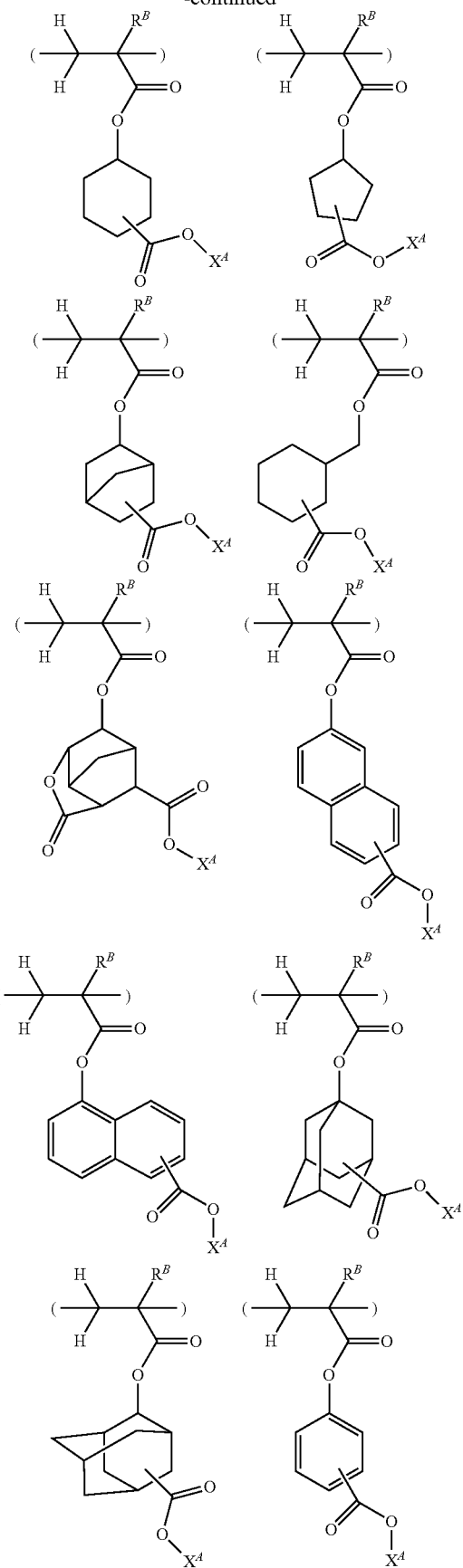

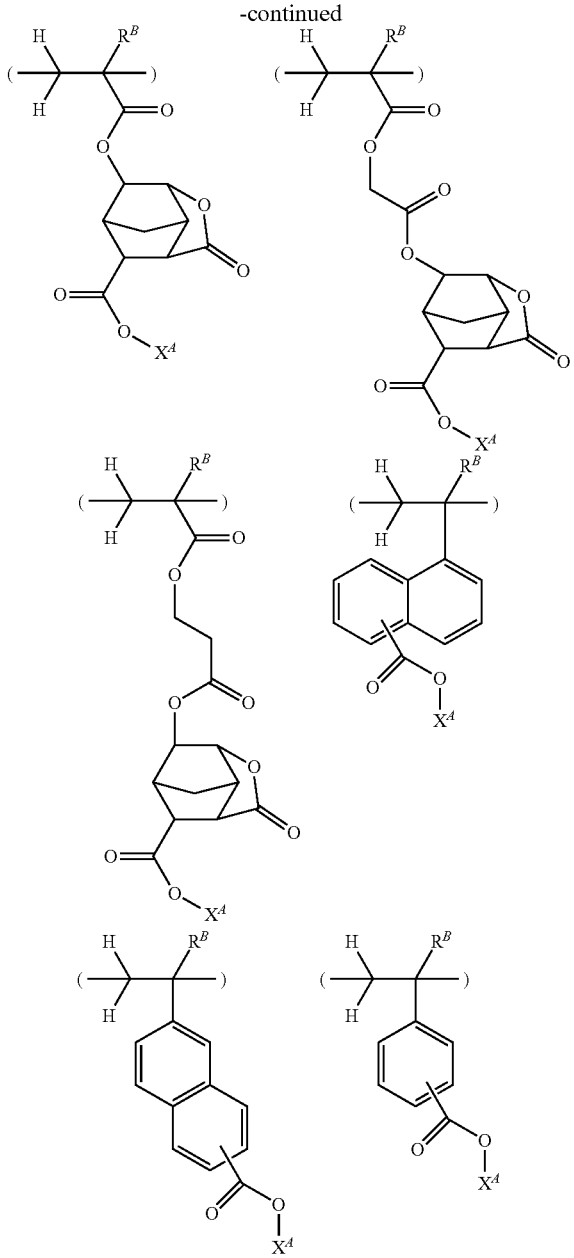
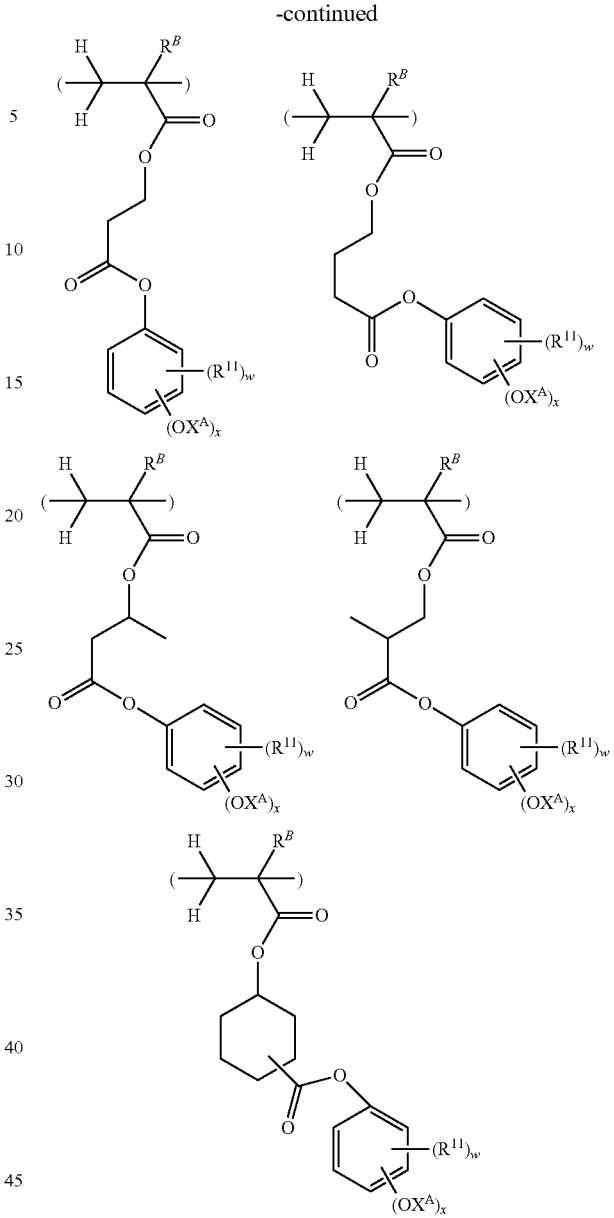
Examples of the structure having formula (b) wherein $Z^A$ is a variant are shown below, but not limited thereto.
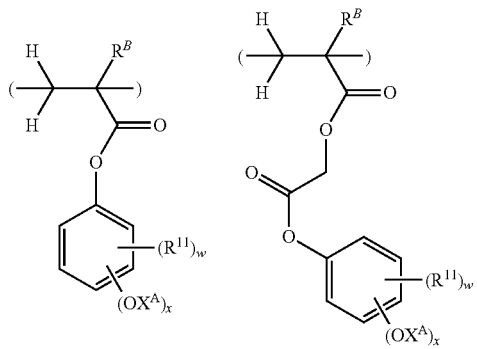
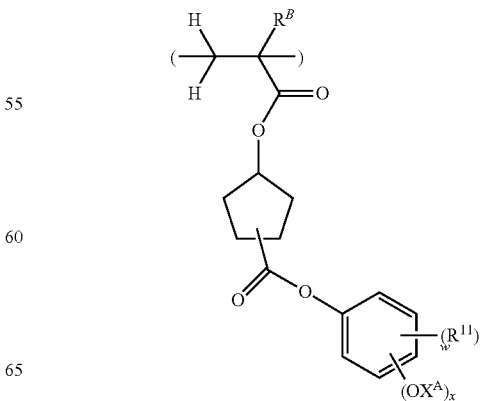

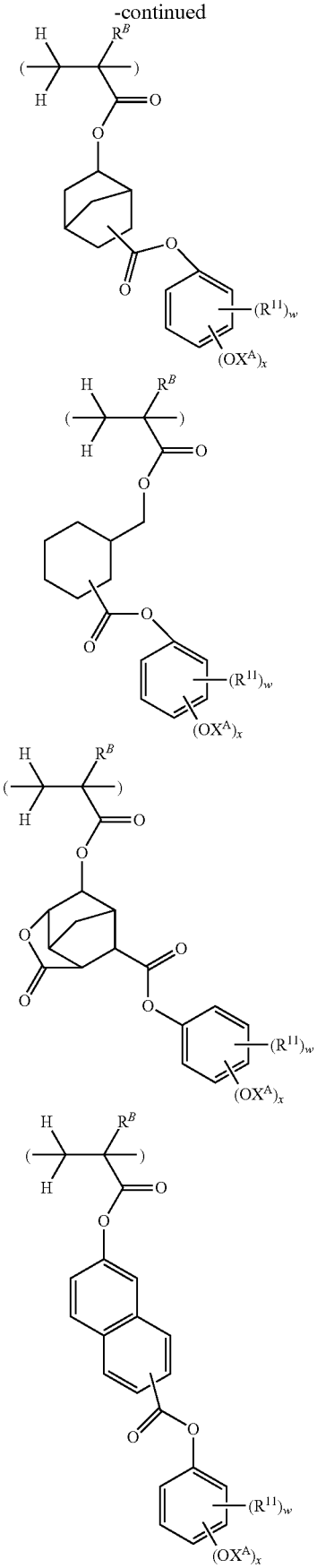
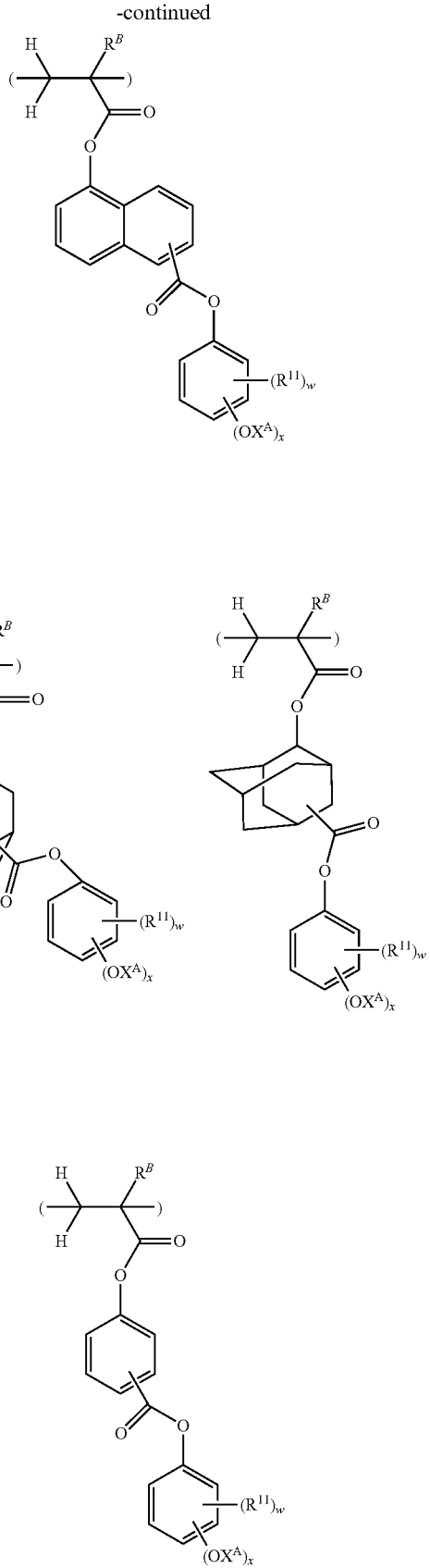

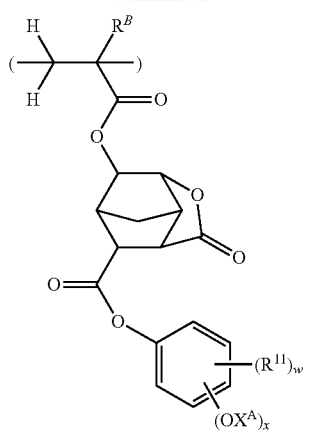
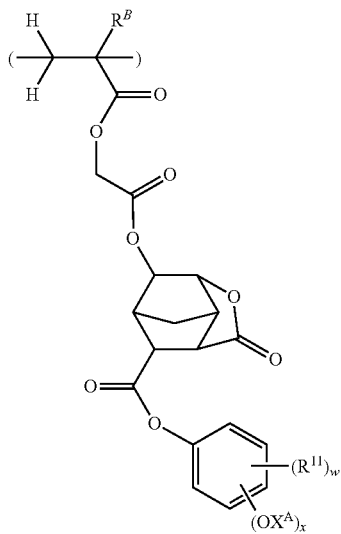
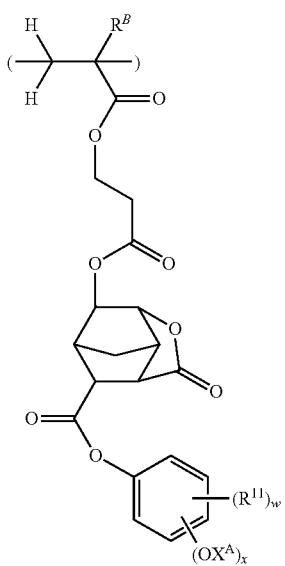

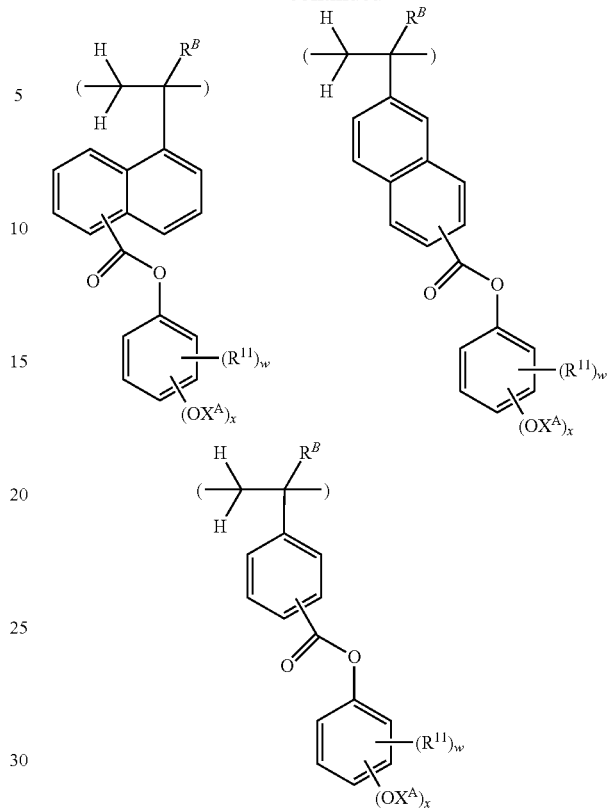

The acid labile group $X^A$ may be selected from a variety of such groups. Examples of the acid labile group are groups of the following formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

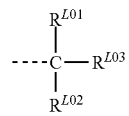 (L1)

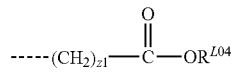 (L2)

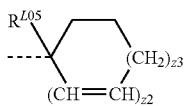 (L3)

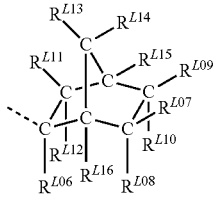 (L4)

In formula (L1), $R^{L01}$ and $R^{L02}$ each are hydrogen or a straight, branched or cyclic alkyl group of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl and adamantyl.

$R^{L03}$ is a monovalent hydrocarbon group of 1 to 18 carbon atoms, preferably 1 to 10 carbon atoms, which may contain a hetero atom such as oxygen. Examples include straight, branched or cyclic alkyl groups, substituted forms of such alkyl groups in which one or more hydrogen atoms are replaced by hydroxyl, alkoxy, oxo, amino, alkylamino or the like, and substituted forms of such alkyl groups in which a heteroatom such as oxygen intervenes between carbon atoms. Illustrative examples of the alkyl group are as exemplified above for $R^{L01}$ and $R^{L02}$. Illustrative examples of the substituted alkyl groups are shown below.

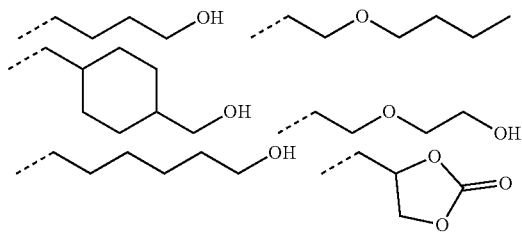

A pair of $R^{L01}$ and $R^{L02}$, $R^{L01}$ and $R^{L03}$, or $R^{L02}$ and $R^{L03}$ may bond together to form a ring with the carbon atom and oxygen atom to which they are attached. Ring-forming participants of $R^{L01}$, $R^{L02}$ and $R^{L03}$ represent a straight or branched alkylene group of 1 to 18 carbon atoms, preferably 1 to 10 carbon atoms.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-pentyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, -ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter z1 is an integer of 0 to 6.

In formula (L3), $R^{L05}$ is an optionally substituted $C_1$-$C_8$ straight, branched or cyclic alkyl group or an optionally substituted $C_6$-$C_{20}$ aryl group. Examples of the optionally substituted alkyl group include straight, branched or cyclic alkyl groups such as methyl, ethyl, propyl, isopropyl, n-butyl, sec-butyl, tert-butyl, tert-pentyl, n-pentyl, n-hexyl, cyclopentyl, cyclohexyl and substituted forms of the foregoing in which one or more hydrogen is substituted by a hydroxyl, alkoxy, carboxy, alkoxycarbonyl, oxo, amino, alkylamino, cyano, mercapto, alkylthio, or sulfo moiety. Examples of the optionally substituted aryl group include phenyl, methylphenyl, naphthyl, anthryl, phenanthryl, pyrenyl, and substituted forms of the foregoing in which one or more hydrogen is substituted by a hydroxyl, alkoxy, carboxy, alkoxycarbonyl, oxo, amino, alkylamino, cyano, mercapto, alkylthio, or sulfo moiety. Letter z2 is equal to 0 or 1, z3 is an integer of 0 to 3, and 2xz2+z3 is equal to 2 or 3.

In formula (L4), $R^{L06}$ is an optionally substituted $C_1$-$C_8$ straight, branched or cyclic alkyl group or an optionally substituted $C_6$-$C_{20}$ aryl group. Examples of the alkyl and aryl groups are the same as exemplified for $R^{L05}$.

$R^{L07}$ to $R^{L16}$ are each independently hydrogen, or an optionally substituted $C_1$-$C_{15}$ monovalent hydrocarbon group. Exemplary monovalent hydrocarbon groups are straight, branched or cyclic alkyl groups such as methyl, ethyl, propyl, isopropyl, n-butyl, sec-butyl, tert-butyl, tert-pentyl, n-pentyl, n-hexyl, n-octyl n-nonyl, n-decyl, cyclopentyl, cyclohexyl, cyclopentylmethyl, cyclopentylethyl, cyclopentylbutyl, cyclohexytmethyl, cyclohexylethyl and cyclohexylbutyl, and substituted forms of the foregoing groups in which one or more hydrogen is replaced by hydroxyl, alkoxy, carboxy, alkoxycarbonyl, oxo, amino, alkylamino, cyano, mercapto, alkylthio, sulfo or the like. Alternatively, two of $R^{L07}$ to $R^{L16}$, taken together, form a ring with the carbon atom to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R_{L13}$ and $R^{L14}$, or a similar pair). Ring-forming participants of $R^{L07}$ to $R^{L16}$ represent a $C_1$-$C_{15}$ divalent hydrocarbon group. Examples of the divalent hydrocarbon group are as exemplified above for the monovalent hydrocarbon groups, with one hydrogen atom being to eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, $R^{L14}$ and $R^{L15}$, or a similar pair).

Of the acid labile groups of formula (L1), the straight and branched ones are exemplified by the following, but not limited thereto.

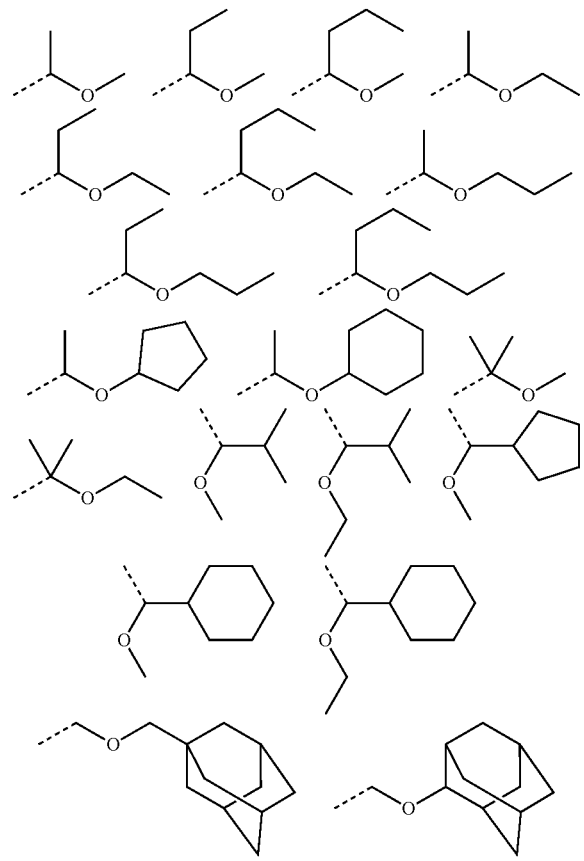

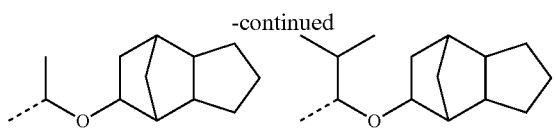

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl tert-pentyloxycarbonyl, tert-pentyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Examples of the acid labile 2groups of formula (L3) include 1-methylcyclopentyl, 1-ethylcyclopentyl, 1-n-propylcyclopentyl, 1-isopropylcyclopentyl, 1-n-butylcyclopentyl, 1-sec-butyleyclopentyl, 1-cyclohexylcyclopentyl, 1-(4-metboxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Preferably the acid labile groups of formula (L4) are groups having the following formulae (L4-1) to (L4-4).

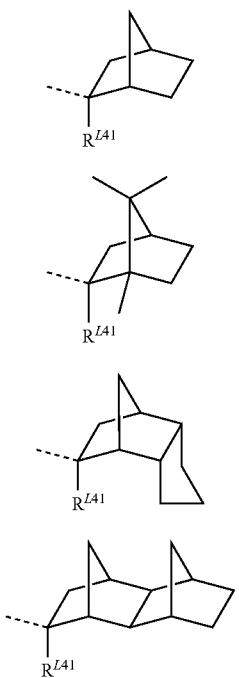

In formulae (L4-1) to (L4-4), the broken line denotes a bonding site and direction. $R^{L41}$ is each independently a monovalent hydrocarbon group, typically $C_1$-$C_{10}$ straight, branched or cyclic alkyl group, such as methyl, ethyl, propyl, isopropyl, n-butyl, sec-butyl, tert-butyl, tert-pentyl, n-pentyl, n-hexyl, cyclopentyl or cyclohexyl.

For the groups having formulae (L4-1) to (L4-4), there can exist stereoisomers (enantiomers or diastereomers). Each of formulae (L4-1) to (L4-4) collectively represents all such stereoisomers. Plural stereoisomers may be included when $X^A$ is an acid labile group having formula (L4).

For example, the formula (L4-3) represents one or a mixture of two selected from groups having the following formulae (L4-3-1) and (L4-3-2).

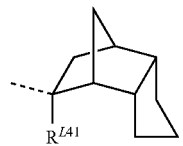

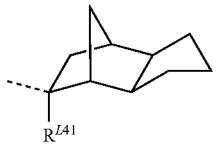

Herein $R^{L41}$ is as defined above.

Similarly, the formula (L4-4) represents one or a mixture of two or more selected from groups having the following formulas (L4-4-1) to (L4-4-4).

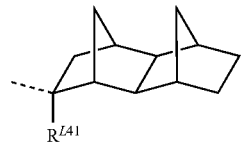

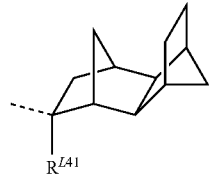

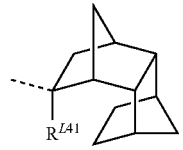

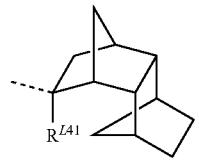

Herein $R^{L41}$ is as defined above.

Each of formulae (L4-1) to (L4-4), (L4-3-1) and (L4-3-2), and (L4-4-1) to (L4-4-4) collectively represents an enantiomer thereof and a mixture of enantiomers.

It is noted that in the above formulae (L4-1) to (L4-4), (L4-3-1) and (L4-3-2), and (L4-4-1) to (L4-4-4), the bond direction is on the exo side relative to the bicyclo[2.2.1] heptane ring, which ensures high reactivity for acid catalyzed elimination reaction (see JP-A 2000-336121). In preparing these monomers having a tertiary exo-alkyl group of bicyclo[2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

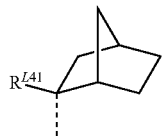
(L4-1-endo)

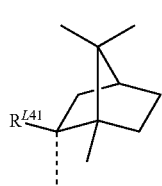
(L4-2-endo)

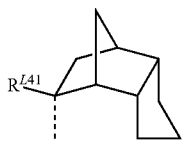
(L4-3-endo)

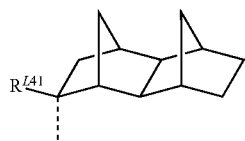
(L4-4-endo)

Herein $R^{L41}$ is as defined above.

Illustrative examples of the acid labile group of formula (L4) are given below, but not limited thereto.

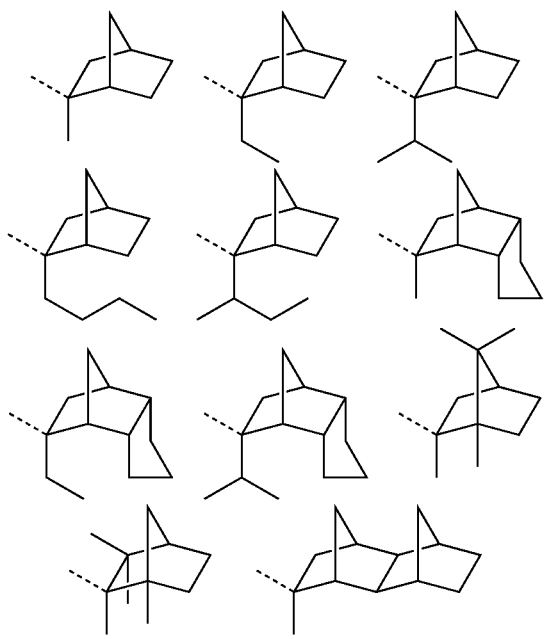

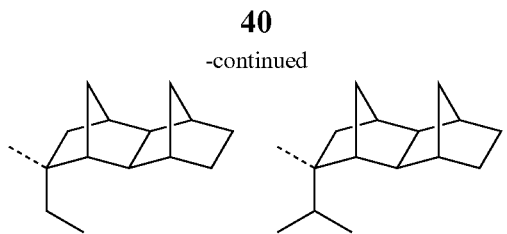

Examples of the tertiary $C_4$-$C_{20}$ alkyl groups, trialkylsilyl groups in which each alkyl moiety has 1 to 6 carbon atoms, and $C_4$-$C_{20}$ oxoalkyl groups, represented by $X^A$, are as exemplified for $R^{L04}$.

Under the action of acid, a polymer comprising recurring units of formula (a) is decomposed to generate a carboxyl group, turning alkaline soluble.

Examples of the recurring units of formula (a) are given below, but not limited thereto. Herein $R^B$ is as defined above.

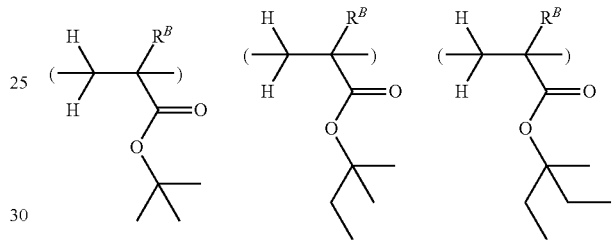

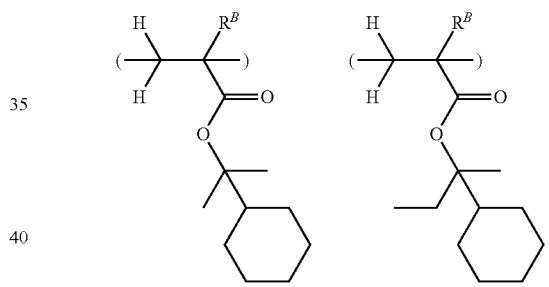

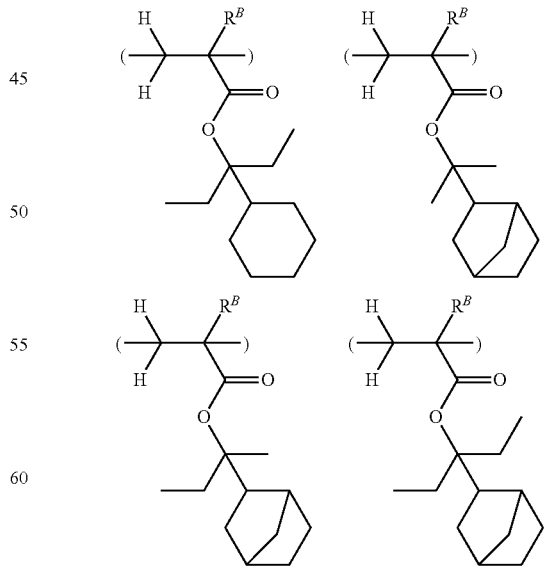

-continued
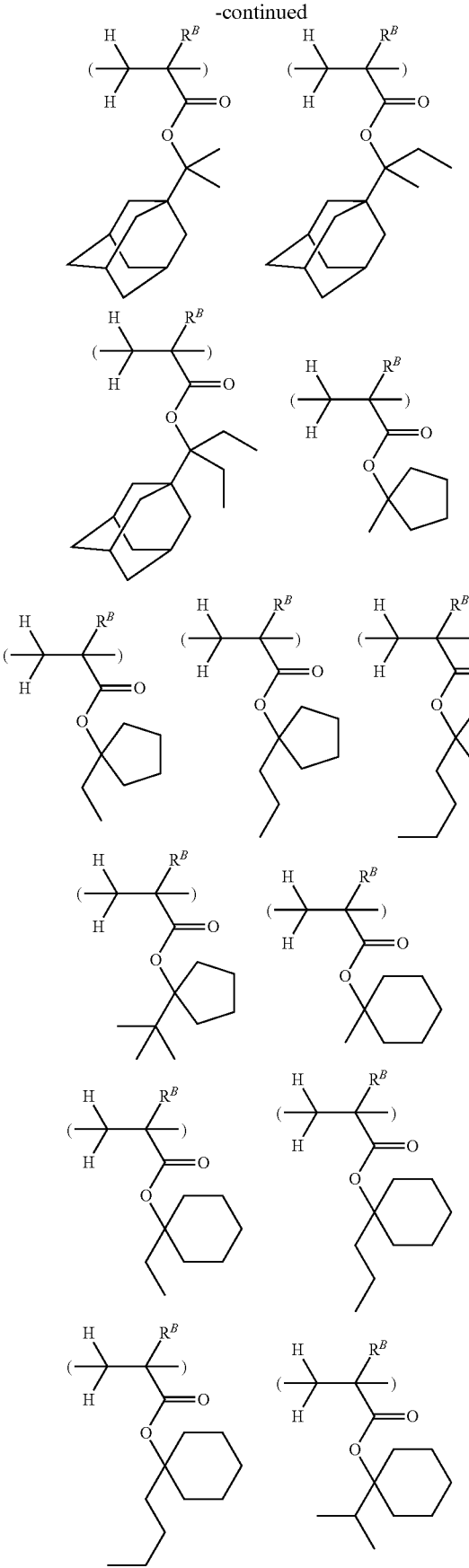
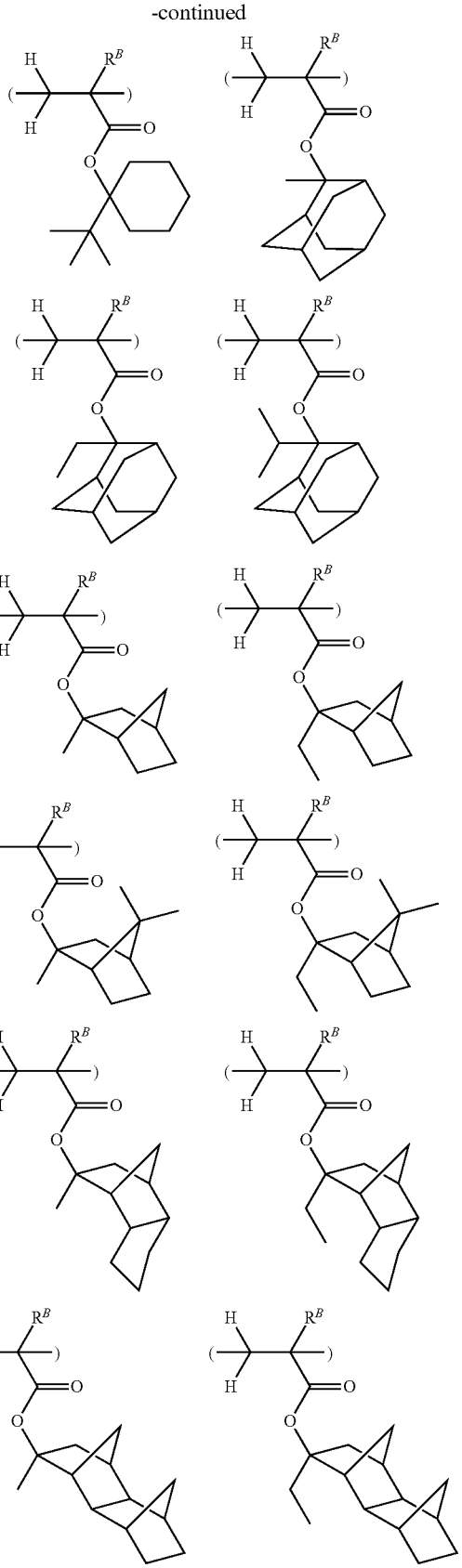

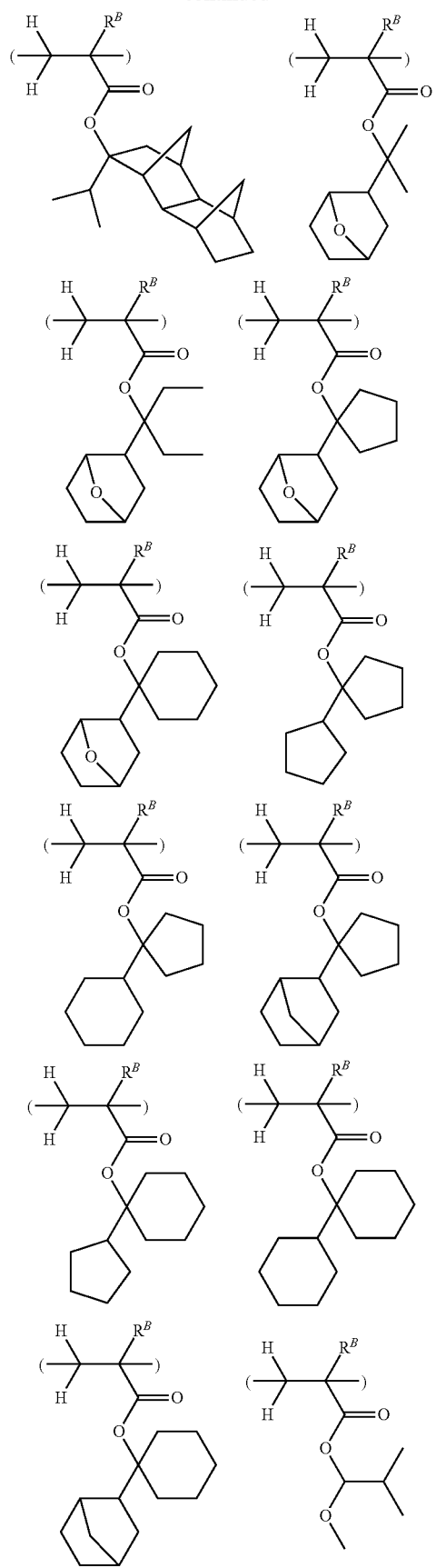
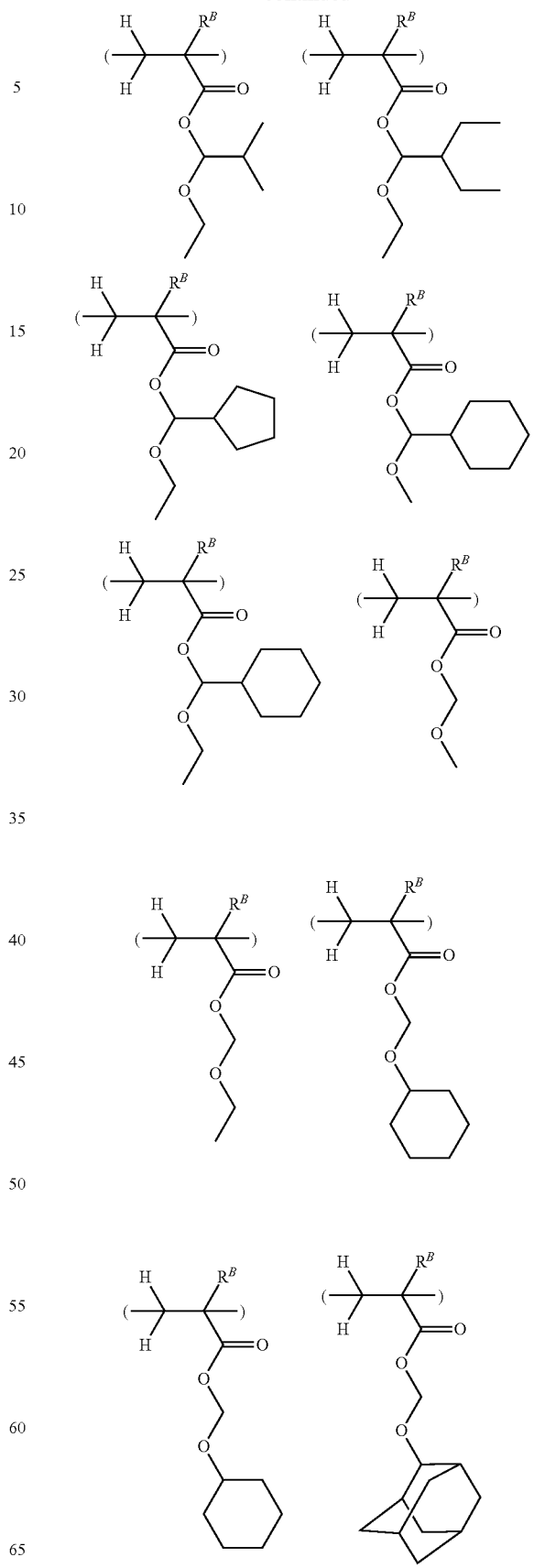

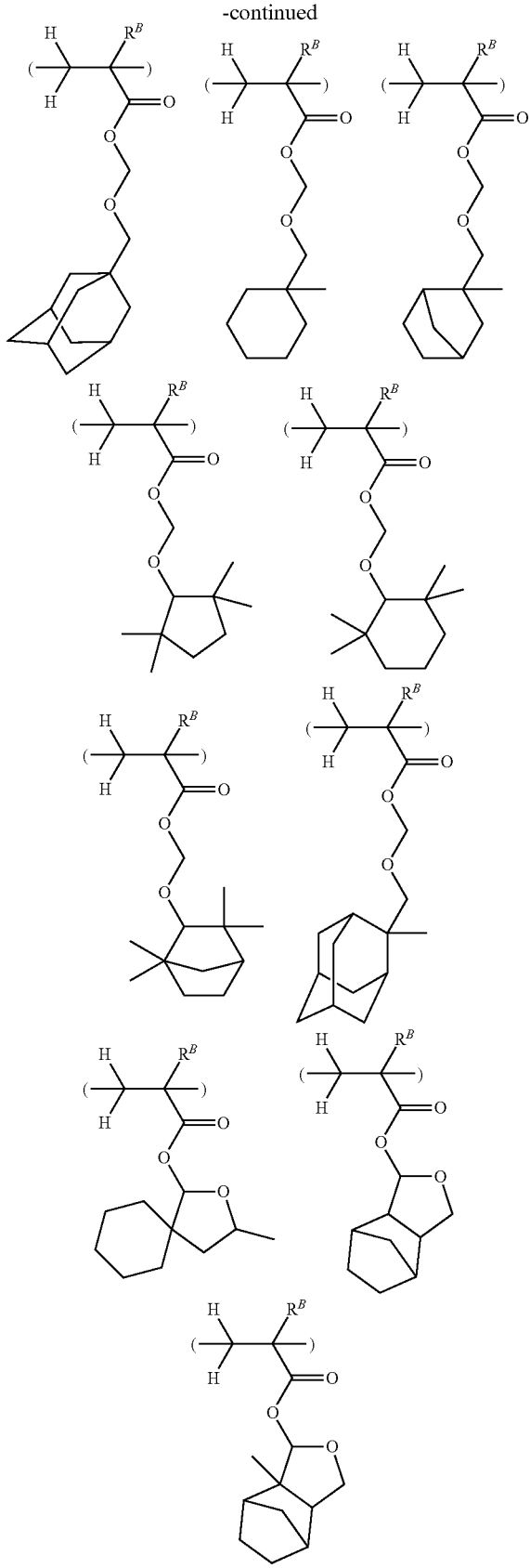

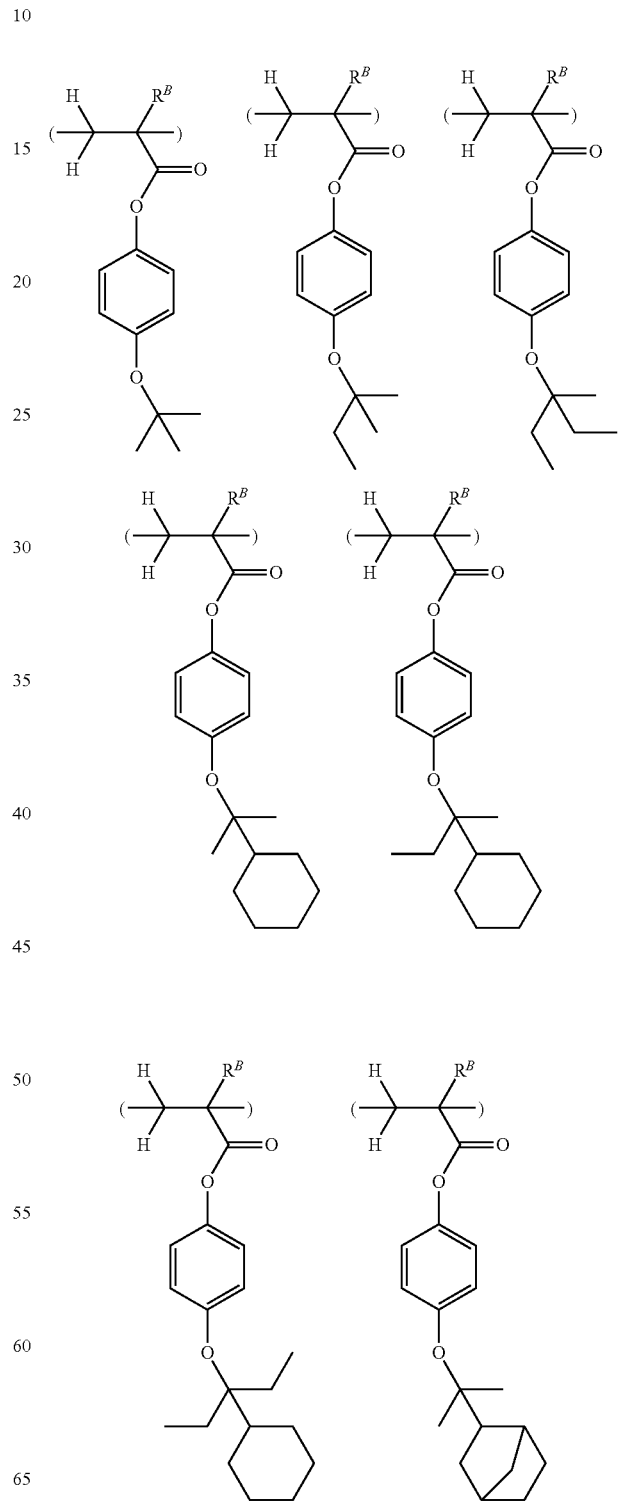

bond may be combined with similar acid labile groups. Examples of units wherein $Z^A$ is other than a single bond are substantially the same as illustrated above.

Under the action of acid, a polymer comprising recurring units of formula (b) or (c) is decomposed to generate a hydroxyl group, turning alkaline soluble.

Examples of the recurring units of formula (b) are given below, but not limited thereto. Herein $R^B$ is as defined above.

While the foregoing examples correspond to those units wherein $Z^A$ is a single bond, $Z^A$ which is other than a single

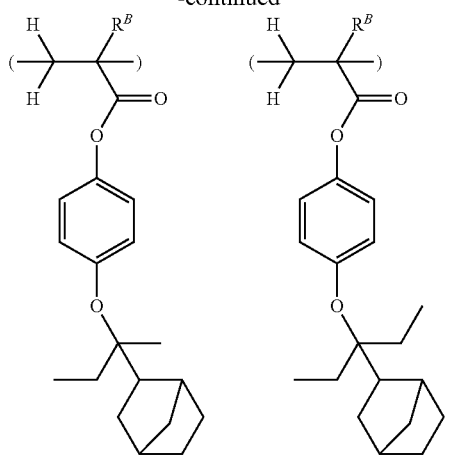
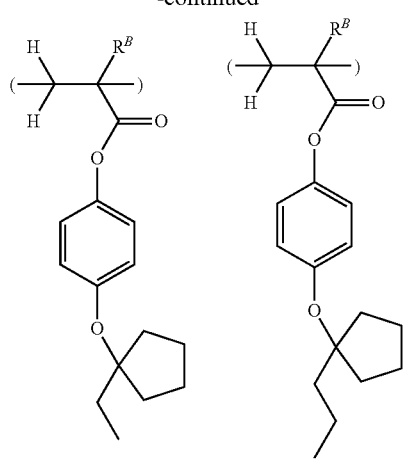
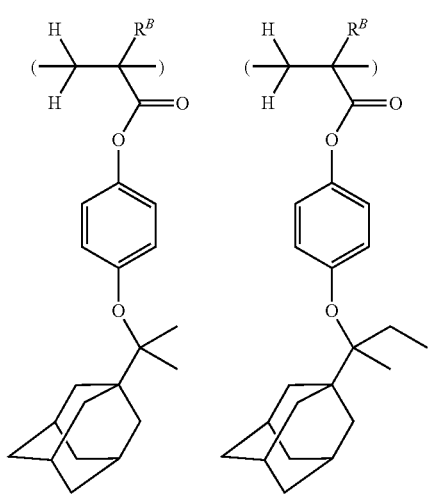
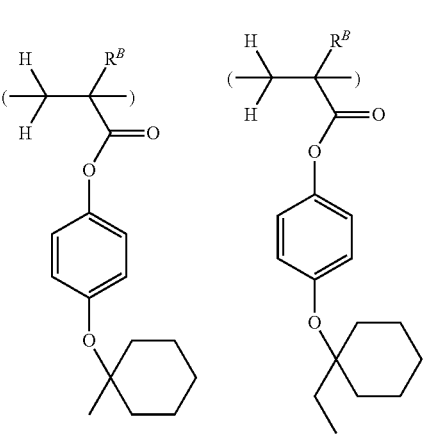
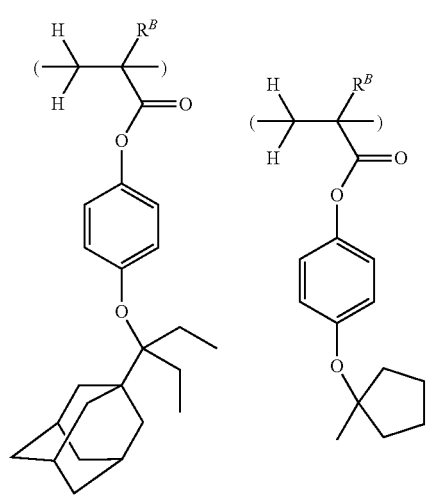

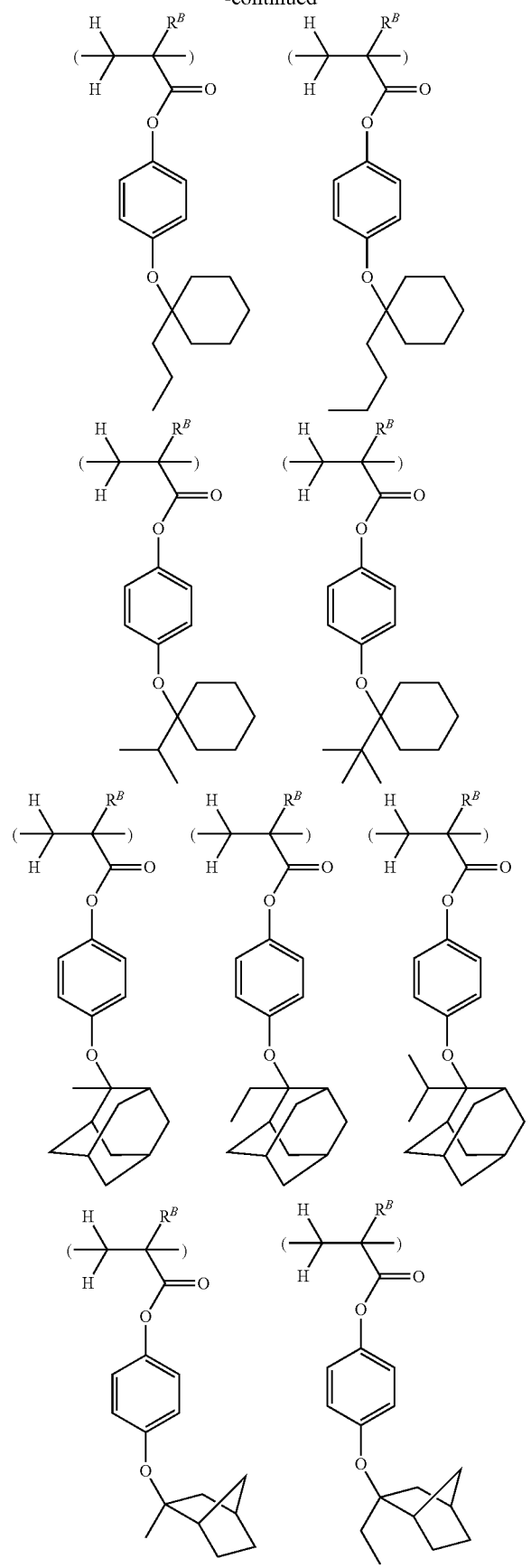
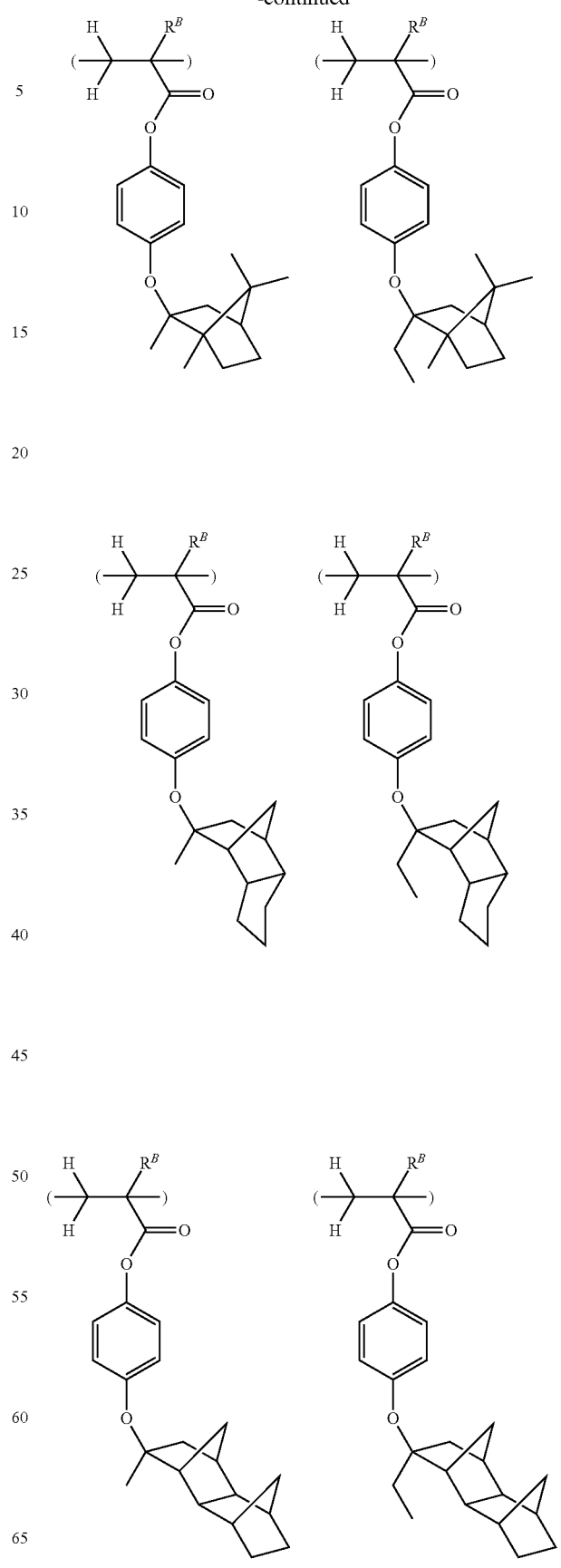

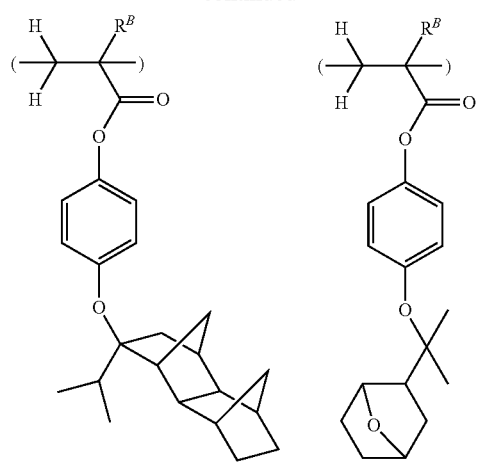
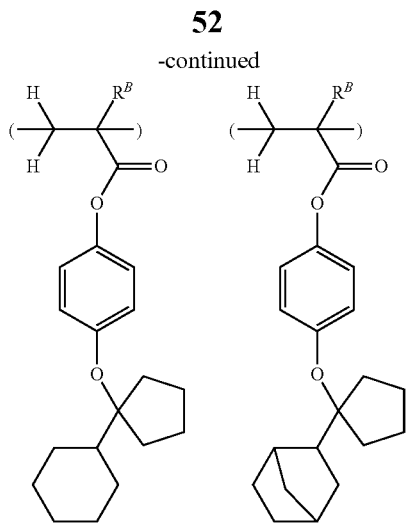
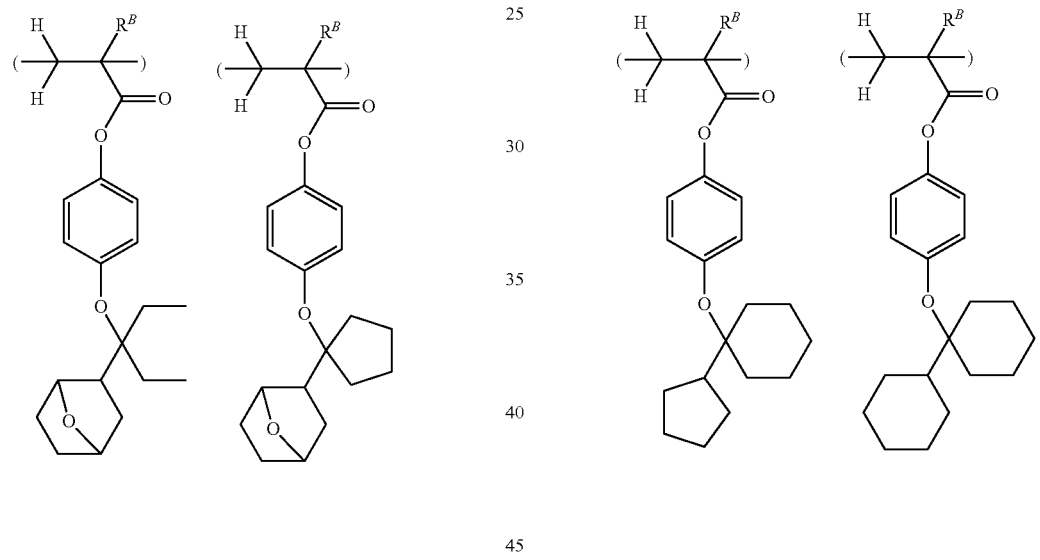
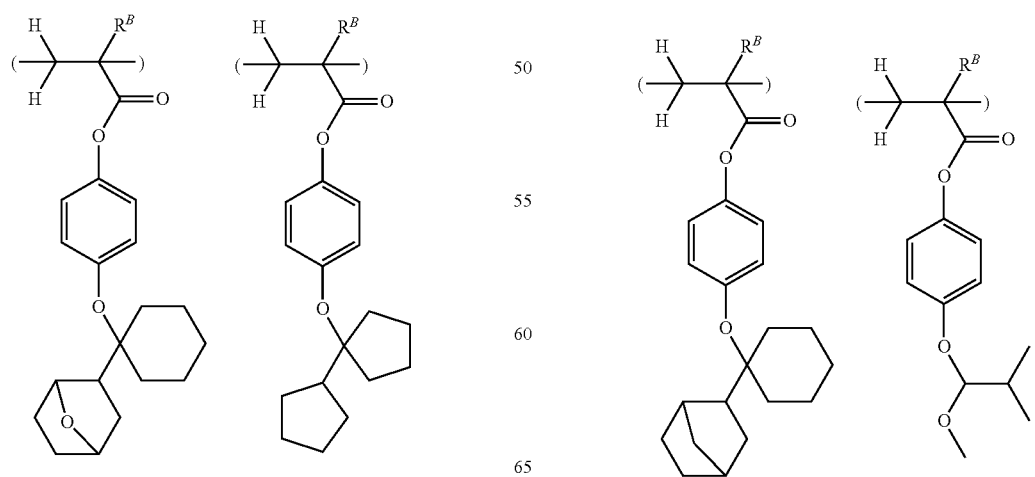

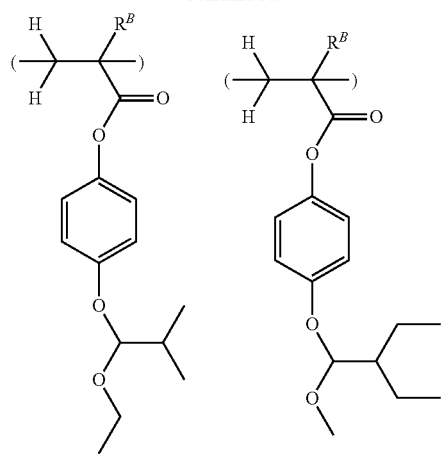
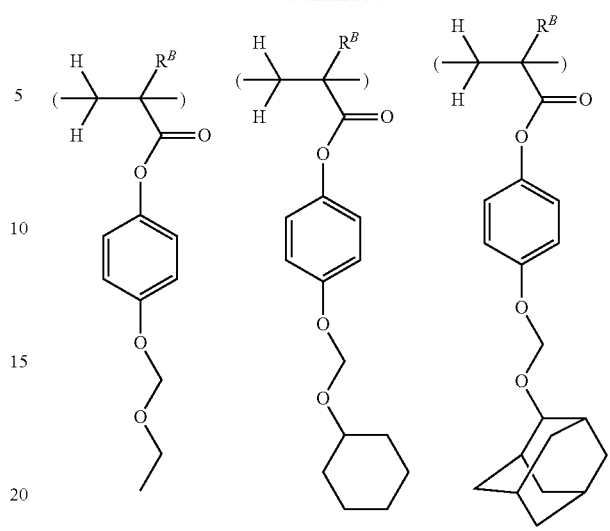
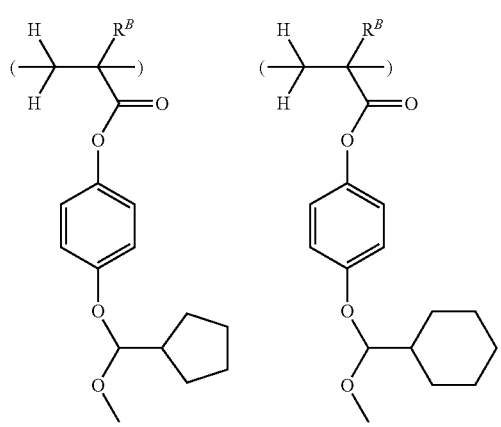
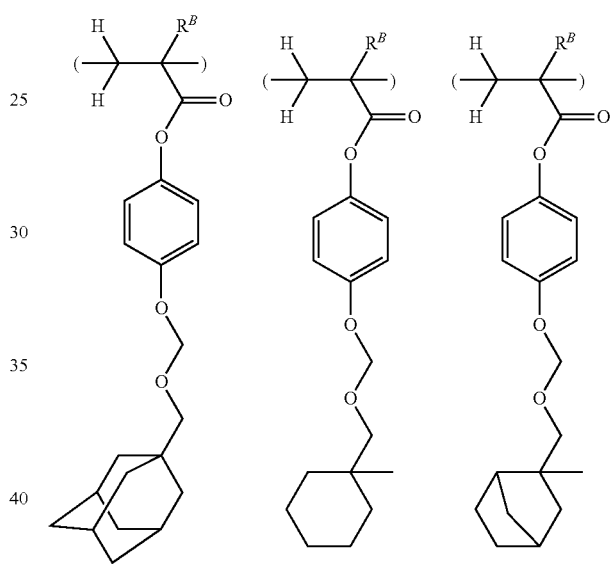
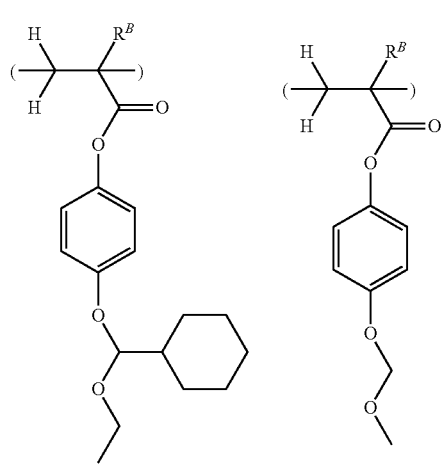
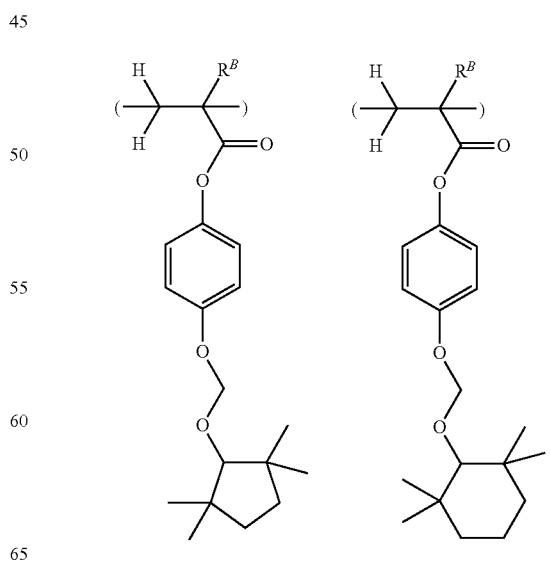

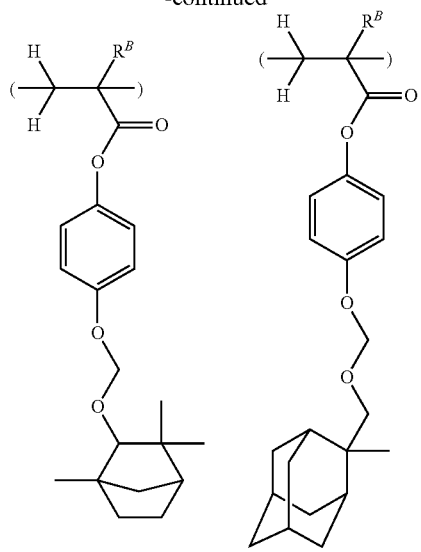
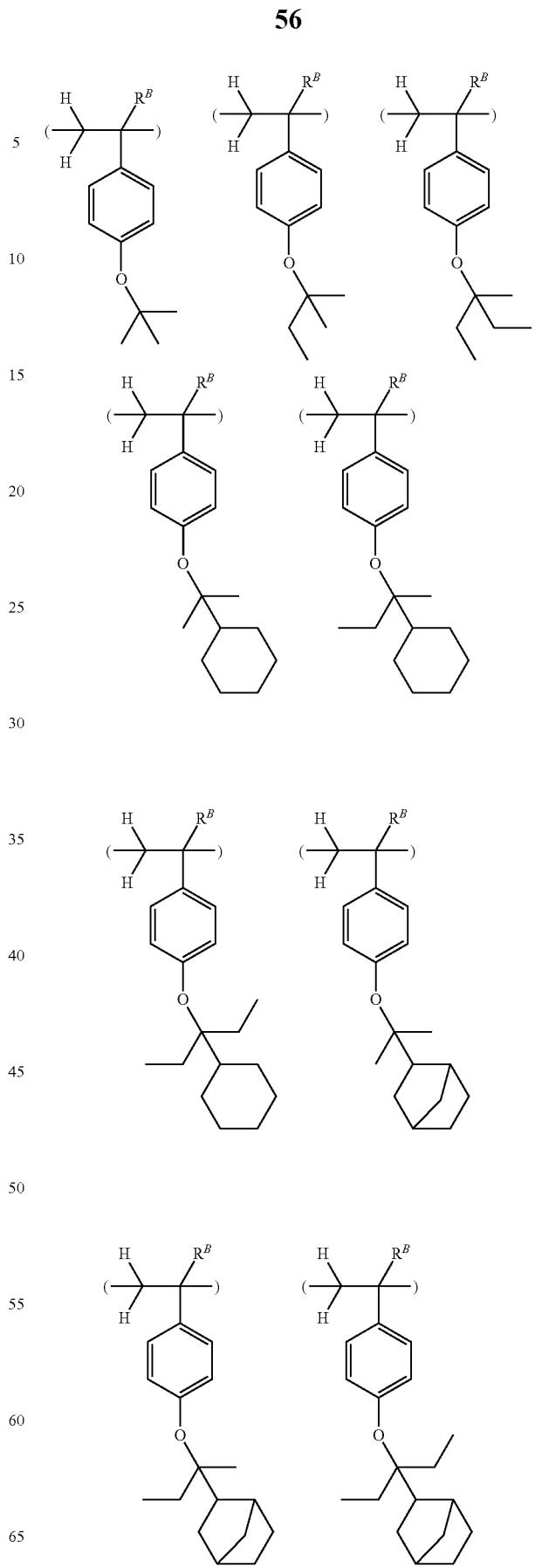
Examples of the recurring units of formula (c) are given below, but not limited thereto. Herein $R^B$ is as defined above.

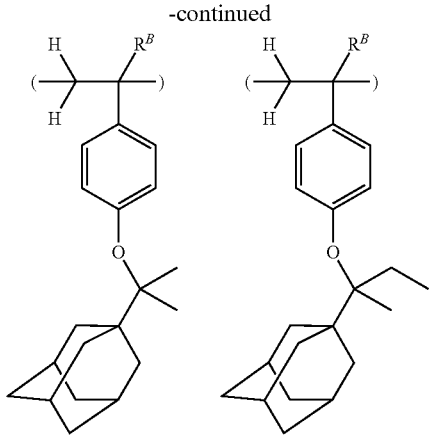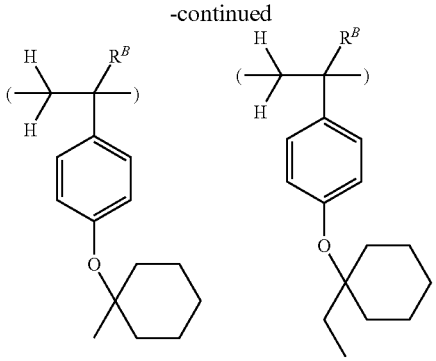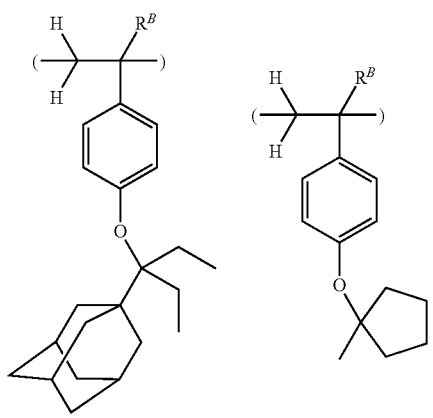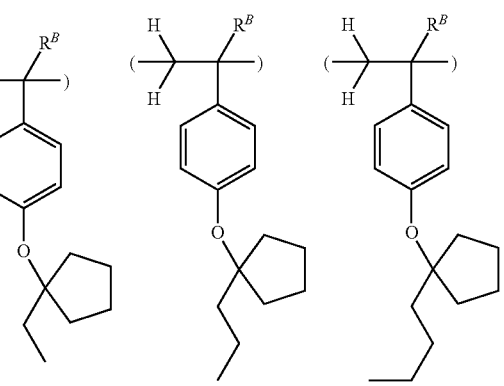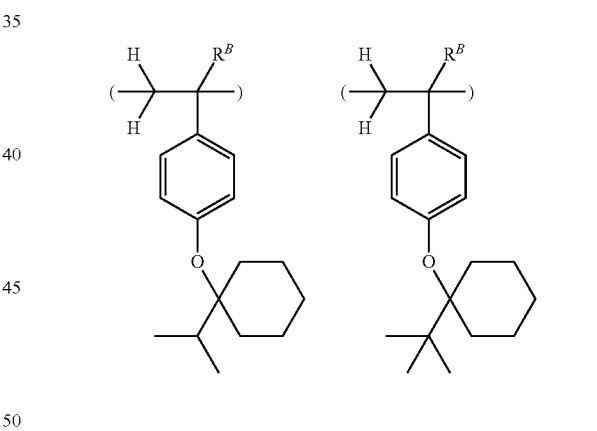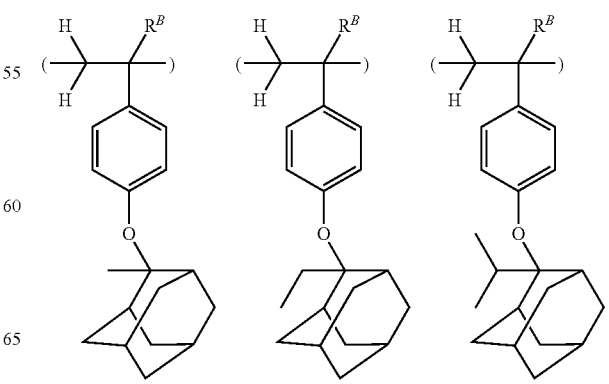

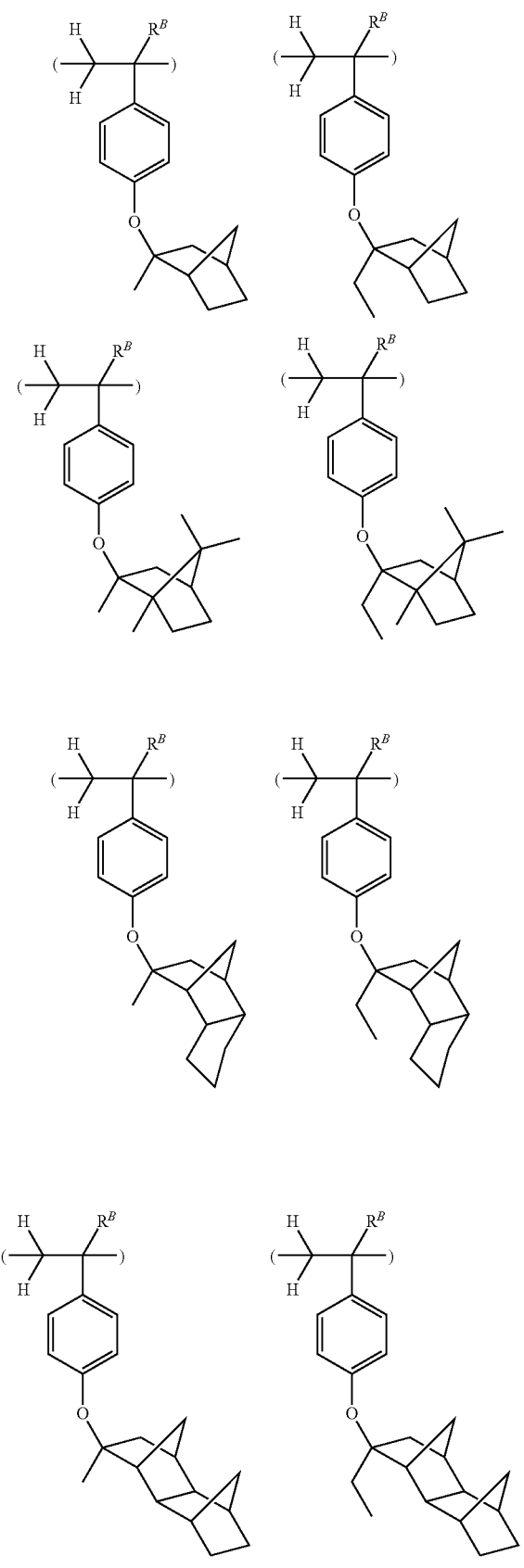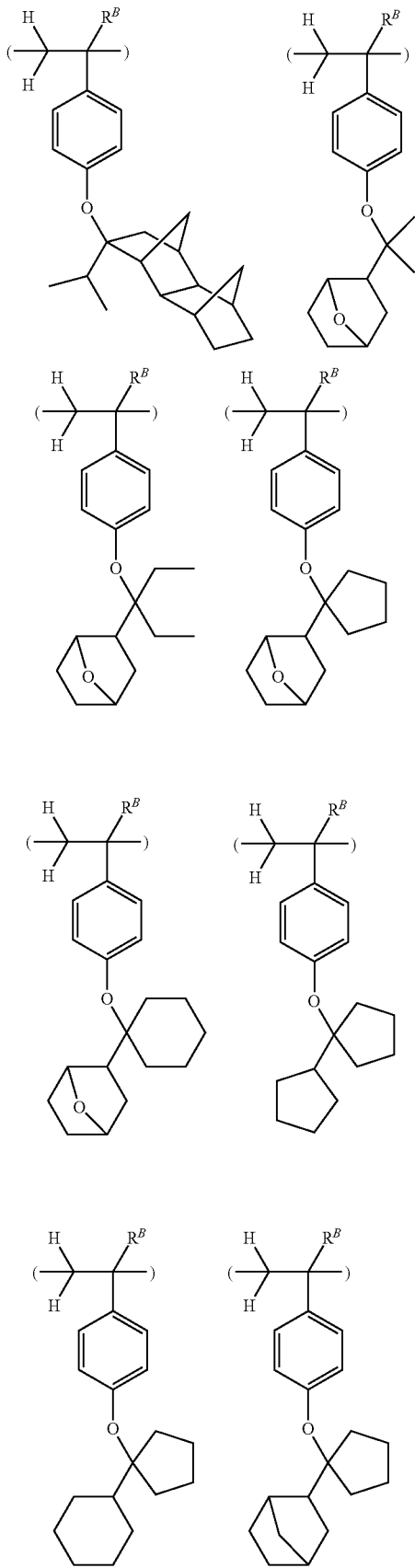

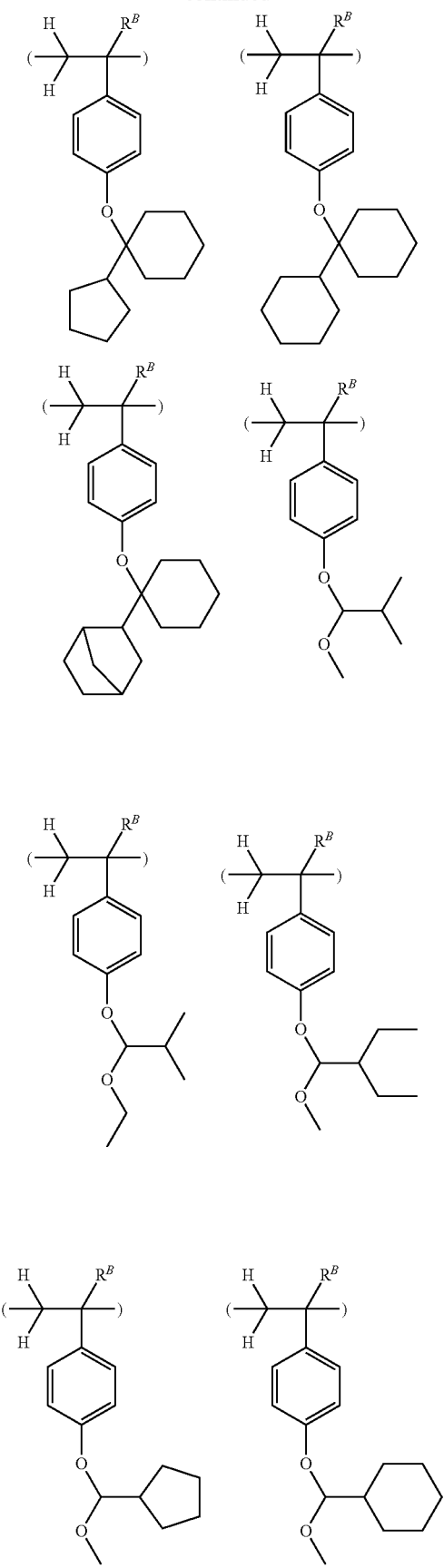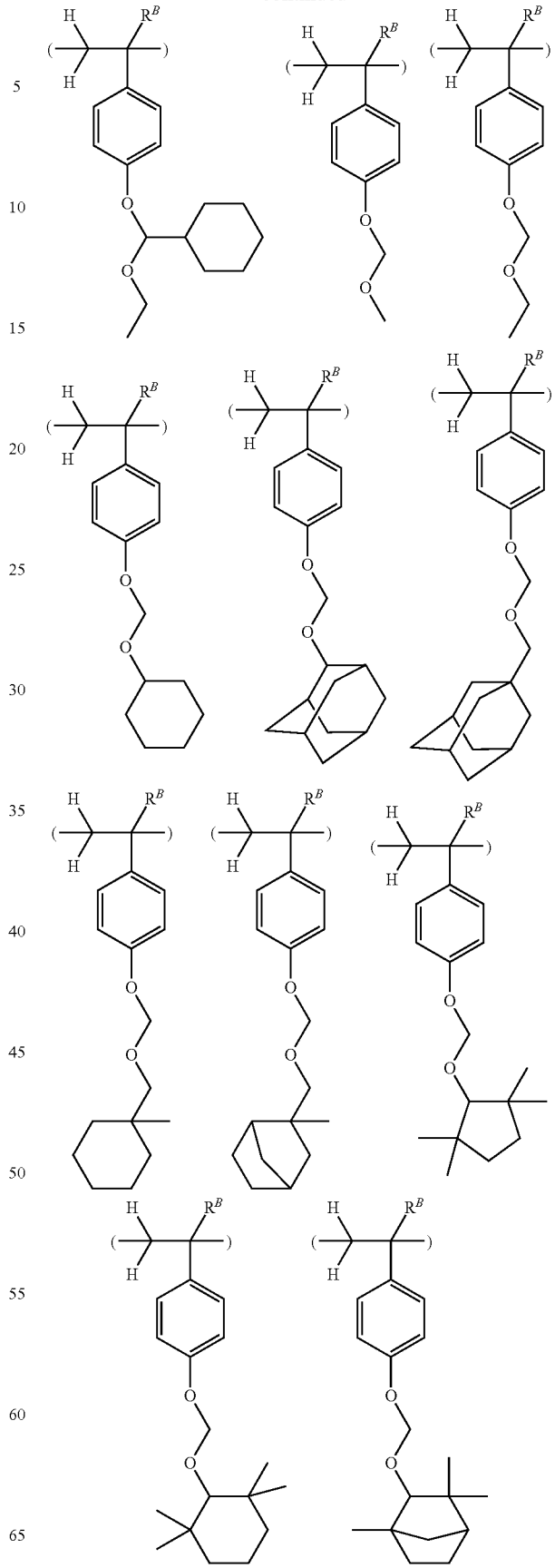

-continued

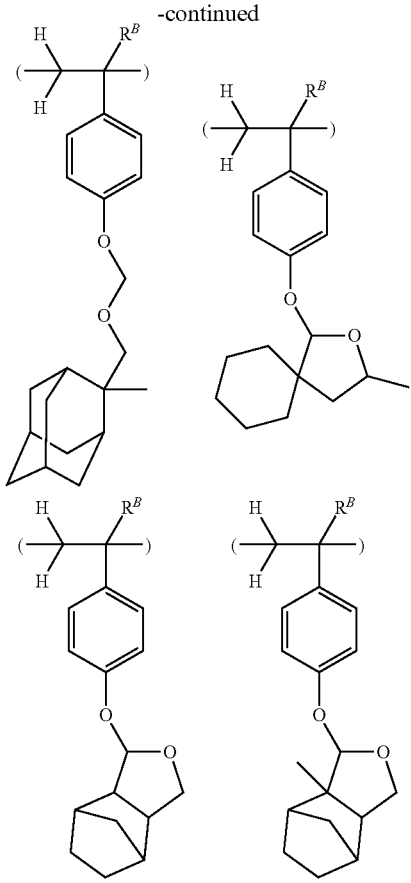
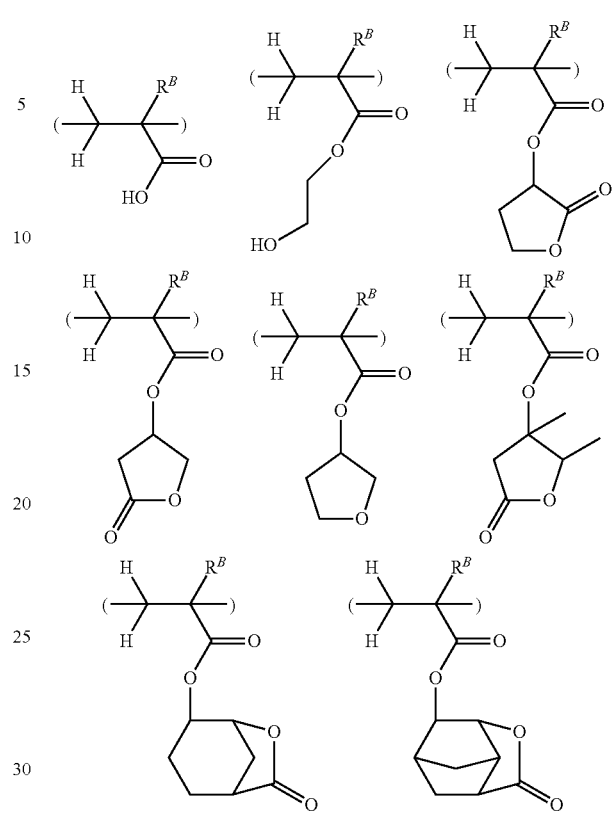

In addition, the polymer may further comprise recurring units having the formula (d) or (e).

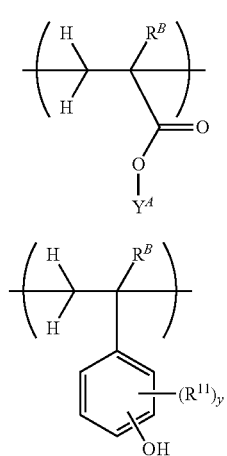
(d)

(e)

Herein $R^B$ and $R^{11}$ are as defined above. $Y^A$ is hydrogen or a polar group having at least one structure selected from hydroxy, cyano, carbonyl, carboxy, ether bond, ester bond, sulfonic acid ester bond, carbonate bond, lactone ring, sultone ring and carboxylic anhydride, and y is an integer of 0 to 4.

Examples of the recurring units of formula (d) are given below, but not limited thereto. Herein $R^B$ is as defined above

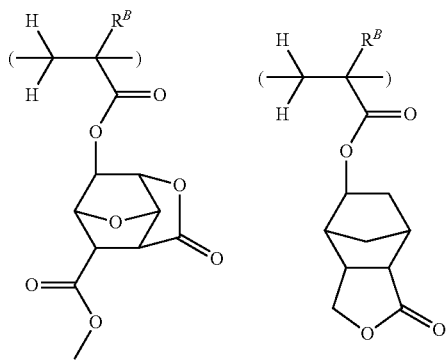
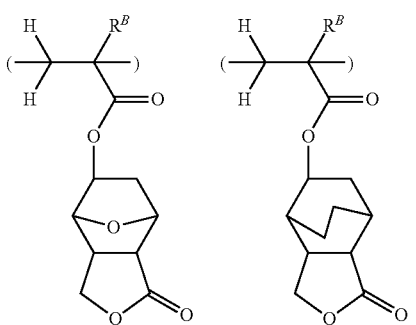

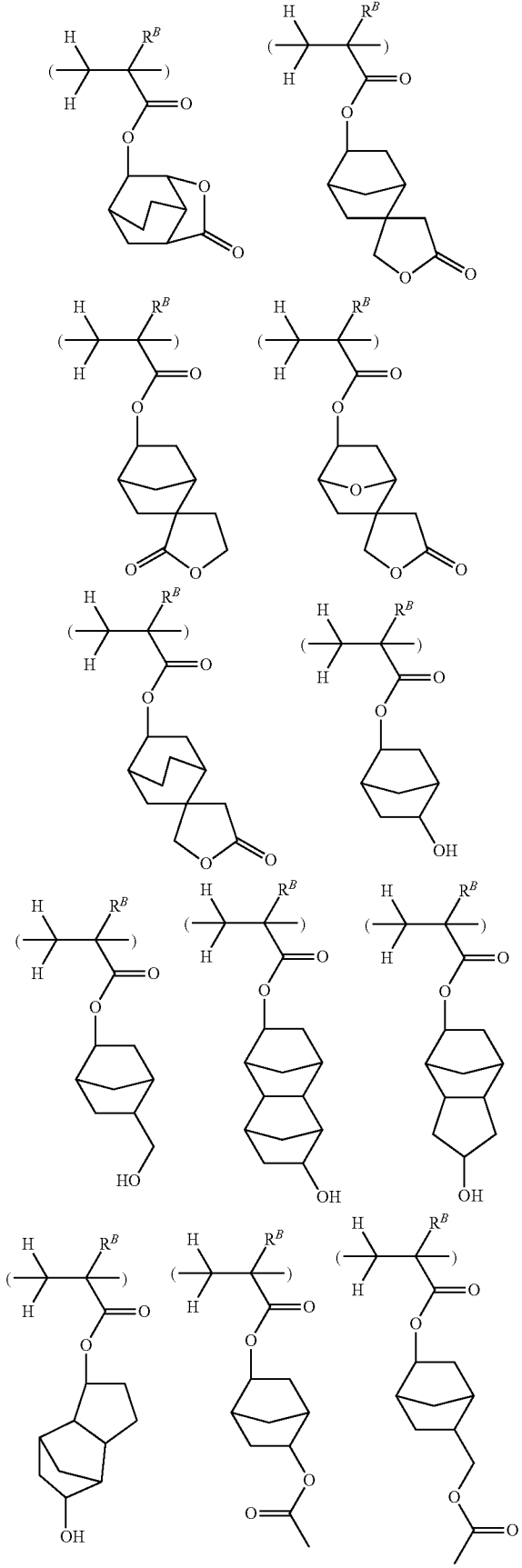
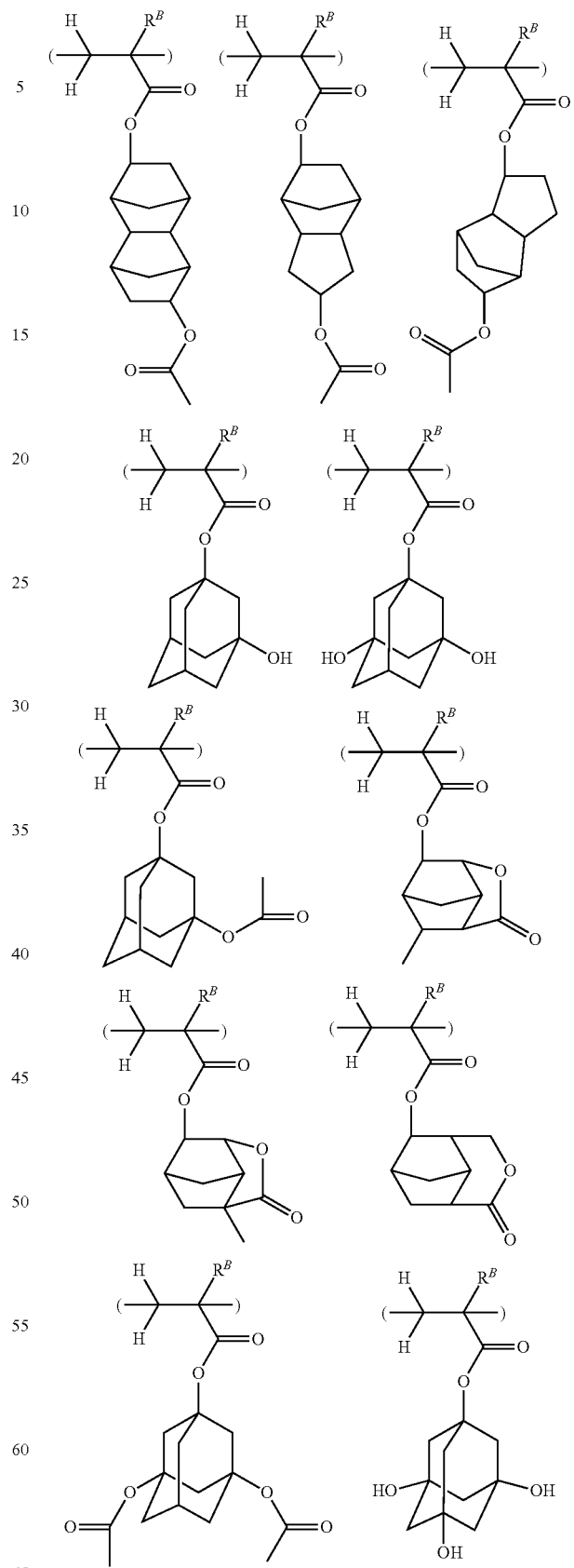

-continued
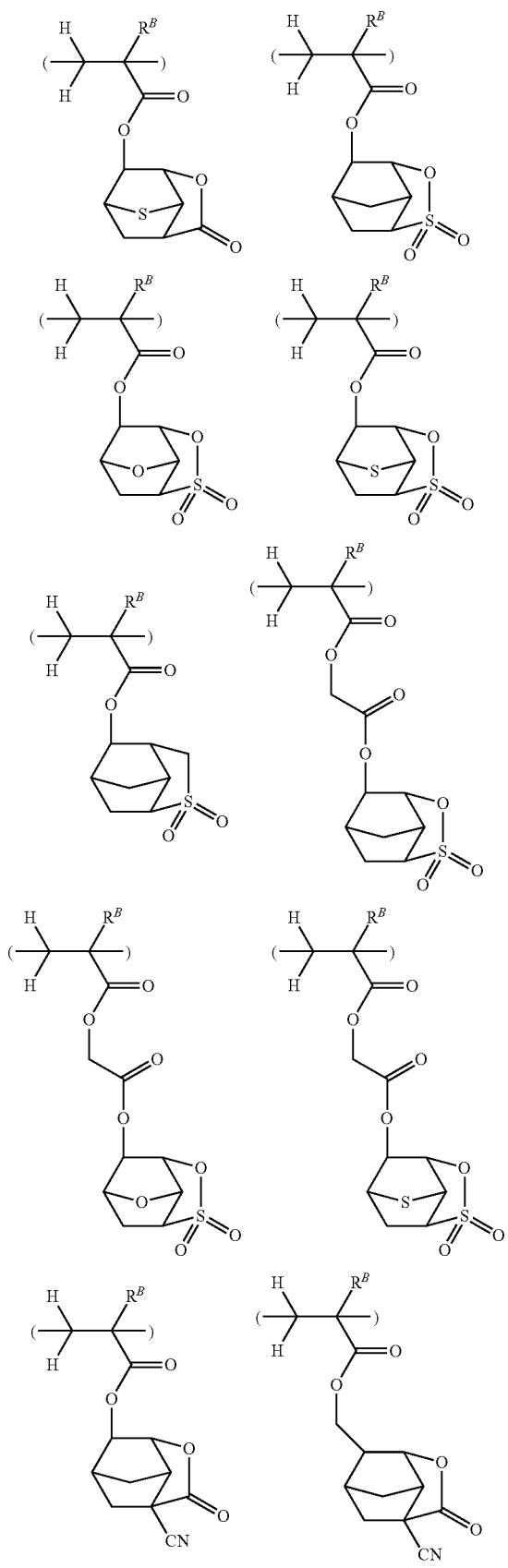
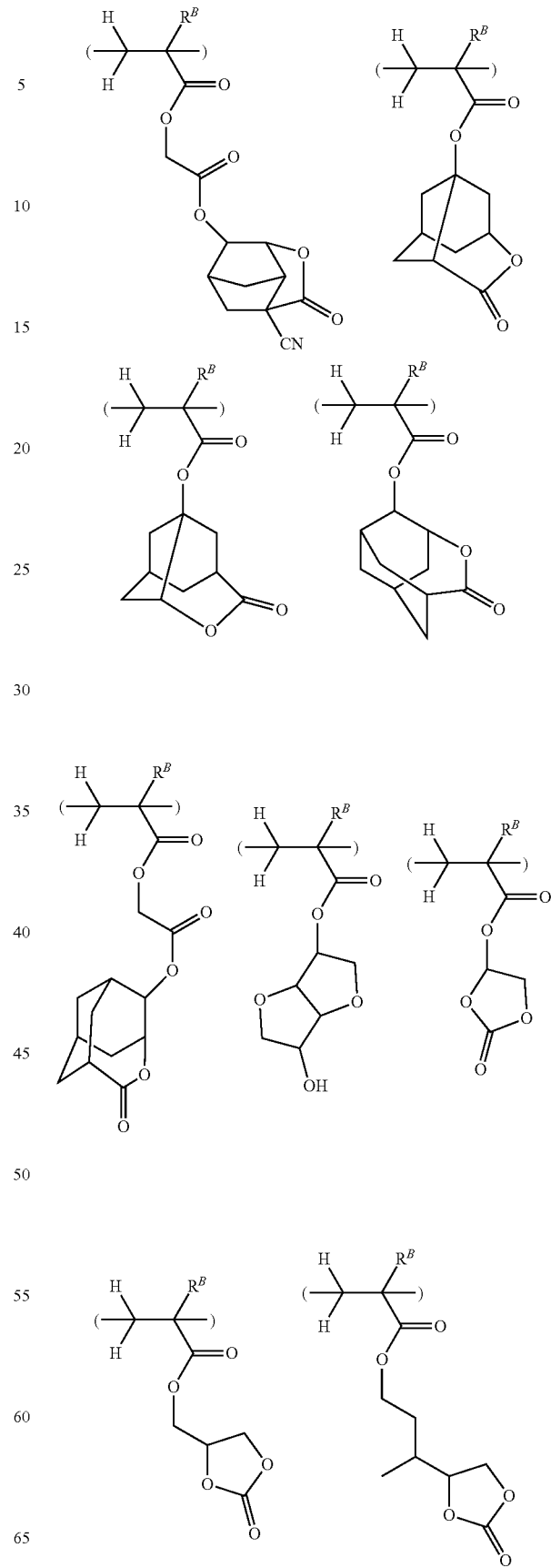

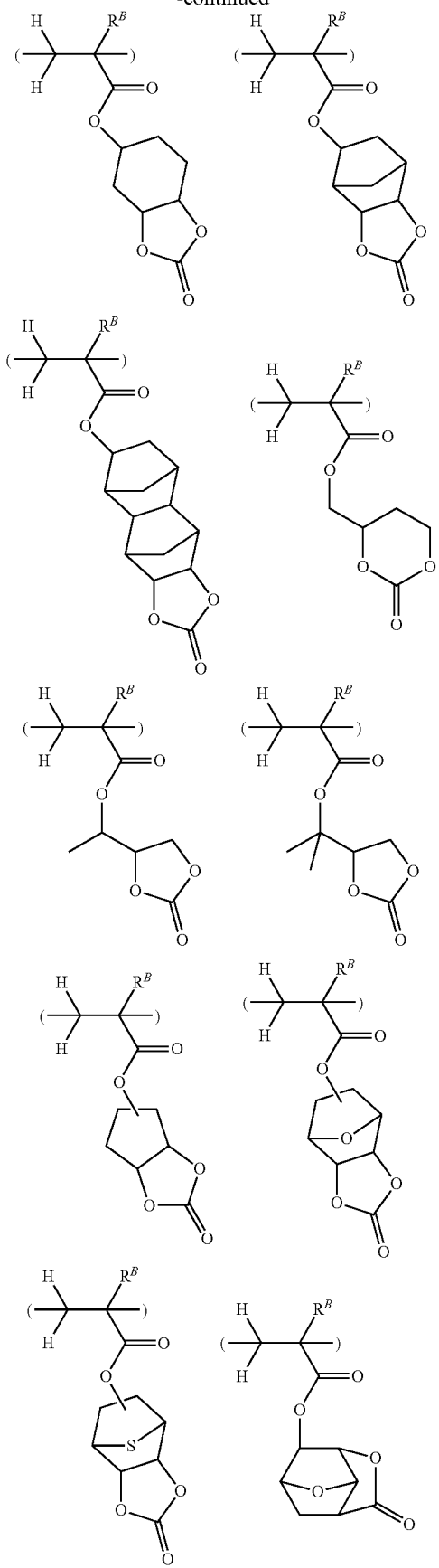
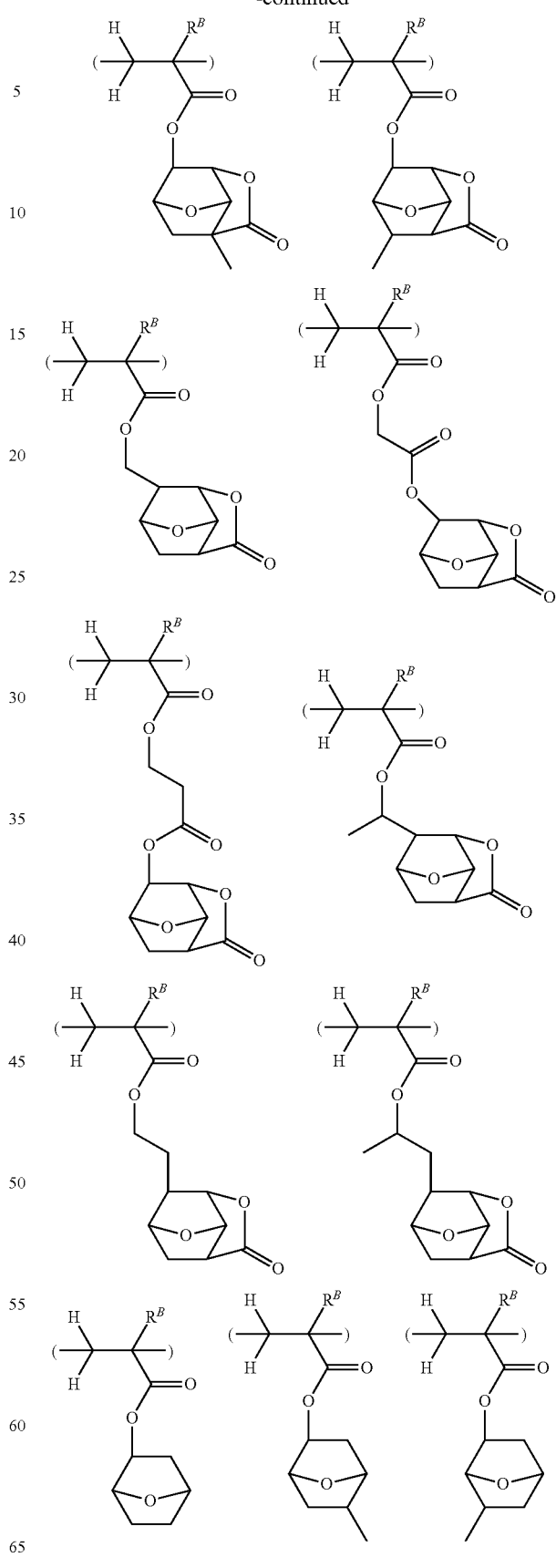

-continued
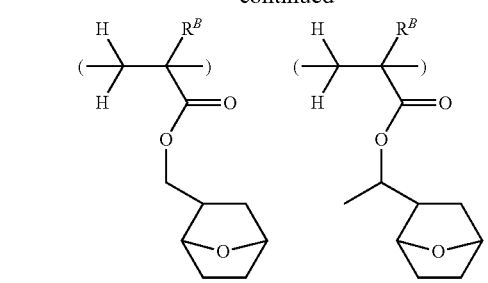
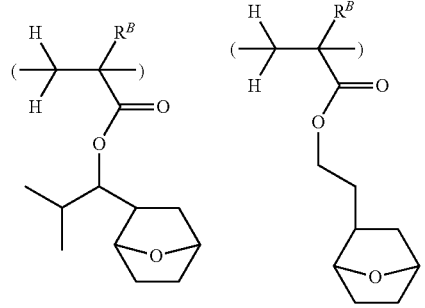
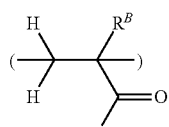
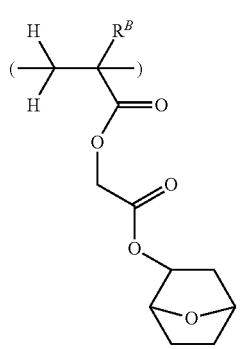
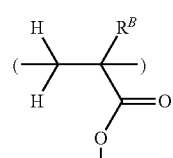
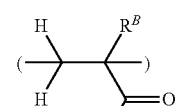
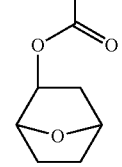
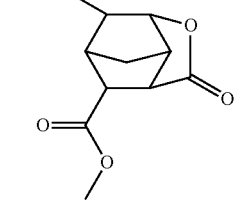
-continued
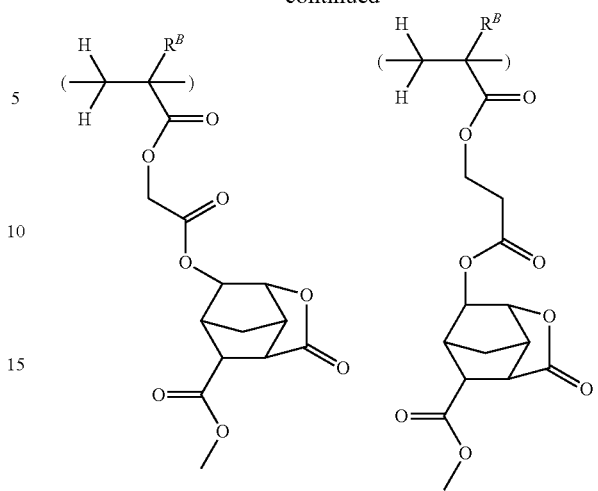
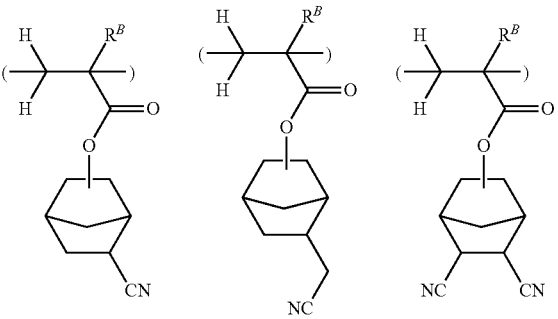
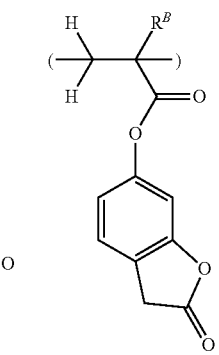
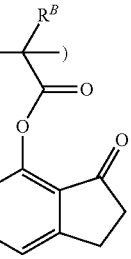
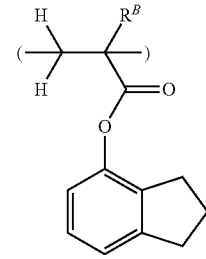

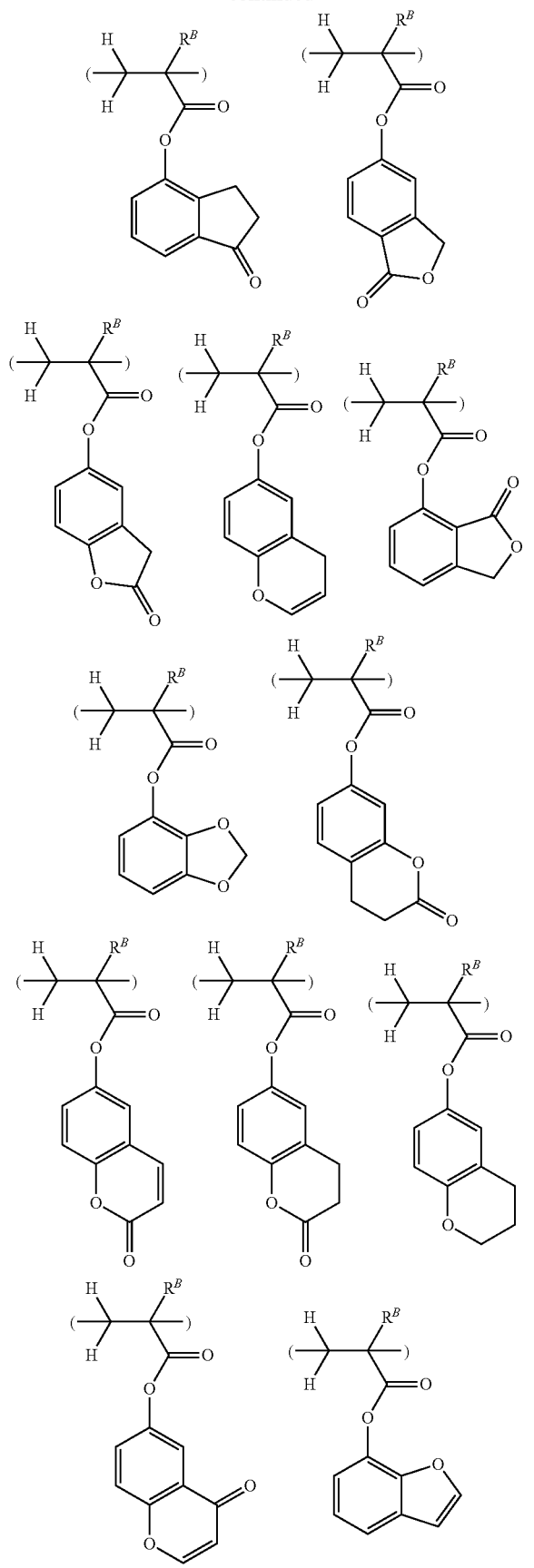
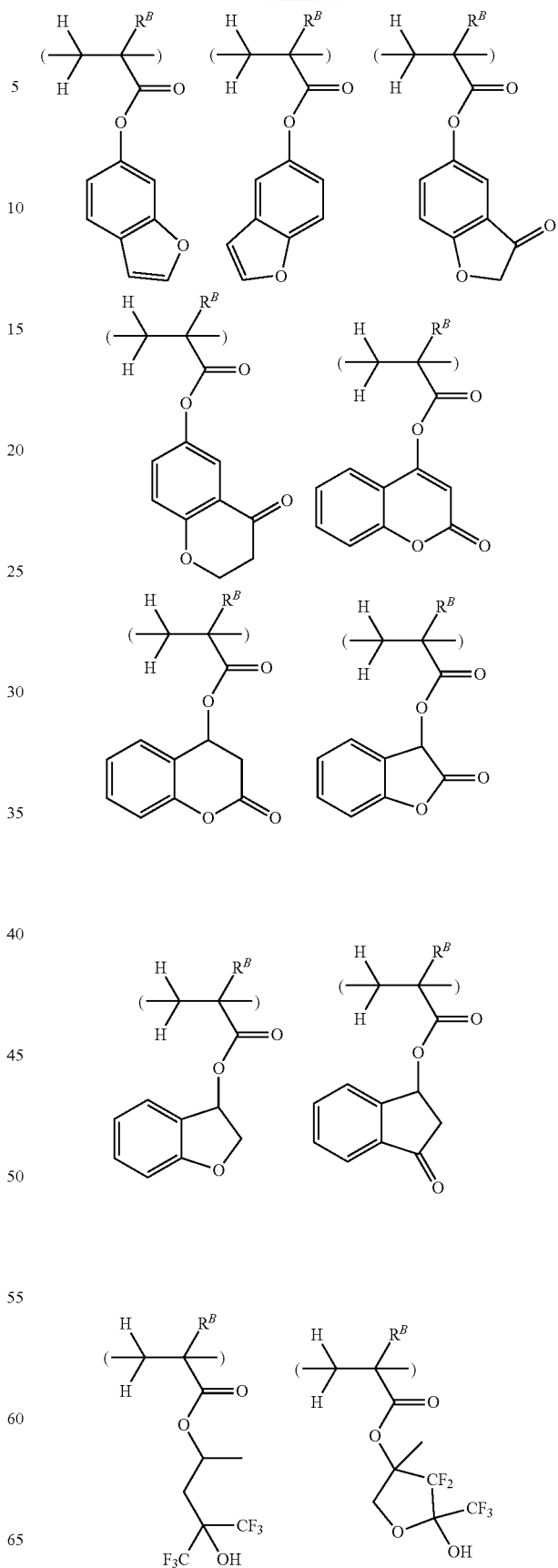

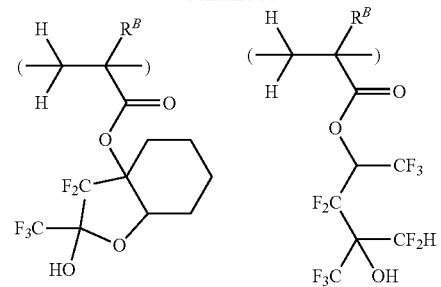
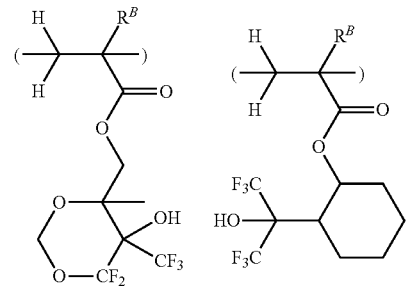
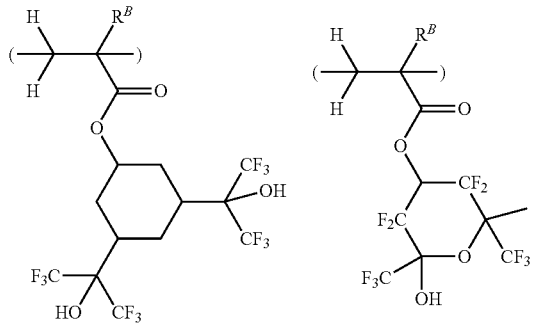
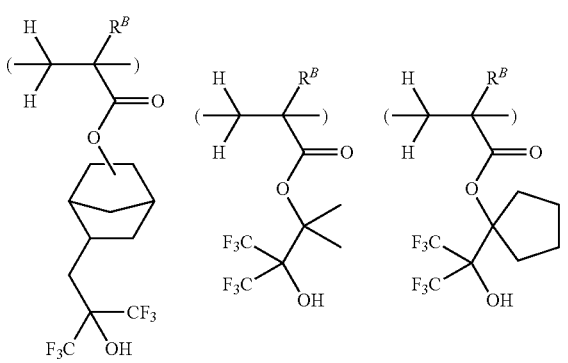
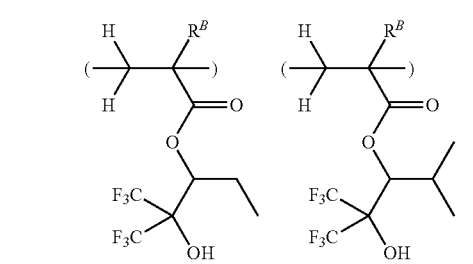
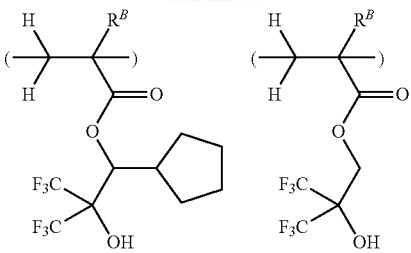
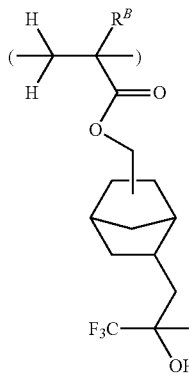
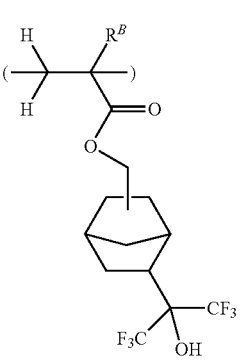
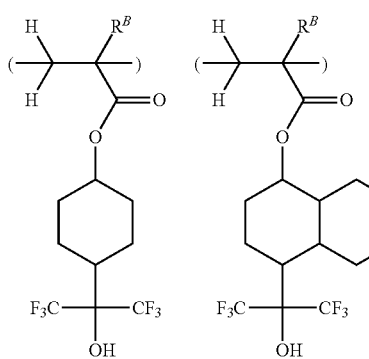
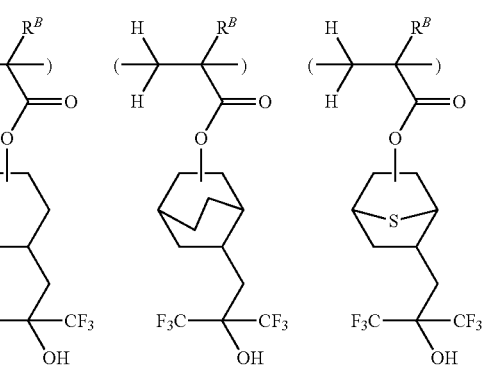

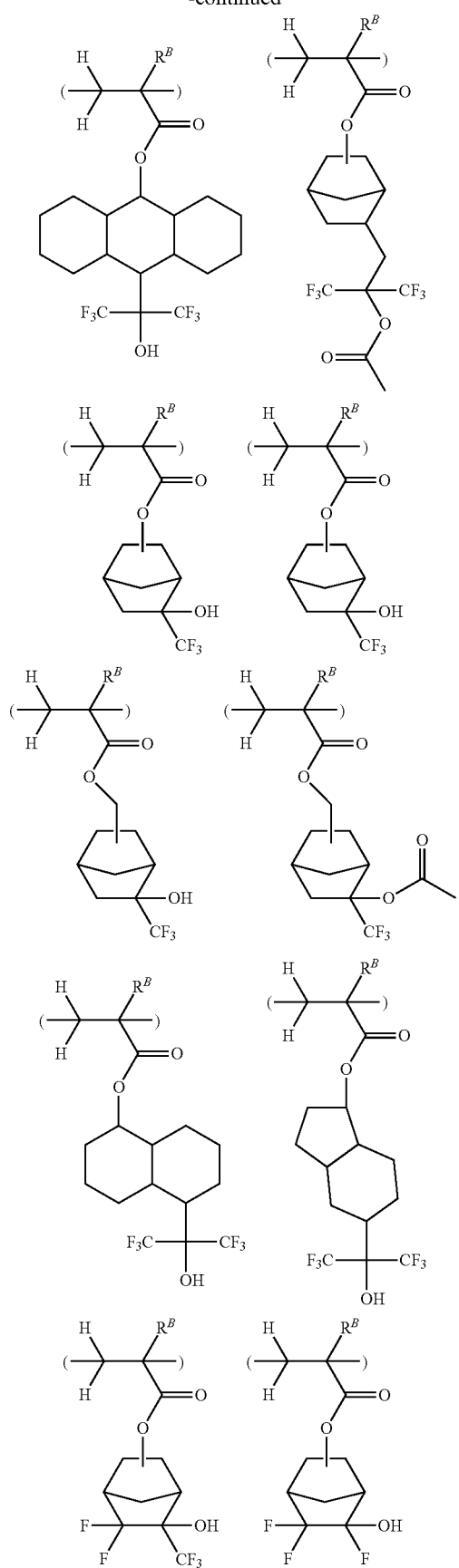
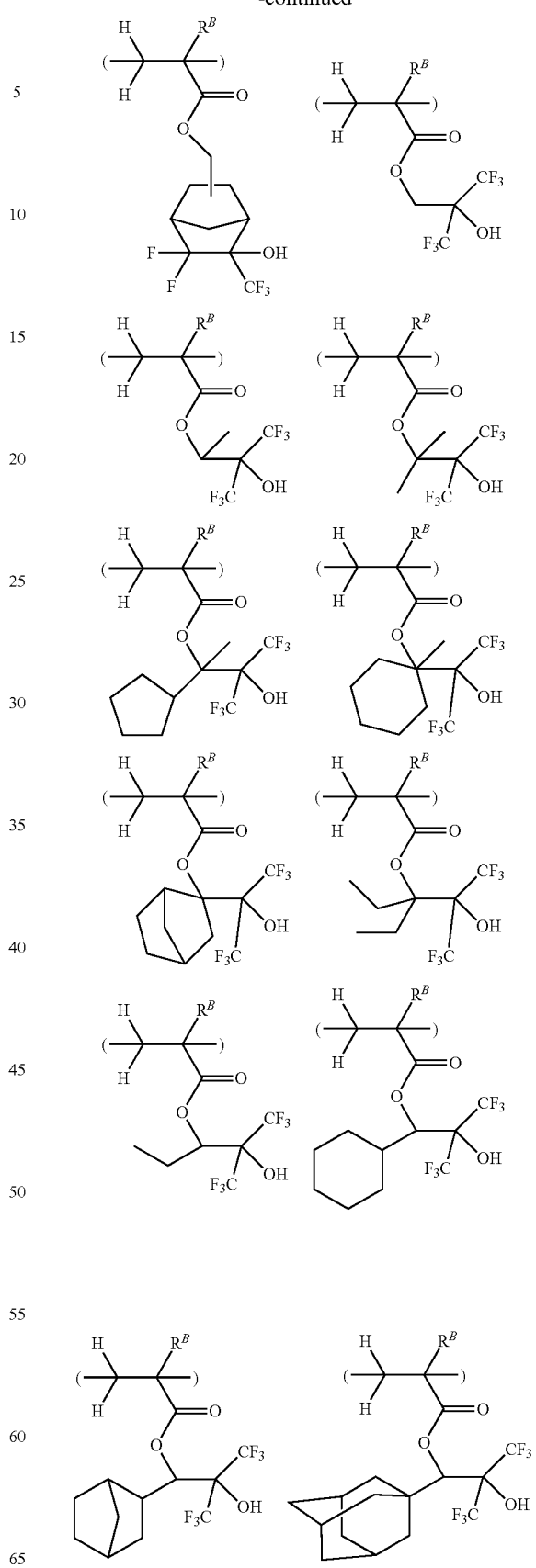

-continued
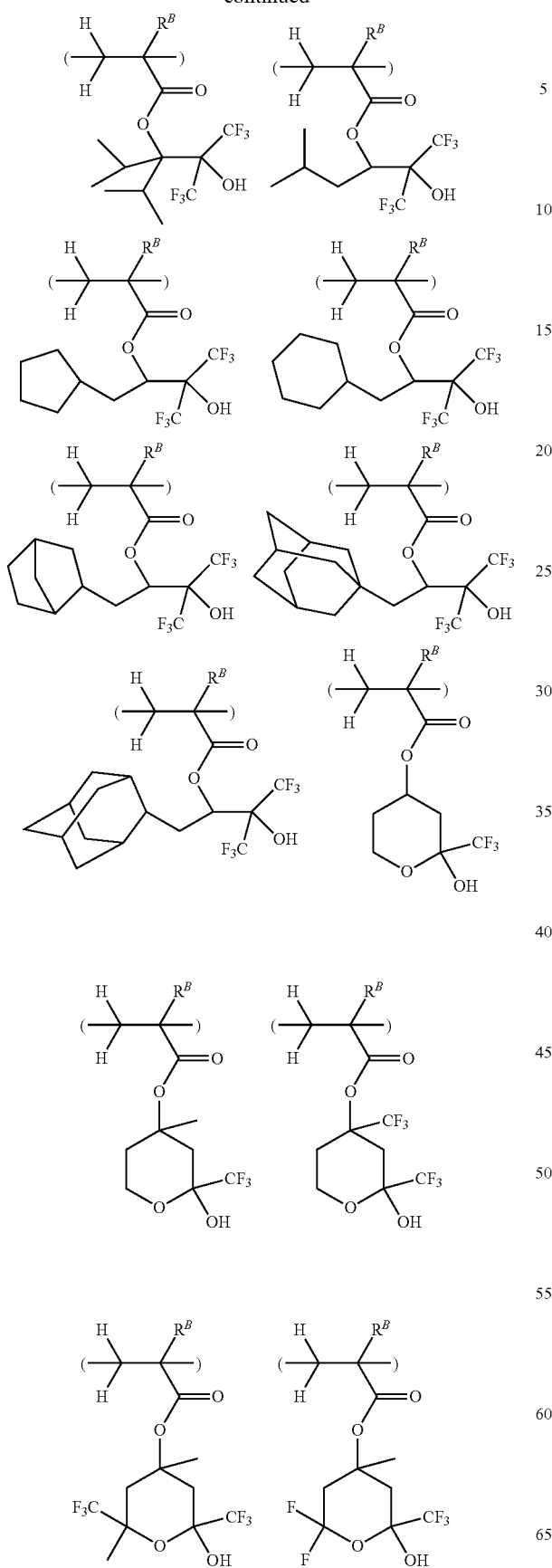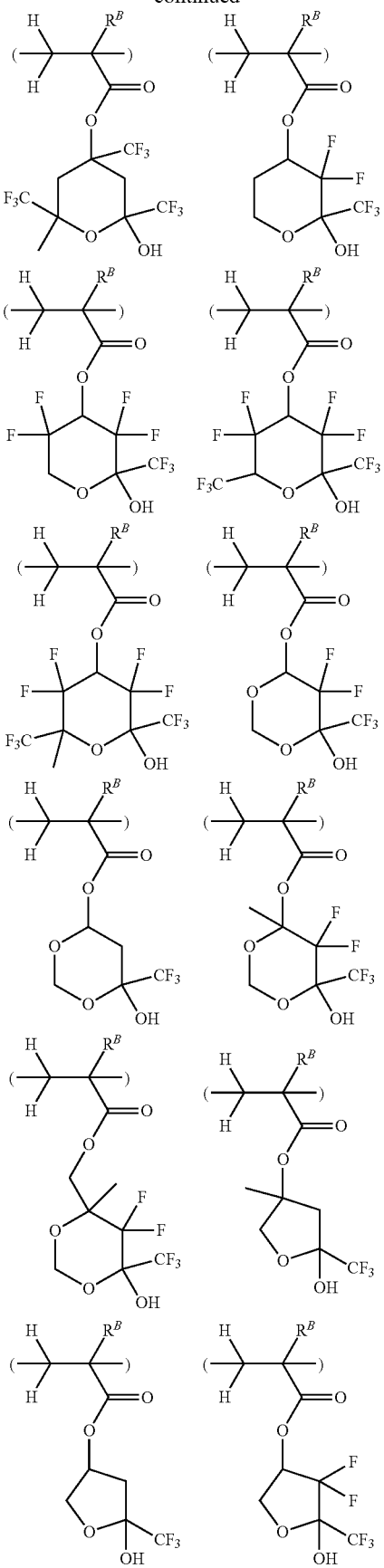

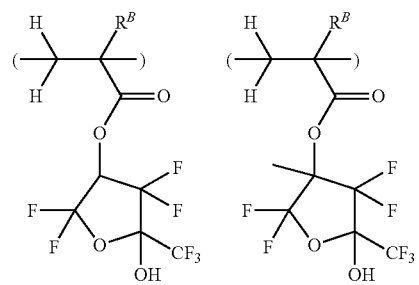
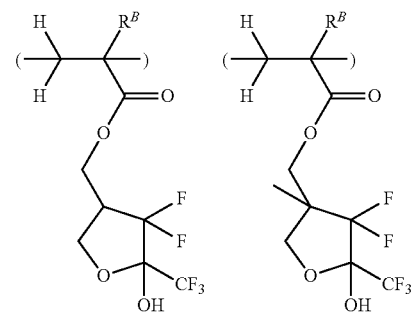
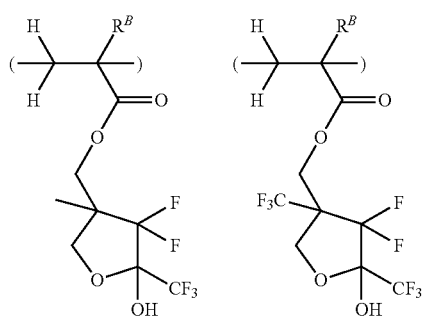
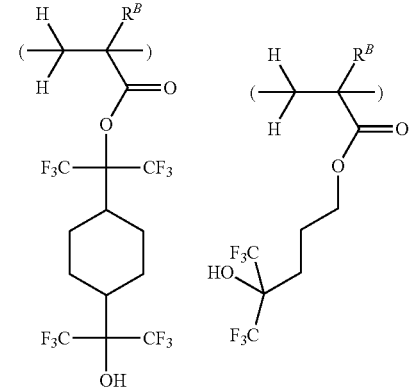
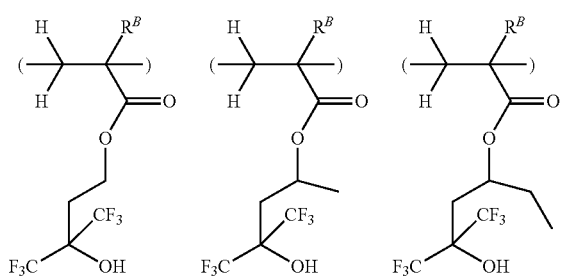
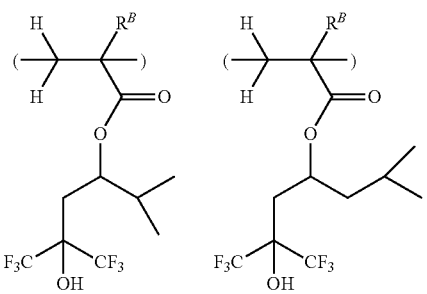
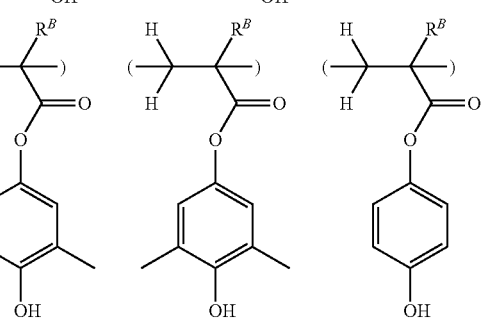
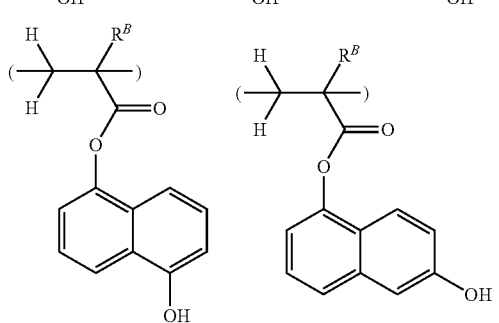
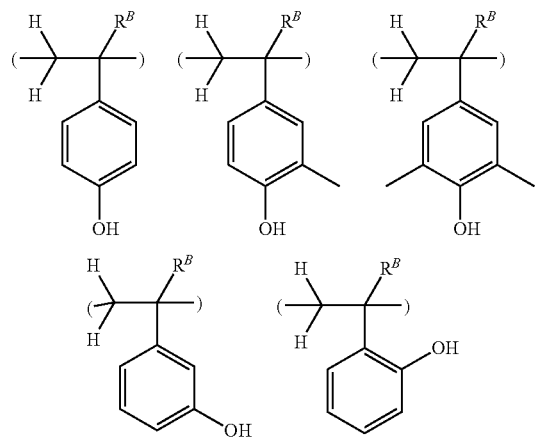
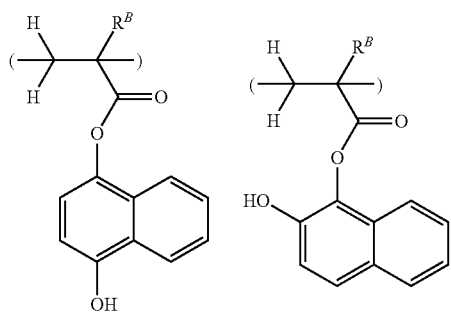

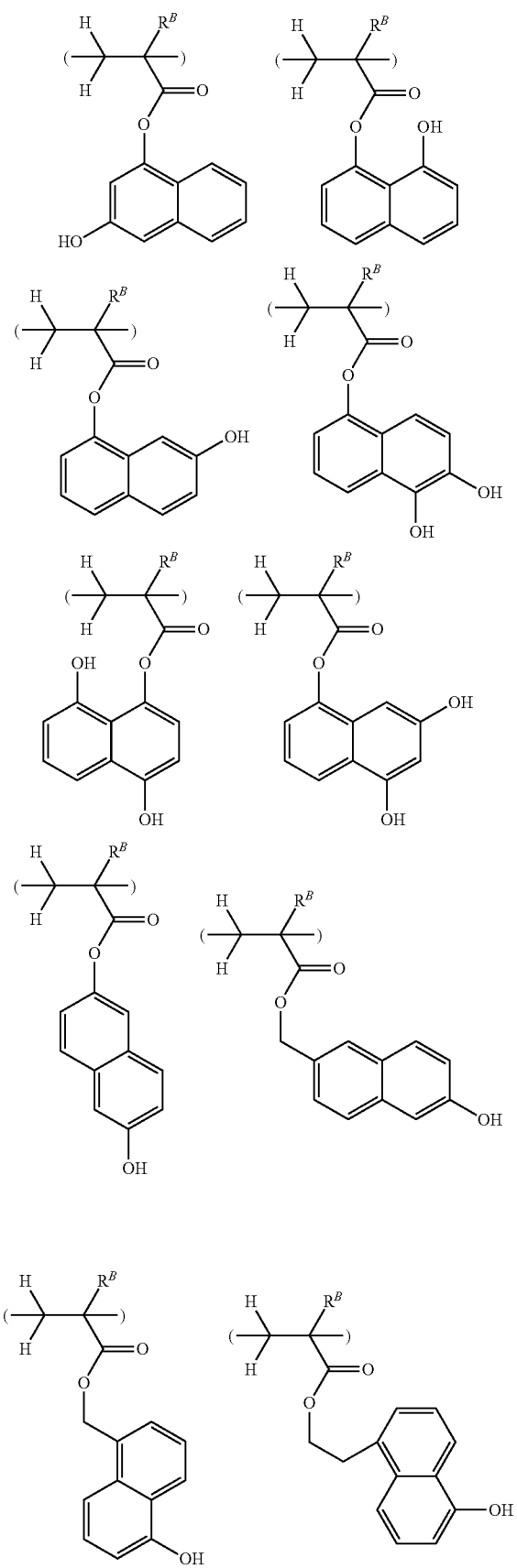
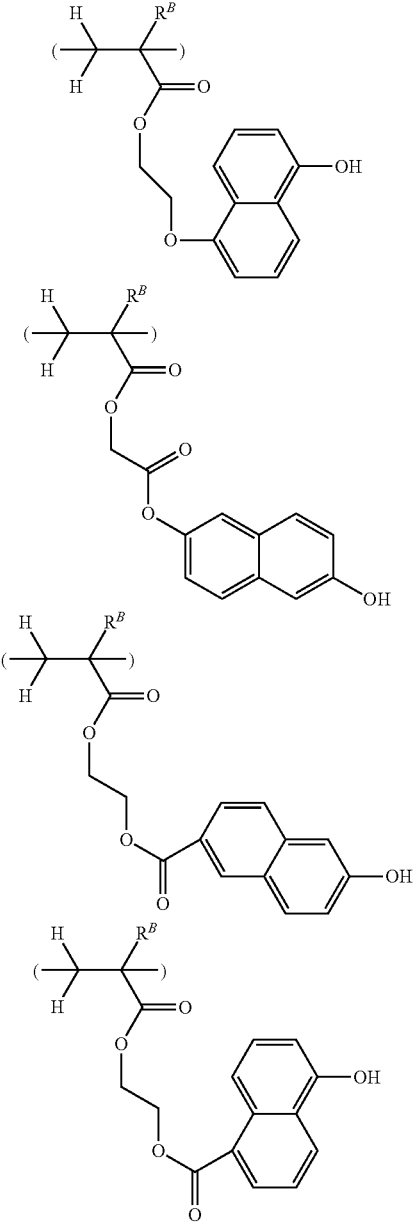

In addition to the foregoing units, the polymer may further comprise recurring units derived from other monomers, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo[6.2.1.1$^{3,6}$.0$^{2,7}$]dodecene derivatives, unsaturated acid anhydrides such as itaconic anhydride, and other monomers.

The polymer preferably has a weight average molecular weight (Mw) of 1,000 to 500,000, and more preferably 3,000 to 100,000, as measured versus polystyrene standards by GPC using tetrahydrofuran (THF) solvent. A Mw within the range eliminates the risk that resolution lowers due to difficulty to secure a dissolution rate difference before and after exposure.

If a polymer has a wide molecular weight distribution or dispersity (Mw/Mn) which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the polymer should preferably have a narrow dispersity (Mw/Mn) of 1.0 to 2.0 in order to provide a resist composition suitable for micropatterning to a small feature size.

The polymer may be synthesized by any desired methods, for example, by dissolving one or more monomers having an unsaturated bond in an organic solvent, adding a radical initiator thereto, and heating for polymerization. Examples of the organic solvent which can be used for polymerization include toluene, benzene, tetrahydrofuran (THF), diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. The reaction temperature is preferably 50 to 80° C., and the reaction time is preferably 2 to 100 hours, more preferably 5 to 20 hours. The acid labile group that has been incorporated in a monomer may be kept as such, or after polymerization, the product be protected or partially protected.

The polymer is preferably composed of recurring units in the following range, although the proportion is not limited thereto. The polymer preferably contains:

(I) 1 to 40 mol %, more preferably 1 to 35 mol %, even more preferably 1 to 30 mol % of recurring units derived from the inventive sulfonium salt;
(II) 1 to 50 mol %, more preferably 4 to 45 mol %, even more preferably 9 to 40 mol % of recurring units of at least one type having formula (a), (b) or (c);
(III) 10 to 98 mol %, more preferably 20 to 95 mol %, even more preferably 30 to 90 mol % of recurring units of at least one type having formula (d) or (e); and
(IV) 0 to 80 mol %, more preferably 0 to 70 mol %, even more preferably 0 to 50 mol % of recurring units of at least one type derived from another monomer(s).

Resist Composition

A further embodiment of the invention is a resist composition comprising
(A) a base polymer containing the polymer defined above as an essential component, and optionally,
(B) an organic solvent,
(C) a photoacid generator,
(D) an acid diffusion inhibitor, and
(E) a surfactant which is insoluble or substantially insoluble in water and soluble in alkaline developer, and/or a surfactant which is insoluble or substantially insoluble in water and alkaline developer (also referred to as hydrophobic resin).

In addition to the polymer defined above, the base polymer (A) may contain another polymer, such as a polymer not containing recurring units derived from the inventive sulfonium salt, or any well-known polymers used as the base polymer in resist compositions.

(B) Organic Solvent

The organic solvent used herein as component (B) is not particularly limited as long as the above components are soluble therein. Examples of the organic solvent are described in JP-A 2008-111103, paragraphs [0144] to [0145] (U.S. Pat. No. 7,537,880). Specifically, exemplary solvents include ketones such as cyclohexanone and methyl-2-n-pentyl ketone; alcohols such as 3-methoxybutanol, 3-methyl-3-methoxybutanol, 1-methoxy-2-propanol, 1-ethoxy-2-propanol, and diacetone alcohol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, and mixtures thereof. Where an acid labile group of acetal form is used, a high-boiling alcohol solvent such as diethylene glycol, propylene glycol, glycerol, 1,4-butanediol or 1,3-butanediol may be added for accelerating deprotection reaction of acetal. Of the above organic solvents, it is recommended to use 1-ethoxy-2-propanol, PGMEA, cyclohexanone, γ-butyrolactone, and mixtures thereof.

An appropriate amount of the organic solvent (B) used is 200 to 5,000 parts, more preferably 400 to 3,000 parts by weight per 100 parts by weight of the base polymer (A).

(C) PAG

While the photoacid generator (PAG) is incorporated in recurring units of the base polymer, the resist composition may separately contain (C) a photoacid generator, which is referred to as additive photoacid generator. The additive PAG is a compound free of a polymerizable group and used as an additive rather than recurring units in polymers. The additive PAG may be any compound capable of generating an acid upon exposure to high-energy radiation, preferably generating sulfonic acid, imide acid or methide acid. Suitable additive PAGs include sulfonium salts, iodonium salts, sulfonyldiazomethane, N-sulfonyloxyimide, and oxime-O-sulfonate compounds. Suitable PAGs are described, for example, in JP-A 2008-111103 paragraphs [0122]-[0139] and JP-A 2007-145797. An appropriate amount of the PAG (C) added is 0 to 200 parts, more preferably 0.1 to 100 parts by weight per 100 parts by weight of the base polymer (A).

(D) Acid Diffusion Inhibitor

The resist composition may contain an acid diffusion inhibitor. The term "acid diffusion inhibitor" refers to a compound capable of trapping the acid generated from the PAG to restrain excessive deprotection reaction. Nitrogen-containing compounds are typical. Suitable nitrogen-containing compounds include primary, secondary and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amide derivatives, imide derivatives, and carbamate derivatives. Exemplary acid diffusion inhibitors include primary, secondary and tertiary amine compounds, specifically amine compounds having a hydroxyl, ether, ester, lactone, cyano or sulfonate group, as described in JP-A 2008-111103, paragraphs [0146] to [0164], and compounds having a carbamate group, as described in JP 3790649. The addition of an acid diffusion inhibitor makes it possible to further restrain the diffusion rate of the generated acid within a resist film and to correct the profile of a pattern.

Examples of the acid diffusion inhibitor other than the nitrogen-containing compounds include onium salts such as sulfonium, iodonium and ammonium salts of sulfonic acids which are not fluorinated at α-position or carboxylic acids. While an α-fluorinated sulfonic acid, imide acid or methide acid is necessary to deprotect an acid labile group of carboxylate, it undergoes salt exchange with an onium salt of α-non-fluorinated sulfonic acid, releasing α-non-fluorinated sulfonic acid or carboxylic acid. Since the α-non-fluorinated sulfonic acid or carboxylic acid does not incur deprotection reaction, it functions as an acid diffusion inhibitor.

An appropriate amount of the acid diffusion inhibitor (D) added is 0.001 to 20 parts, more preferably 0.01 to 10 parts by weight per 100 parts by weight of the base polymer (A). The acid diffusion inhibitor may be used alone or in admixture.

(E) Surfactant

The resist composition may further comprise (E) a surfactant which is insoluble or substantially insoluble in water and soluble in alkaline developer, and/or a surfactant which is insoluble or substantially insoluble in water and alkaline developer (hydrophobic resin). For the surfactant, reference should be made to those compounds described in JP-A 2010-215608 and JP-A 2011-016746.

While many examples of the surfactant which is insoluble or substantially insoluble in water and alkaline developer are described in the patent documents cited herein, preferred examples are FC-4430, Surflon® S-381, Surfynol® E1004, KH-20 and KH-30, which may be used alone or in admixture. Partially fluorinated oxetane ring-opened polymers having the formula (surf-1) are also useful.

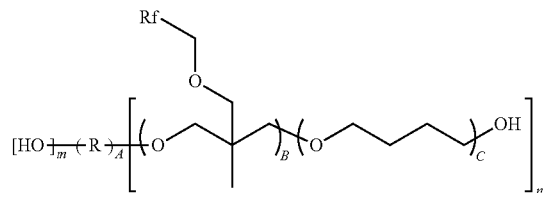

(surf-1)

It is provided herein that R, Rf, A, B, C, m, and n are applied to only formula (surf-1), independent of their descriptions other than for the surfactant. R is a di- to tetra-valent $C_7$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

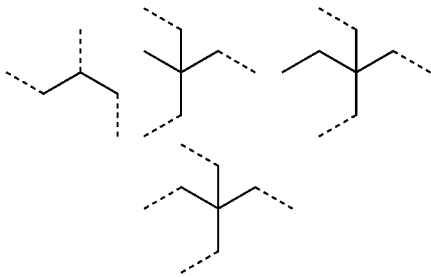

Herein the broken line denotes a valence bond. These formulae are partial structures derived from glycerol, trimethylol ethane, trimethylol propane, and pentaerythritol, respectively, of these, 1,4-butylene and 2,2-dimethyl-1,3-propylene are preferably used.

Rf is trifluoromethyl or pentafluoroethyl, and preferably trifluoromethyl. The letter m is an integer of 0 to 3, it is an integer of 1 to 4, and the sum of m and n, which represents the valence of R, is an integer of 2 to 4. A is equal to 1, B is an integer of 2 to 25, and C is an integer of 0 to 10. Preferably, B is an integer of 4 to 20, and C is 0 or 1. Note that the formula (surf-1) does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful. When ArF immersion lithography is applied to the resist composition in the absence of a resist protective film. In this embodiment, the surfactant has a propensity to segregate on the resist surface after spin coating for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water slippage.

Suitable polymeric surfactants are shown below.

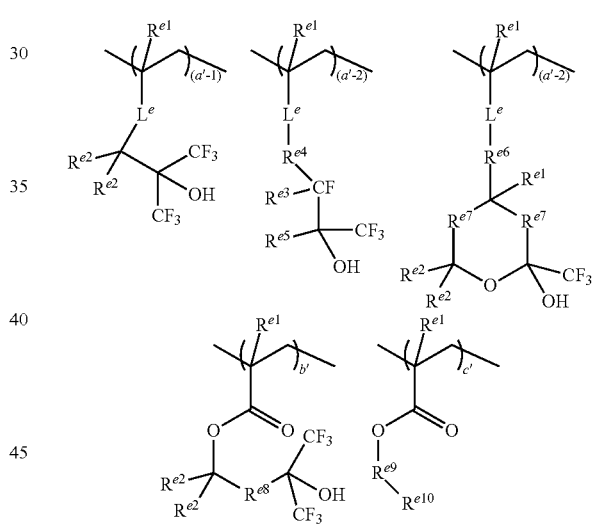

Herein $R^{e1}$ is each independently hydrogen, fluorine, methyl or trifluoromethyl, $R^{e2}$ is each independently hydrogen or a straight, branched or cyclic $C_1$-$C_{20}$ alkyl or fluoroalkyl group, or two $R^{e2}$ in a common unit may bond together to form a ring with the carbon atom to which they are attached, and in this event, they together represent a straight, branched or cyclic $C_2$-$C_{20}$ alkylene or fluoroalkylene group.

$R^{e3}$ fluorine or hydrogen, or $R^{e3}$ may bond with $R^{e4}$ to form a non-aromatic ring of 3 to 10 carbon atoms in total with the carbon atom to which they are attached. $R^{e4}$ is a straight, branched or cyclic $C_1$-$C_6$ alkylene group in which at least one hydrogen atom may be substituted by a fluorine atom. $R^{e5}$ is a straight or branched $C_1$-$C_{10}$ alkyl group in which at least one hydrogen atom is substituted by a fluorine atom. Alternatively, $R^{e4}$ and $R^{e5}$ may bond together to form a non-aromatic ring with the carbon atoms to which they are attached. In this event, $R^{e4}$, $R^{e5}$ and the carbon atoms to which they are attached together represent a trivalent organic group of 3 to 12 carbon atoms in total. $R^{e6}$ is a single bond or a $C_1$-$C_4$ alkylene.

$R^{e7}$ is each independently a single bond, —O—, or —$CR^{e1}R^{e1}$—, $R^{e8}$ is a $C_1$-$C_4$ straight or branched alkylene group, or may bond with $R^{e2}$ within a common unit to form a $C_3$-$C_6$ non-aromatic ring with the carbon atom to which they are attached. $R^{e9}$ is methylene, 1,2-ethylene, 1,3-propylene or 1,4-butylene.

$R^{e10}$ is a $C_3$-$C_6$ linear perfluoroalkyl group, typically 3H-perfluoropropyl, 4H-perfluorobutyl, 5H-perfluoropentyl or 6H-perfluorohexyl. $L^e$ is each independently —C(=O)—O—, —O—, or —C(=O)—$R^{e11}$—C(=O)—O—. $R^{e11}$ is a straight, branched or cyclic $C_1$-$C_{10}$ alkylene group. The subscripts are in the range: $0 \le (a'-1) \le 1$, $0 \le (a'-2) \le 1$, $0 \le (a'-3) \le 1$, $0 < (a'-1)+(a'-2)+(a'-3) \le 1$, $0 \le b' \le 1$, $0 \le c' \le 1$, and $0 < (a'-1)+(a'-2)+(a'-3)+b'+c' \le 1$.

Examples of these recurring units are shown below, but not limited thereto. Herein $R^{e1}$ is as defined above.

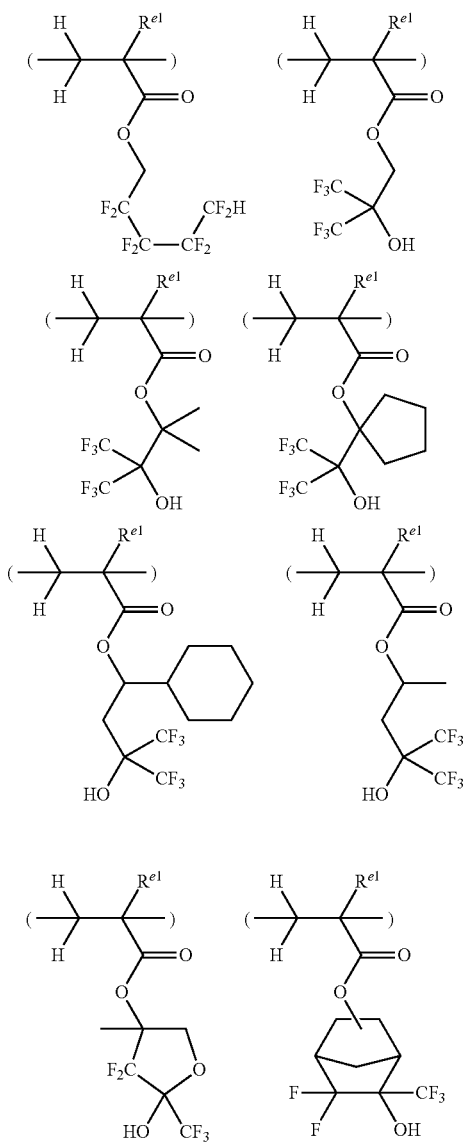

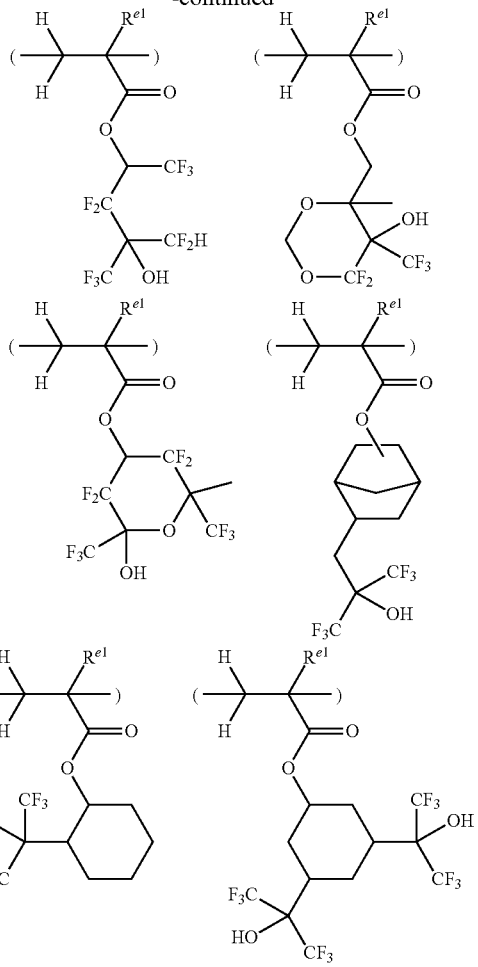

-continued

The polymeric surfactant has a Mw of preferably 1,000 to 50,000, more preferably 2,000 to 20,000 as measured by GPC versus polystyrene standards. A surfactant with a Mw within the range may be effective for surface modification and cause few or no development defects.

For the surfactant which is insohible or substantially insoluble in water and soluble in alkaline developer, reference may be made to JP-A 2008-122932, 2009-098638, 2009-191151, 2009-192784, 2009-276363, 2010-107695, 2010-134012, 2010-250105, and 2011-042789.

An appropriate amount of surfactant (E) is 0 to 20 parts by weight per 100 parts by weight of the base polymer (A). The lower limit is preferably 0.001 part, and more preferably 0.01 part by weight, whereas the upper limit is preferably 15 parts, and more preferably 10 parts by weight. The surfactant may be used alone or in admixture of two or more.

Process

A further embodiment of the invention is a pattern forming process using the resist composition defined above. A pattern may be formed from the resist composition using any well-town lithography process.

Specifically, the resist composition is applied onto a substrate for integrated circuitry fabrication (e.g., Si, $SiO_2$, SiN, SiON, TiN WSi BPSG SOG, organic antireflective film, etc.) or a substrate for mask circuitry fabrication (e.g., Cr, CrO, CrON, $MoSi_2$, $SiO_2$, etc.) by a suitable coating technique such as spin coating. The coating is prebaked on a hotplate at a temperature of 60 to 150° C. for 1 to 10 minutes, preferably 80 to 140° C. for 1 to 5 minutes. The resulting resist film is generally 0.05 to 2 μm thick.

Through a mask having a desired pattern disposed over the substrate, the resist film is then exposed to high-energy radiation such as KrF excimer laser, ArF excimer laser or EUV in an exposure dose preferably in the range of 1 to 200 mJ/cm$^2$, more preferably 10 to 100 mJ/cm$^2$. Alternatively, pattern formation may be performed by writing with EB directly in a dose of preferably 0.1 to 100 μC/cm$^2$, more preferably 0.5 to 50 μC/cm$^2$. Light exposure may be done by a conventional lithography process or in some cases, by an immersion lithography process of providing a liquid having a refractive index of at least 1.0 between the projection lens and the resist film. The preferred liquid is water. In the case of immersion lithography, a protective film which is insoluble in water may be formed on the resist film.

The resist film is then baked (PEB) on a hotplate at 60 to 150° C. for 1 to 5 minutes, and preferably at 80 to 140° C. for 1 to 3 minutes. Finally, development is carried out using as the developer an aqueous alkaline solution, such as a 0.1 to 5 wt %, preferably 2 to 3 wt %, aqueous solution of tetramethylammonium hydroxide (TMAH), this being done by a conventional method such as dip, puddle, or spray development for a period of 0.1 to 3 minutes, and preferably 0.5 to 2 minutes. In this way the desired pattern is formed on the substrate.

While the water-insoluble protective film which is used in the immersion lithography serves to prevent any components from being leached out of the resist film and to improve water slippage at the film surface, it is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

Any desired step may be added to the pattern forming process. For example, after a resist film is formed, a step of rinsing with pure water (post-soaking) may be introduced to extract the acid generator or the like from the film surface or wash away panicles. After exposure, a step of rinsing (post-soaking) may be introduced to remove any water remaining on the film after exposure.

A pattern may also be formed by a double patterning process. The double patterning process includes a trench process of processing an underlay to a 1:3 trench pattern by a first step of exposure and etching, shifting the position, and forming a 1:3 trench pattern by a second step of exposure for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

In the pattern forming process, an alkaline aqueous solution is often used as the developer. The negative tone development technique using an organic solvent instead is also applicable wherein the unexposed region is developed and dissolved in the organic solvent.

In the organic solvent development, the organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, phenyl acetate, propyl formate, butyl formate, isobutyl formate, pentyl formate, isopentyl formate, methyl valerate, methyl pentenoate, methyl crotonate, ethyl crotonate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

EXAMPLE

Synthesis Examples, Examples and Comparative Examples are given below by way of illustration and not by way of limitation. The abbreviation "pbw" is parts by weight. For all polymers, Mw and Mn are determined by GPC versus polystyrene standards using THF solvent. THE stands for tetrahydrofuran, MEK for methyl ethyl ketone, and MIBK for methyl isobutyl ketone. Analytic instruments are as shown below.

IR: NICOLET 6700 by Thermo Fisher Scientific Inc.
$^1$H-NMR: ECA-500 by JEOL Ltd.
$^{19}$F-NMR: ECA-500 by JEOL Ltd.
MALDI-TOF-MS: S3000 by JEOL Ltd.

1) Synthesis of Sulfonium Salt PAG-A

Example 1-1

Synthesis of PAG Intermediate 1

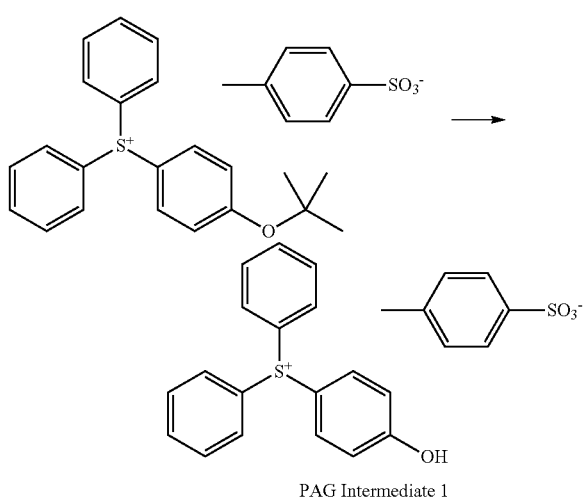

PAG Intermediate 1

A mixture of 250 g of (4-tert-butyloxyphenyl)diphenylsulfonium p-toluenesulfonate, 5 g of p-toluenesulfonic acid monohydrate, and 750 g of methanol was stirred at 80° C. for 5 hours. The reaction solution was cooled down to room temperature and concentrated under reduced pressure. To the concentrate were added 1,000 g of methylene chloride and 500 g of deionized water. An organic layer was taken out, washed with water, and concentrated under reduced pressure. MIBK 1,000 g, was added to the residue, which was concentrated under reduced pressure again. There was obtained 240 g of the end compound, PAG Intermediate 1 as oily matter (yield 96%).

Example 1-2

Synthesis of PAG Intermediate 2

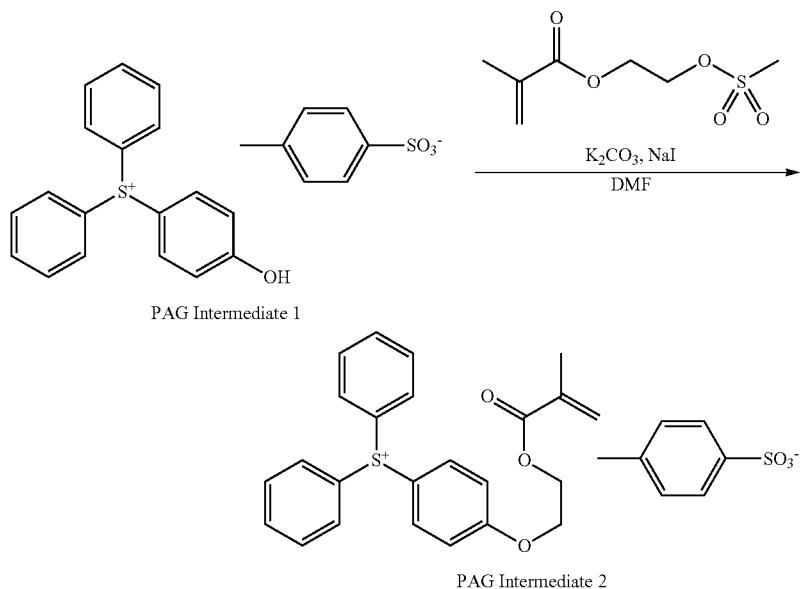

PAG Intermediate 1

PAG Intermediate 2

A mixture of 140 g of PAG Intermediate 1, 97 g of 2-methanesulfonyloxyethyl methacrylate, 42 g of potassium carbonate, 2 g of sodium iodide, 60 g of methylene chloride, and 700 g, of dimethylformanaide was stirred at 80° C. for 3 hours. The reaction solution was combined with 10 wt % sodium chloride aqueous solution and washed with 600 g of n-hexane. After washing, 300 g of methylene chloride was added to the water layer, from which an organic layer was extracted. The organic layer was washed with water and concentrated under reduced pressure. The residue was washed with diisopropyl ether, combined with 1,000 g of MIBK, and concentrated under reduced pressure again. There was obtained 240 g of the end compound, PAG Intermediate 2 as oily matter (yield 68%).

Example 1-3

Synthesis of PAG Intermediate 3

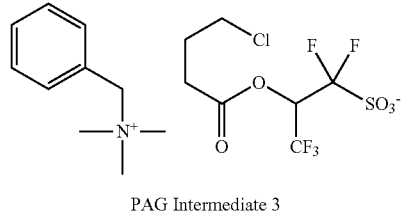

PAG Intermediate 3

Under ice cooling, 19 g of pyridine was added to a mixture of 75 g of benzyltrimethylammonium 2-hydroxy-1,1,3,3,3-pentafluoropropane-1-sulfonate (as synthesized according to the method described in JP-A 2016-218089 or US 20160334706), 31 g of 4-chlorobutyric acid chloride, 380 g of methylene chloride. The solution was heated at room temperature and stirred for 20 hours. Dilute hydrochloric acid was added to the reaction solution to quench the reaction. An organic layer was taken out and washed with water, combined with 200 g of MIBK, and concentrated under reduced pressure. To the residue was added 300 g of diisopropyl ether. The thus precipitated crystal was recovered and dried in vacuum by heating. There was obtained 87 g of the end compound, PAG Intermediate 3 as white solid (yield 90%).

Example 1-4

Synthesis of PAG Intermediate 4

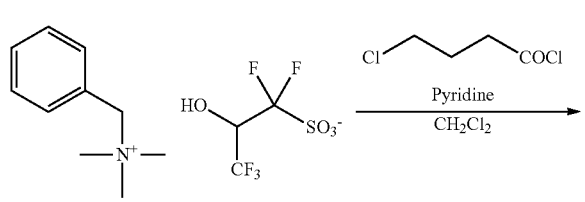 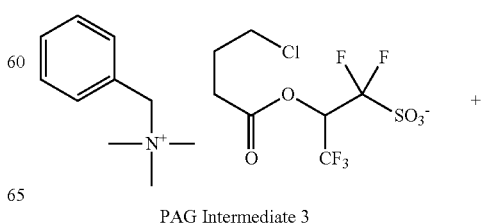

PAG Intermediate 3

-continued

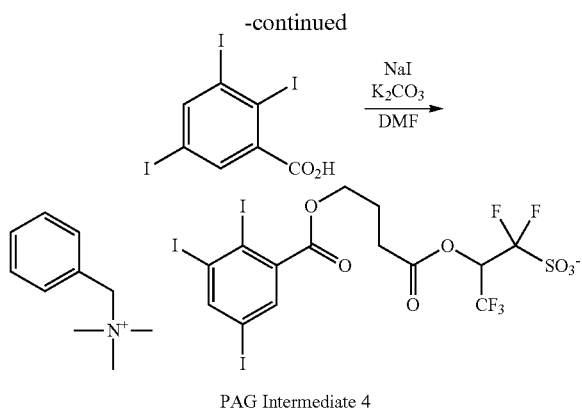

PAG Intermediate 4

A mixture of 48 g of PAG Intermediate 3, 59 2 of 2,3,5-triiodobenzoic acid, 1.5 g of sodium iodide, 18 g of potassium carbonate, and 480 g of dimethylformamide was heated at 90° C. for 24 hours. Thereafter, 1,000 g of water and 1,000 g of methylene chloride were added thereto. The organic layer was taken out, washed with water, and concentrated under reduced pressure. To the residue was added 200 g of diisopropyl ether. The thus precipitated crystal was collected and dried in vacuum by heating. There was obtained 52 g of the end compound, PAG Intermediate 4 as white solid (yield 55%).

Example 1-5

Synthesis of PAG-A

A mixture of 23 g of PAG intermediate 2, 38 g of PAG Intermediate 4, 300 g of methylene chloride, and 100 g of water was stirred at room temperature for 30 minutes. The organic layer was taken out, washed with water, and concentrated under reduced pressure. The concentrate was washed with diisopropyl ether, obtaining 47 g of the target compound, PAG-A as oily matter (yield 99%).

Figure 2:
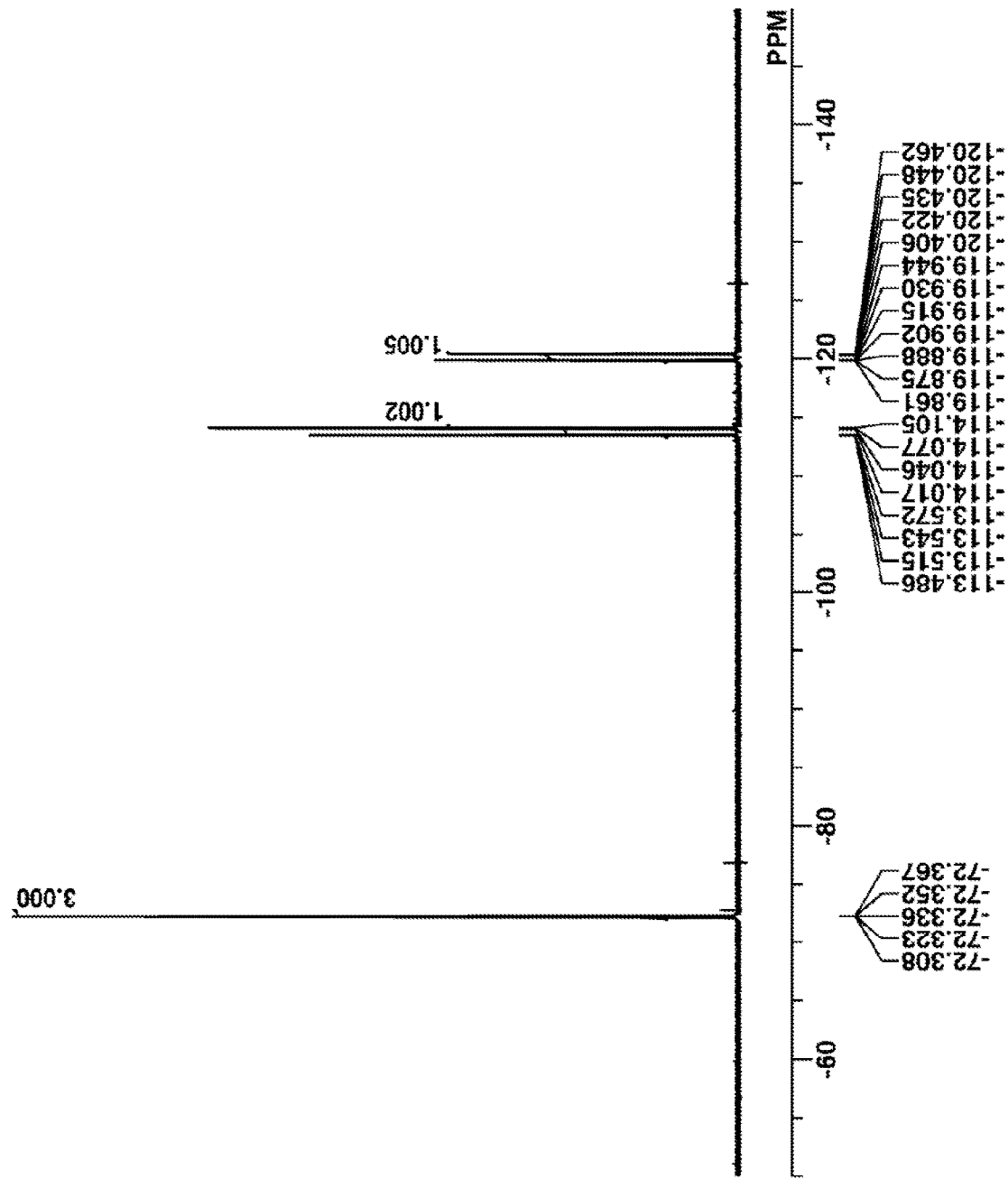

PAG-A was analyzed by spectroscopy. The NMR spectra, $^1$H- and $^{19}$F-NMR in DMSO-$d_6$ are shown in. FIGS. 1 and 2. In $^1$H-NMR analysis, minute amounts of residual solvent (diisopropyl ether) and water in DMSO-$d_6$ were observed.

IR (D-ATR): 3063, 2967, 1771, 1719, 1635, 1589, 1520, 1495, 1476, 1447, 1369, 1266, 1181, 1106, 1070, 998, 924, 835, 749, 684, 642, 526 cm$^{-1}$

TGF-MS (MALDI): Positive M$^+$391 (corresponding to $C_{24}H_{23}O_3S$) Negative M$^-$796 (corresponding to $C_{14}H_9F_5I_3O_7S$)

2) Synthesis of Polymers

Example 2-1

Synthesis of Polymer P-1

In a flask under nitrogen atmosphere, 69.6 g of PAG-A, 24.1 g of 3-ethyl-3-exo-tetracyclo[4.4.0.1$^{2,5}$0.1$^{7.10}$]dodecanyl methacrylate, 10.4 g of 4-hydroxyphenyl methacrylate, 19.7 g of 4,8-dioxatricyclo[4.2.1.0$^{3,7}$]nonan-5-on-2-yl methacrylate, 3.4 g of dimethyl 2,2'-azobis(isobutyrate), 0.69 g of 2-mercaptoethanol, and 214 g of MEK were combined to form a monomer solution. Another flask in nitrogen atmosphere was charged with 71 g of MEK, which was heated at 80° C. with stifling. With stirring, the monomer solution was added dropwise to the flask over 4 hours.

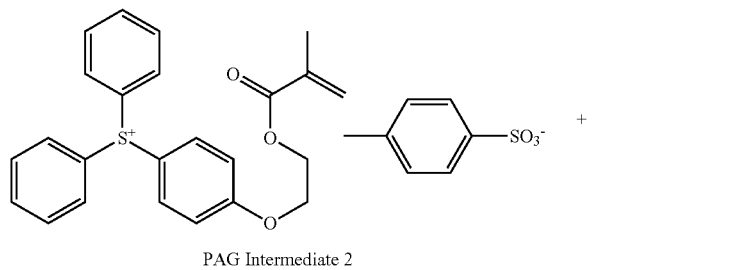

PAG Intermediate 2

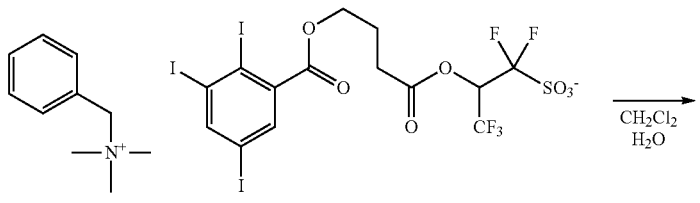

PAG Intermediate 4

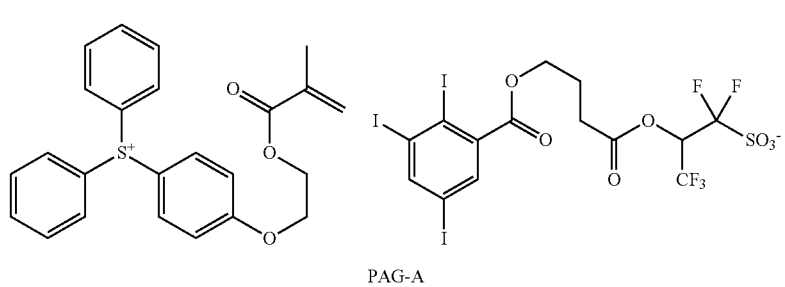

PAG-A

After the completion of dropwise addition, the polymerization solution was continuously stirred for 2 hours while maintaining the temperature of 80° C. The polymerization solution was cooled to room temperature, whereupon it was added dropwise to a mixture of 100 g of MEK and 900 g of hexane. The thus precipitated copolymer was collected by filtration, washed twice with 600 g of methanol, and vacuum dried at 50° C. for 20 hours, obtaining Polymer P-1 in white powder solid form (amount 115 g, yield 93%). Polymer P-1 had a Mw of 14,200 and a dispersity Mw/Mn of 1.75.

P-1

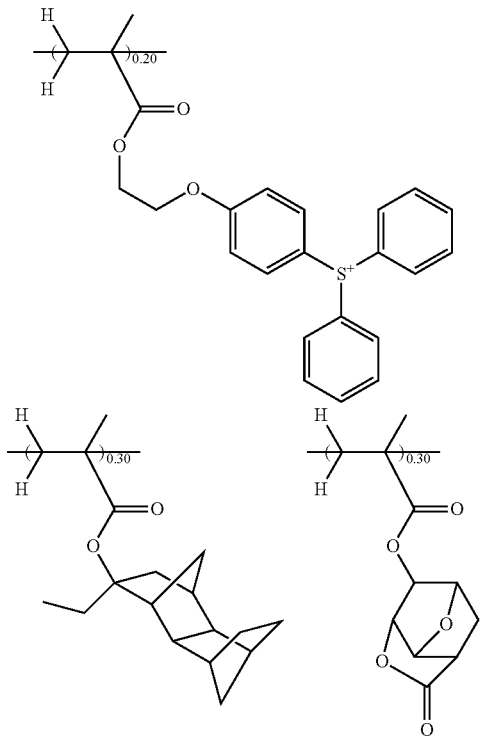

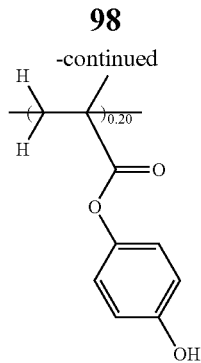

Examples 2-2 to 2-8 & Comparative Examples 1-1 to 1-5

Synthesis of Polymers P-2 to P-13

Polymers were synthesized by the same procedure as in Example 2-1 aside from charming the type and amount of monomers. Table 1 shows the proportion (in molar ratio) of units incorporated in these polymers. The structure of recurring units is shown in Tables 2 to 4. It is noted that PAG-B and PAG-C in Table 2 were synthesized with reference to WO 2007/069640 and JP-A 2008-133448 (U.S. Pat. No. 7,569,326) respectively.

TABLE 1

|  |  | Polymer | Unit 1 (molar ratio) | Unit 2 (molar ratio) | Unit 3 (molar ratio) | Unit 4 (molar ratio) | Mw | Mw/Mn |
|---|---|---|---|---|---|---|---|---|
| Example | 2-1 | P-1 | PAG-A (0.20) | A-1 (0.30) | B-1 (0.20) | B-4 (0.30) | 14,200 | 1.75 |
|  | 2-2 | P-2 | PAG-A (0.20) | A-2 (0.30) | B-1 (0.20) | B-3 (0.30) | 13,852 | 1.69 |
|  | 2-3 | P-3 | PAG-A (0.20) | A-3 (0.30) | B-1 (0.20) | B-5 (0.30) | 13,118 | 1.79 |
|  | 2-4 | P-4 | PAG-A (0.20) | A-4 (0.45) | B-2 (0.35) | — | 14,684 | 1.78 |
|  | 2-5 | P-5 | PAG-A (0.20) | A-2 (0.45) | B-2 (0.35) | — | 13,555 | 1.61 |
|  | 2-6 | P-6 | PAG-A (0.20) | A-1 (0.35) | B-4 (0.45) | — | 13,278 | 1.73 |
|  | 2-7 | P-7 | PAG-A (0.20) | A-2 (0.30) | B-3 (0.45) | B-6 (0.05) | 14,052 | 1.65 |
|  | 2-8 | P-8 | PAG-A (0.20) | A-2 (0.30) | B-5 (0.45) | B-6 (0.05) | 14,694 | 1.80 |
| Comparative Example | 1-1 | P-9 | PAG-B (0.20) | A-1 (0.30) | B-1 (0.20) | B-4 (0.30) | 14,752 | 1.67 |
|  | 1-2 | P-10 | PAG-C (0.20) | A-1 (0.30) | B-1 (0.20) | B-4 (0.30) | 13,792 | 1.71 |
|  | 1-3 | P-10 | PAG-B (0.20) | A-2 (0.30) | B-5 (0.45) | B-6 (0.05) | 13,297 | 1.64 |
|  | 1-4 | P-12 | A-1 (0.30) | B-1 (0.20) | B-4 (0.50) | — | 8,752 | 1.82 |

TABLE 1-continued

| | Polymer | Unit 1 (molar ratio) | Unit 2 (molar ratio) | Unit 3 (molar ratio) | Unit 4 (molar ratio) | Mw | Mw/Mn |
|---|---|---|---|---|---|---|---|
| 1-5 | P-13 | A-2 (0.40) | B-3 (0.50) | B-6 (0.10) | — | 8,478 | 1.84 |

TABLE 2

| PAG-A | PAG-B | PAG-C |
|---|---|---|

TABLE 3

| A-1 | A-2 | A-3 | A-4 |
|---|---|---|---|

TABLE 4

| B-1 | B-2 | B-3 | B-4 | B-5 | B-6 |
|---|---|---|---|---|---|

3) Preparation of Resist Composition

Examples 3-1 to 3-10 and Comparative Examples 2-1 to 2-5

Resist compositions in solution form were prepared by dissolving an acid diffusion inhibitor (Q-1), Polymer (P-1 to P-13), photoacid generator (PAG-X), and alkali-soluble surfactant (F-1) in an organic solvent containing 0.01 wt % of surfactant A in accordance with the formulation shown in Table 5, and filtering through a Teflon® filter with a pore size of 0.2 μm.

The solvent, photoacid generator (PAG-X), alkali-soluble surfactant (F-1), surfactant A, and acid diffusion inhibitor (Q-1) used herein are identified below.

Solvent: PGMEA=propylene glycol monomethyl ether acetate

GBL=γ-butyrolactone

CyHO=cyclohexanone

Photoacid generator (PAG-X): triphenylsulfonium 2-(adamantane-1-carbonyloxy)-1,1,3,3,3-pentafluoropropane-1-sulfonate Acid diffusions inhibitor (Q-1); 2-(4-morpholinyl)ethyl laurate Alkali-soluble surfactant (F-1): poly(2,2,3,3,44,4-heptafluoro-1-isobutyl-1-butyl methacrylate/9-(2,2,2-trifluoro-1-trifluomethyloxy-carbonyl)-4-oxatricyclo[4.7.10³·]nonan-5-on-2-yl methacrylate)

Mw=7,700

Mw/Mn=1.82

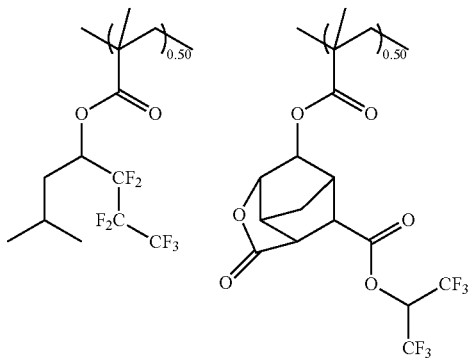

F-1

Surfactant A: 3-methyl-3-(2,2,2-trifluoroethoxymethyl)oxetane/tetrahydrofuran/2,2-dimethyl-1,3-propmediol copolymer (Omnova Solutions, Inc.)

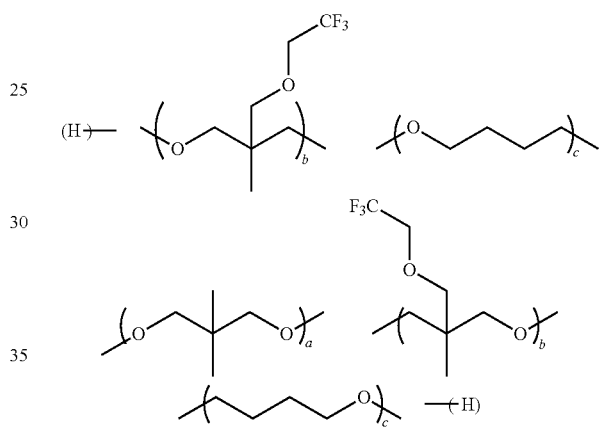

a:(b + b'):(c + c') = 1:4 - 7:0.01 - 1 (molar ration)
Mw = 1,500

TABLE 5

| | | Resist composition | Resin (pbw) | PAG (pbw) | Acid diffusion inhibitor (pbw) | Surfactant (pbw) | Solvent 1 (pbw) | Solvent 2 (pbw) |
|---|---|---|---|---|---|---|---|---|
| Example | 3-1 | R-01 | P-1 (80) | — | Q-1 (0.6) | — | PGMEA (576) | CyHO (1,728) |
| | 3-2 | R-02 | P-2 (80) | — | Q-1 (0.6) | — | PGMEA (576) | CyHO (1,728) |
| | 3-3 | R-03 | P-3 (80) | — | Q-1 (0.6) | — | PGMEA (576) | CyHO (1,728) |
| | 3-4 | R-04 | P-4 (80) | — | Q-1 (0.6) | — | PGMEA (576) | CyHO (1,728) |
| | 3-5 | R-05 | P-5 (80) | — | Q-1 (0.6) | — | PGMEA (576) | CyHO (1,728) |
| | 3-6 | R-06 | P-6 (80) | — | Q-1 (0.6) | F-1 (5.0) | PGMEA (1,728) | GBL (192) |
| | 3-7 | R-07 | P-7 (80) | — | Q-1 (0.6) | F-1 (5.0) | PGMEA (1,728) | GBL (192) |
| | 3-8 | R-08 | P-8 (80) | — | Q-1 (0.6) | F-1 (5.0) | PGMEA (1,728) | GBL (192) |
| | 3-9 | R-09 | P-1 (80) | PAG-X (3.8) | Q-1 (0.6) | — | PGMEA (576) | CyHO (1,728) |
| | 3-10 | R-10 | P-6 (80) | PAG-X (3.8) | Q-1 (0.6) | F-1 (5.0) | PGMEA (1,728) | GBL (192) |
| Comparative Example | 2-1 | R-11 | P-9 (80) | — | Q-1 (0.6) | — | PGMEA (576) | CyHO (1,728) |
| | 2-2 | R-12 | P-10 (80) | — | Q-1 (0.6) | — | PGMEA (576) | CyHO (1,728) |

TABLE 5-continued

|  | Resist composition | Resin (pbw) | PAG (pbw) | Acid diffusion inhibitor (pbw) | Surfactant (pbw) | Solvent 1 (pbw) | Solvent 2 (pbw) |
|---|---|---|---|---|---|---|---|
| 2-3 | R-13 | P-11 (80) | — | Q-1 (0.6) | — | PGMEA (1,728) | GBL (192) |
| 2-4 | R-14 | P-12 (80) | PAG-X (25) | Q-1 (0.6) | — | PGMEA (576) | CyHO (1,728) |
| 2-5 | R-15 | P-13 (80) | PAG-X (13) | Q-1 (0.6) | F-1 (5.0) | PGMEA (1,728) | GBL (192) |

4) EUV Lithography Test

Examples 4-1 to 4-6 and Comparative Examples 3-1 to 3-3

The resist composition in Table 6 was spin coated on a silicon substrate having a 20-nm coating of silicon-containing spin-on hard mask SHB-A940 (silicon content 43 wt. %, Shin-Etsu Chemical Co., Ltd.) and prebaked on a hotplate at 105° C. for 60 seconds to form a resist film of 60 nm thick. Using an EUV scanner NXE3300 (ASML, NA 0.33, σ0.9/0.6, quadrupole illumination), the resist film was exposed to EUV through a mask bearing a hole pattern having a pitch of 46 nm and +20% bias (on-wafer size). The resist film was baked (PEB) at the temperature shown in Table 6 for 60 seconds and developed in a 2.38 wt % TMAH aqueous solution for 30 seconds to form a hole pattern having a size of 23 nm.

The resist pattern was evaluated. The exposure dose that provides a hole pattern having a size of 23 nm is reported as sensitivity. The size of 50 holes was measured under CD-SEM (CG-5000, Hitachi High-Technologies Corp.), from which a size variation (3σ) was computed and reported as CDU. The results are shown in Table 6.

TABLE 6

|  |  | Resist composition | PEB temp. (° C.) | Sensitivity (mJ/m$^2$) | CDU (nm) |
|---|---|---|---|---|---|
| Example | 4-1 | R-01 | 75 | 23 | 3.2 |
|  | 4-2 | R-02 | 80 | 25 | 2.6 |
|  | 4-3 | R-03 | 80 | 28 | 2.9 |
|  | 4-4 | R-04 | 75 | 24 | 2.6 |
|  | 4-5 | R-05 | 80 | 25 | 2.4 |
|  | 4-6 | R-09 | 70 | 23 | 2.5 |
| Comparative Example | 3-1 | R-11 | 75 | 32 | 4.2 |
|  | 3-2 | R-12 | 75 | 30 | 4.0 |
|  | 3-3 | R-14 | 80 | 35 | 4.0 |

5) ArF Immersion Lithography Patterning Test

Examples 5-1 to 5-4 and Comparative Examples 4-1 to 4-2

On a substrate (silicon, wafer), a spin-on carbon film ODL-102 (carbon content 80 wt %, Shin-Etsu Chemical Co., Ltd.) was deposited to a thickness of 200 nm and a silicon-containing spin-on hard mask SHB-A940 (silicon content 43 wt %) was deposited thereon to a thickness of 35 nm. On this substrate for trilayer process, each of the resist compositions in Table 7 was spin coated, then baked on a hotplate at 100° C. for 60 seconds to form a resist film of 80 nm thick.

Using an ArF excimer laser scanner NSR-S610C (Nikon Corp., NA 1.30, σ0.98/0.78, 35° cross-pole illumination, azimuthally polarized illumination), the resist film was exposed by immersion lithography through a 6% halftone phase shift mask bearing a pattern having a line of 50 nm and a pitch of 100 nm (on-wafer size). The immersion liquid was water. The resist film was baked (PEB) at the temperature shown in Table 7 for 60 seconds. After PEB, the resist film was developed in 2.38 wt % TMAH aqueous solution, yielding a line-and-space (L/S) pattern having a space of 50 nm and a pitch of 100 nm.

The pattern was observed under a CD-SEM (CG-4000, Hitachi High-Technologies Corp.). The exposure dose capable of resolving a L/S pattern at 1:1 was determined as sensitivity, and edge roughness (LWR) was measured. The results are shown in Table 7.

TABLE 7

|  |  | Resist composition | PEB temp. (° C.) | Sensitivity (mJ/cm$^2$) | LWR (nm) |
|---|---|---|---|---|---|
| Example | 5-1 | R-06 | 95 | 31 | 3.8 |
|  | 5-2 | R-07 | 100 | 36 | 2.8 |
|  | 5-3 | R-08 | 100 | 38 | 3.0 |
|  | 5-4 | R-10 | 95 | 28 | 3.9 |
| Comparative Example | 4-1 | R-13 | 100 | 37 | 4.6 |
|  | 4-2 | R-15 | 100 | 39 | 4.9 |

It is demonstrated in Tables 6 and 7 that resist compositions comprising a photoacid generator having a polymer-bound cation moiety and an iodized anion moiety within the scope of the invention offer a high sensitivity and improved CDU and LWR.

Japanese Patent Application No. 2017-145057 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonium salt comprising an anion having the formula (1a) and a sulfonium cation having the formula (1b) or (1C):

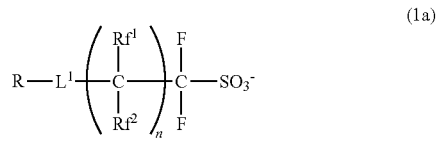

(1a)

wherein R is a $C_1$-$C_{20}$ straight, branched or cyclic monovalent hydrocarbon group containing at least one iodine atom, $Rf^1$ and $Rf^2$ are each independently hydrogen, fluorine or trifluoromethyl, n is an integer of 0 to 5, and $L^1$ is a single bond, or a divalent group containing an ether bond, thioether bond, ester bond, sulfonic acid ester bond, carbonate bond or carbamate bond, (1b)

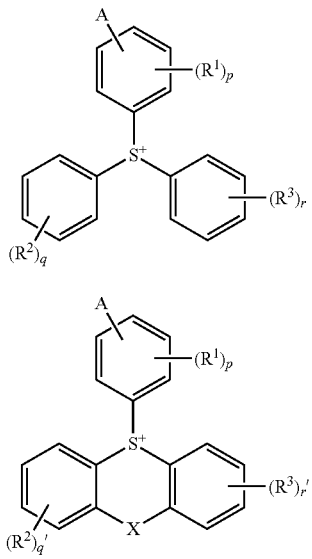

(1c)

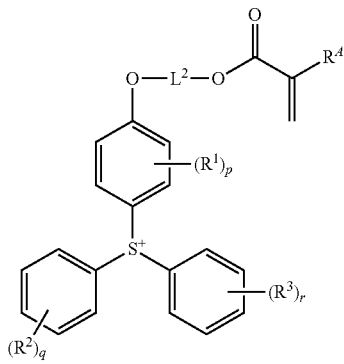

wherein A is an organic group having a polymerizable group, $R^1$, $R^2$ and $R^3$ are each independently a halogen, nitro, cyano, or $C_1$-$C_{20}$ straight, branched or cyclic monovalent hydrocarbon group which may contain a heteroatom, where a plurality of groups $R^1$, $R^2$ or $R^3$ are included, two adjacent groups $R^1$, $R^2$ or $R^3$ may bond together to form a ring with the carbon atoms to which they are attached, X is a single bond, or —O—, —NH—, —S—, —SO—, —SO$_2$—, —CO— or —CH$_2$—, p is an integer of 0 to 4, q and r are each independently an integer of 0 to 5, q' and r' are each independently an integer of 0 to 4.

2. The sulfonium salt of claim 1 wherein the sulfonium cation has the formula (1b-1) or (1c-1):

(1b-1)

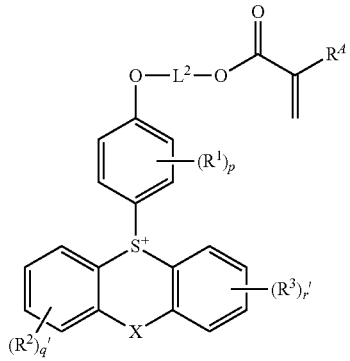

(1c-1)

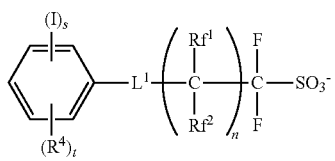

wherein $R^1$, $R^2$, $R^3$, X, p, q, r, q' and r' are as defined above, $L^2$ is a $C_1$-$C_{20}$ straight, branched or cyclic divalent hydrocarbon group which may contain a heteroatom, and $R^A$ is each independently hydrogen or methyl.

3. The sulfonium salt of claim 1 wherein the anion has the formula (1a-1):

(1a-1)

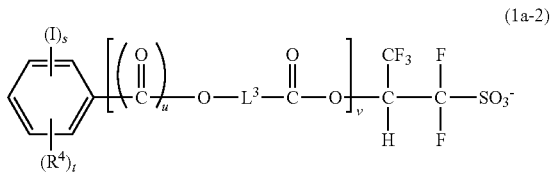

wherein $Rf^1$, $Rf^2$, $L^1$ and n are as defined above, $R^4$ is a $C_1$-$C_{20}$ straight, branched or cyclic monovalent hydrocarbon group which may contain a heteroatom, s is an integer of 1 to 5, t is an integer of 0 to 4, and $1 \leq s+t \leq 5$.

4. The sulfonium salt of claim 3 wherein the anion has the formula (1a-2):

(1a-2)

wherein $R^4$, s and t are as defined above, $L^3$ is a $C_1$-$C_{20}$ straight, branched or cyclic divalent hydrocarbon group which may contain a heteroatom, u and v are each independently 0 or 1.

5. The sulfonium salt of claim 1 wherein R is a $C_1$-$C_{20}$ straight, branched or cyclic monovalent hydrocarbon group containing at least two iodine atoms.

6. The sulfonium salt of claim 1 wherein R is a $C_6$-$C_{20}$ aryl group containing at least one iodine atom.

* * * * *